United States Patent
Mossman

(10) Patent No.: US 7,893,093 B2
(45) Date of Patent: Feb. 22, 2011

(54) SULFONYL CONTAINING COMPOUNDS AS CYSTEINE PROTEASE INHIBITORS

(75) Inventor: Craig J. Mossman, Saratoga, CA (US)

(73) Assignee: ViroBay, Inc., Menlo Park, CA (US)

( * ) Notice: Subject to any disclaimer, the term of this patent is extended or adjusted under 35 U.S.C. 154(b) by 554 days.

(21) Appl. No.: 11/909,053

(22) PCT Filed: Mar. 22, 2006

(86) PCT No.: PCT/US2006/010640

§ 371 (c)(1), (2), (4) Date: May 12, 2008

(87) PCT Pub. No.: WO2006/102535

PCT Pub. Date: Sep. 28, 2006

(65) Prior Publication Data

US 2008/0287446 A1      Nov. 20, 2008

Related U.S. Application Data

(60) Provisional application No. 60/664,139, filed on Mar. 22, 2005.

(51) Int. Cl.
C07D 211/30 (2006.01)
A61K 31/44 (2006.01)

(52) U.S. Cl. .................. 514/357; 514/333; 514/618; 514/626; 544/335; 546/247; 546/330; 564/162; 564/193

(58) Field of Classification Search .................. None
See application file for complete search history.

(56) References Cited

U.S. PATENT DOCUMENTS

| | | | |
|---|---|---|---|
| 6,420,364 | B1 | 7/2002 | Emmanuel et al. |
| 6,506,733 | B1 | 1/2003 | Buysse et al. |
| 6,730,671 | B2 | 5/2004 | Cywin et al. |
| 2003/0092634 | A1 | 5/2003 | Buysse et al. |
| 2004/0127426 | A1 | 7/2004 | Graupe et al. |
| 2005/0014941 | A1 | 1/2005 | Black et al. |
| 2006/0111440 | A1 | 5/2006 | Gauthier et al. |

FOREIGN PATENT DOCUMENTS

| | | |
|---|---|---|
| EP | 0 623 627 A1 | 11/1994 |
| WO | WO 99/24460 A3 | 5/1999 |
| WO | WO 00/05514 A1 | 9/2000 |
| WO | WO 00/51998 | 9/2000 |
| WO | WO 00/55125 A2 | 9/2000 |
| WO | WO 01/19796 A1 | 3/2001 |
| WO | WO 01/19816 A1 | 3/2001 |
| WO | WO 01/49288 A1 | 7/2001 |
| WO | WO 01/68645 A2 | 9/2001 |
| WO | WO 02/20485 A1 | 3/2002 |
| WO | WO 02/069901 A2 | 9/2002 |
| WO | WO 02/074904 A2 | 9/2002 |
| WO | WO 02/098850 A2 | 12/2002 |
| WO | WO 03/024924 A1 | 3/2003 |
| WO | WO 03/029200 A2 | 4/2003 |
| WO | WO 03/097617 A1 | 11/2003 |
| WO | WO 2004/083182 A1 | 3/2004 |
| WO | WO 2004/033445 A1 | 4/2004 |
| WO | WO 2004/108661 A1 | 12/2004 |
| WO | WO 2005/021487 A1 | 3/2005 |
| WO | WO 2005/028454 A1 | 3/2005 |
| WO | WO 2005/040142 | 5/2005 |
| WO | WO 2005/058348 A1 | 6/2005 |
| WO | WO 2005/063742 A2 | 7/2005 |
| WO | WO 2005/074904 A2 | 8/2005 |
| WO | WO 2006/034004 A2 | 3/2006 |

OTHER PUBLICATIONS

Bundgaard, et al. "A Novel Solution-Stable, Water-Soluble Prodrug Type for Drugs Containing a Hydroxyl or an NH-Acidic Group," J. Med. Chem., 1989 vol. 32, No. 12, pp. 2503-2507.
Greenspan, et al. Identification of Dipeptidyl Nitriles as Potent and Selective Inhibitors of Cathepsin B through Structure-Based Drug Design, J. Med. Chem., 2001, vol. 44, pp. 4524-4534.
Gong, Y., et al., "Convenient Substitution of Hydroxypyridines with Trifluoroacetaldehyde Ethyl Hemiacetal," Journal of Heterocyclic Chemistry 2001, vol. 38, No. 1, p. 25-28.
Volonterio, et al., "Solution/solid-phase synthesis of partially modified retro-ψ [NHCH(CF$_3$)]-peptidyl hydroxamates", Tetrahedron Letters, 2001, vol. 42, pp. 3141-3144.

*Primary Examiner*—Zinna N Davis
(74) *Attorney, Agent, or Firm*—Kilpatrick Townsend & Stockton LLP

(57) ABSTRACT

The present invention is directed to compounds that are inhibitors of cysteine proteases, in particular, cathepsins B, K, L, F, and S and are therefore useful in treating diseases mediated by these proteases. The present invention is directed to pharmaceutical compositions comprising these compounds and processes for preparing them.

13 Claims, No Drawings

SULFONYL CONTAINING COMPOUNDS AS CYSTEINE PROTEASE INHIBITORS

CROSS-REFERENCES TO RELATED APPLICATIONS

This application is a 371 of PCT/US2006/010640 filed Mar. 22, 2006 which claims the benefit of Provisional Patent Application No. 60/664,139, filed Mar. 22, 2005 the content of which is incorporated herein by reference.

STATEMENT AS TO RIGHTS TO INVENTIONS MADE UNDER FEDERALLY SPONSORED RESEARCH OR DEVELOPMENT

Not Applicable

REFERENCE TO A "SEQUENCE LISTING," A TABLE, OR A COMPUTER PROGRAM LISTING APPENDIX SUBMITTED ON A COMPACT DISK

Not Applicable

BACKGROUND OF THE INVENTION

1. Field of the Invention

The present invention is directed to compounds that are inhibitors of cysteine proteases, in particular, cathepsins B, K, L, F, and S and are therefore useful in treating diseases mediated by these proteases. The present invention is also directed to pharmaceutical compositions comprising these compounds and processes for preparing them.

2. State of the Art

Cysteine proteases represent a class of peptidases characterized by the presence of a cysteine residue in the catalytic site of the enzyme. Cysteine proteases are associated with the normal degradation and processing of proteins. The aberrant activity of cysteine proteases, e.g., as a result of increased expression or enhanced activation, however, may have pathological consequences. In this regard, certain cysteine proteases are associated with a number of disease states, including arthritis, muscular dystrophy, inflammation, tumor invasion, glomerulonephritis, malaria, periodontal disease, metachromatic leukodystrophy and others. For example, increased cathepsin B levels and redistribution of the enzyme are found in tumors; thus, suggesting a role for the enzyme in tumor invasion and metastasis. In addition, aberrant cathepsin B activity is implicated in such disease states as rheumatoid arthritis, osteoarthritis, pneumocystis carinii, acute pancreatitis, inflammatory airway disease and bone and joint disorders.

The prominent expression of cathepsin K in osteoclasts and osteoclast-related multinucleated cells and its high collagenolytic activity suggest that the enzyme is involved in osteoclast-mediated bone resorption and, hence, in bone abnormalities such as occurs in osteoporosis. In addition, cathepsin K expression in the lung and its elastinolytic activity suggest that the enzyme plays a role in pulmonary disorders as well.

Cathepsin L is implicated in normal lysosomal proteolysis as well as in several disease states, including, but not limited to, metastasis of melanomas. Cathepsin S is implicated in Alzheimer's disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis, neuropathic pain, and Hashimoto's thyroiditis. In addition, cathepsin S is implicated in: allergic disorders, including, but not limited to asthma; and allogeneic immune responses, including, but not limited to, rejection of organ transplants or tissue grafts.

In view of the number of diseases wherein it is recognized that an increase in cysteine protease activity contributes to the pathology and/or symptomatology of the disease, molecules which inhibit the activity of this class of enzymes, in particular molecules which inhibit cathepsins B, K, L, F, and/or S, will therefore be useful as therapeutic agents.

SUMMARY OF THE INVENTION

In a first aspect, this invention is directed to a compound of Formula (I):

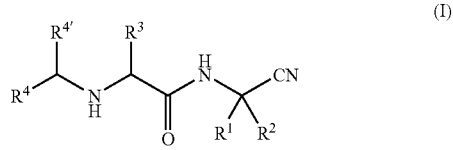

wherein:
$R^1$ is hydrogen, alkyl, or haloalkyl;
$R^2$ is hydrogen, alkyl, or haloalkyl; or
$R^1$ and $R^2$ taken together with the carbon atom to which $R^1$ and $R^2$ are attached form cycloalkylene optionally substituted with one to four fluoro, piperidin-4-yl wherein the nitrogen atom of the piperidinyl ring is substituted with alkyl, haloalkyl, or cycloalkyl, tetrahydropyran-4-yl, tetrahydrothiopyran-4-yl, 1,1-dioxohexahydrothiopyran-4-yl, or —$CH_2$—O—$CH_2$—;
$R^3$ is -alkylene-$SO_2$-alkyl, -alkylene-$SO_2$-haloalkyl, -alkylene-$SO_2$-cycloalkyl, -alkylene-$SO_2$-cycloalkylalkyl, -alkylene-$SO_2$-aryl, -alkylene-$SO_2$-aralkyl, -alkylene-$SO_2$-heterocycloalkyl, -alkylene-$SO_2$-heterocycloalkylalkyl, -alkylene-$SO_2$-heteroaryl, -alkylene-$SO_2$-heteroaralkyl, -alkylene-$SO_2$-haloalkylene-aryl or -alkylene-$SO_2$-haloalkylene-heteroaryl wherein the aromatic or alicyclic ring in $R^3$ is optionally substituted with one, two, or three $R^a$ independently selected from alkyl, alkylsulfonyl, haloalkyl, alkoxy, hydroxy, hydroxyalkyl, haloalkoxy, halo, nitro, cyano, carboxy, alkoxycarbonyl, aryl, heteroaryl, cycloalkyl, amino, alkylamino, dialkylamino, aminocarbonyl, or acyl and further wherein the aromatic ring in $R^a$ is optionally substituted with one, two, or three $R^b$ independently selected from alkyl, alkoxy, alkylsulfonyl, hydroxy, or halo;
$R^4$ is hydrogen, alkyl, haloalkyl, aryl, heteroaryl, or heterocycloalkyl attached via a carbon ring atom wherein the aromatic or alicyclic ring in $R^4$ is optionally substituted by one, two, or three $R^f$ independently selected from alkyl, halo, hydroxy, alkoxy, alkylcarbonyl, alkylsulfonyl, alkylsulfonylamino, aminocarbonyl, haloalkyl, haloalkoxy, carboxy, or alkoxycarbonyl;
$R^{4'}$ is difluoromethyl, trifluoromethyl, 1,1,2,2,2-pentafluoroethyl, chlorodifluoromethyl, 1,1-dichloro-2,2,2-trifluoroethyl, 1,1,2,2-tetrafluoroethyl, trichloromethyl, dichlorofluoromethyl, 1,1,2,2,3,3,3-heptafluoropropyl, or 1,1,2,2,3,3-hexafluoropropyl, or a pharmaceutically acceptable salt thereof provided that:
(a) when $R^1$ and $R^2$ taken together with the carbon atom to which $R^1$ and $R^2$ are attached form cyclopropylene, $R^3$ is phenylmethanesulfonylmethyl, cyclopropylmethanesulfonylmethyl, pyridin-2-ylmethanesulfonylmethyl, 2-difluoromethoxyphenylmethanesulfonylmethyl, or 2-trifluoromethylpyridin-6-methanesulfonylmethyl, $R^4$ is phenyl, 4-hydroxyphenyl, 3-bromophenyl, 4-fluorophenyl, 3-chloro-4-hydroxyphenyl, 3,4-difluorophenyl, or 3,4,5-trifluorophenyl, then $R^{4'}$ is not trifluoromethyl or difluoromethyl;

(b) when $R^1$ and $R^2$ taken together with the carbon atom to which $R^1$ and $R^2$ are attached form cyclopropylene, $R^3$ is phenylmethanesulfonylmethyl, difluoromethoxyphenylmethanesulfonylmethyl, or cyclopropylmethanesulfonylmethyl, $R^4$ is furan-2-yl, indol-3-yl, thiophen-2-yl, 1-methylpyrrol-2-yl, pyridin-2-yl, thiophen-3-yl or 1-oxo-1-methylpyrrol-2-yl, then $R^4$ is not difluoromethyl or trifluoromethyl;

(c) when $R^1$ and $R^2$ taken together with the carbon atom to which $R^1$ and $R^2$ are attached form 1,1-dioxohexahydrothiopyran-4-ylene, $R^3$ is phenylmethanesulfonylmethyl, 4-fluorophenylmethanesulfonylmethyl, or difluoromethoxyphenylmethanesulfonylmethyl, then $R^{4'}$ is not trifluoromethyl; and (d) when $R^1$ and $R^2$ taken together with the carbon atom to which $R^1$ and $R^2$ are attached form tetrahydropyran-4-ylene or tetrahydrothiopyran-4-ylene, $R^3$ is cyclopropylmethanesulfonylmethyl or difluoromethoxyphenylmethanesulfonylmethyl, $R^4$ is 4-fluorophenyl, then $R^{4'}$ is not trifluoromethyl.

In a second aspect, this invention is directed to a pharmaceutical composition comprising a compound of Formula (I) or a pharmaceutically acceptable salt thereof in admixture with one or more suitable excipients.

In a third aspect, this invention is directed to a method for treating a disease in an animal mediated by cysteine proteases, in particular cathepsin S, which method comprises administering to the animal a pharmaceutical composition comprising a therapeutically effective amount of a compound of Formula (I) or a pharmaceutically acceptable salt thereof in admixture with one or more suitable excipients.

In a fourth aspect, this invention is directed to processes for preparing compounds of Formula (I).

In a fifth aspect, this invention is directed to a method of treating a patient undergoing a therapy wherein the therapy causes an immune response, preferably a deleterious immune response, in the patient comprising administering to the patient a compound of Formula (I) or a pharmaceutically acceptable salt thereof. Preferably, the immune response is mediated by MHC class II molecules. The compound of this invention can be administered prior to, simultaneously, or after the therapy. Preferably, the therapy involves treatment with a biologic. Preferably, the therapy involves treatment with a small molecule.

Preferably, the biologic is a protein, preferably an antibody, more preferably monoclonal antibody. More preferrably, the biologic is Remicade®, Refacto®, Referon-A®, Factor VIII, Factor VII, Betaseron®, Epogen®, Enbrel®, Interferon beta, Botox®, Fabrazyme®, Elspar®, Cerezyme®, Myobloc®, Aldurazyme®, Verluma®, Interferon alpha, Humira®, Aranesp®, Zevalin® or OKT3.

Preferably, the treatment involves use of heparin low molecular weight heparin, procainamide or hydralazine.

In a sixth aspect, this invention is directed to a method of treating immune response in an animal that is caused by administration of a biologic to the animal which method comprises administering to the animal in need of such treatment a therapeutically effective amount of a compound of Formula (I) or a pharmaceutically acceptable salt thereof.

In a seventh aspect, this invention is directed to a method of conducting a clinical trial for a biologic comprising administering to an individual participating in the clinical trial a compound of Formula (I) or a pharmaceutically acceptable salt thereof with the biologic.

In an eight aspect, this invention is directed to a method of prophylactically treating a patient undergoing treatment with a biologic with a compound of Formula (I) or a pharmaceutically acceptable salt thereof to treat the immune response caused by the biologic in the patient.

In a ninth aspect, this invention is directed to a method of determining the loss in the efficacy of a biologic in an animal due to the immune response caused by the biologic comprising administering the biologic to the animal in the presence and absence of a compound of Formula (I) or a pharmaceutically acceptable salt thereof.

In a tenth aspect, this invention is directed to a method of improving efficacy of a biologic in an animal comprising administering the biologic to the animal with a compound of Formula (I) or a pharmaceutically acceptable salt thereof.

In an eleventh aspect, this invention is directed to the use of a compound of Formula (I) or a pharmaceutically acceptable salt thereof for the manufacture of a medicament. Preferably, the medicament is for use in the treatment of a disease mediated by Cathepsin S.

In a twelfth aspect, this invention is directed to the use of a compound of Formula (I) or a pharmaceutically acceptable salt thereof for the manufacture of a medicament for combination therapy with a biologic, wherein the compound of this invention treats the immune response caused by the biologic. Preferably, the compound(s) of the invention is administered prior to the administration of the biological agent. Preferably, the compound(s) of the invention is administered concomitantly with the biological agent. Preferably, the compound(s) of the invention is administered after the administration of the biological agent.

DETAILED DESCRIPTION OF THE INVENTION

Definitions

Unless otherwise stated, the following terms used in the specification and claims are defined for the purposes of this Application and have the following meanings.

"Alicyclic" means a moiety characterized by arrangement of the carbon atoms in closed non-aromatic ring structures e.g., cycloalkyl and heterocycloalkyl rings as defined herein.

"Alkyl" represented by itself means a straight or branched, saturated aliphatic radical containing one to eight carbon atoms, unless otherwise indicated e.g., alkyl includes methyl, ethyl, propyl, isopropyl, butyl, sec-butyl, isobutyl, tert-butyl, and the like.

"Alkylene", unless indicated otherwise, means a straight or branched, saturated aliphatic, divalent radical having the number of one to six carbon atoms, e.g., methylene ($-CH_2-$), ethylene ($-CH_2CH_2-$), trimethylene ($-CH_2CH_2CH_2-$), tetramethylene ($-CH_2CH_2CH_2CH_2-$) 2-methyltetramethylene ($-CH_2CH(CH_3)CH_2CH_2-$), pentamethylene ($-CH_2CH_2CH_2CH_2CH_2-$), and the like.

"Alkoxy" refers to a $-OR$ radical where R is an alkyl group as defined above e.g., methoxy, ethoxy, and the like.

"Alkylsulfonyl" refers to a $-SO_2R$ radical where R is an alkyl group as defined above e.g., methylsulfonyl, ethylsulfonyl, and the like.

"Alkylsulfonylamino" refers to a $-NHSO_2R$ radical where R is an alkyl group as defined above e.g., methylsulfonylamino, ethylsulfonylamino, and the like.

"Alkoxycarbonyl" refers to a —C(O)OR radical where R is an alkyl group as defined above e.g., methoxycarbonyl, ethoxycarbonyl, and the like.

"Amino" means —NH$_2$ radical.

"Aminocarbonyl" refers to a —CONRR' radical where R and R' are independently hydrogen or alkyl, e.g., —CONH$_2$, methylaminocarbonyl, dimethylaminocarbonyl, and the like.

"Alkylamino" or "dialkylamino" refers to a —NHR and —NRR' radical respectively, where R and R' are independently alkyl group as defined above e.g., methylamino, dimethylamino, and the like.

"Acyl" means a —COR radical where R is alkyl, haloalkyl, aryl, heteroaryl, or heterocycloalkyl as defined herein e.g., acetyl, trifluoroacetyl, and the like. When R is alkyl it is referred to herein as alkylcarbonyl.

"Animal" includes humans, non-human mammals (e.g., dogs, cats, rabbits, cattle, horses, sheep, goats, swine, deer, and the like) and non-mammals (e.g., birds, and the like).

"Aromatic" refers to a moiety wherein the constituent atoms make up an unsaturated ring system, all atoms in the ring system are sp$^2$ hybridized and the total number of pi electrons is equal to 4n+2.

"Aryl" refers to a monocyclic or fused bicyclic ring assembly containing 6 to 10 ring carbon atoms wherein each ring is aromatic e.g., phenyl or naphthyl.

"Aralkyl" refers to a -(alkylene)-aryl radical where alkylene and aryl are as defined above, e.g., benzyl, 2-phenylethyl, and the like.

"Biologic" means a therapeutic agent originally derived from living organisms for the treatment or management of a disease. Examples include, but are not limited to, proteins (recombinant and plasma derived), monoclonal or polyclonal, humanized or murine antibodies, toxins, hormones, and the like. Biologics are currently available for the treatment of a variety of diseases such as cancer, rheumatoid arthritis, and hemophilia.

"Carboxy" refers to —C(O)OH radical.

"Cycloalkyl" refers to a monovalent saturated monocyclic ring containing three to eight ring carbon atoms e.g., cyclopropyl, cyclobutyl, cyclopentyl, cyclohexyl, and the like.

"Cycloalkylalkyl" refers to a -(alkylene)-R radical where R is cycloalkyl as defined above e.g., cyclopropylmethyl, cyclobutylethyl, cyclobutylmethyl, and the like "Cycloalkylene" refers to a divalent saturated monocyclic ring containing three to eight ring carbon atoms. For example, the instance wherein "R$^1$ and R$^2$ together with the carbon atom to which both R$^1$ and R$^2$ are attached form cycloalkylene" includes, but is not limited to, the following:

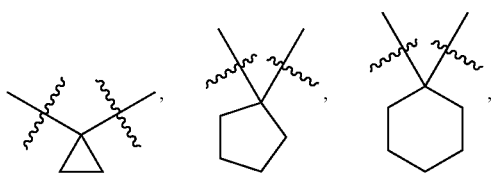

and the like.

"Derived" means a similar agent can be traced to.

"Disease" specifically includes any unhealthy condition of an animal or part thereof and includes an unhealthy condition that may be caused by, or incident to, medical or veterinary therapy applied to that animal, i.e., the "side effects" of such therapy.

"Deleterious immune response" means an immune response that prevents effective treatment of a patient or causes disease in a patient. As an example, dosing a patient with a murine antibody either as a therapy or a diagnostic agent causes the production of human antimouse antibodies that prevent or interfere with subsequent treatments. The incidence of antibody formation versus pure murine monoclonals can exceed 70%. (see Khazaeli, M. B. et al. *J. Immunother.* 1994, 15, pp 42-52; Dillman R. O. et al. *Cancer Biother.* 1994, 9, pp 17-28; and Reinsberg, J. *Hybridoma.* 1995, 14, pp 205-208). Additional examples of known agents that suffer from deleterious immune responses are blood-clotting factors such as factor VIII. When administered to hemophilia A patients, factor VIII restores the ability of the blood to clot. Although factor VIII is a human protein, it still elicits an immune response in hemophiliacs as endogenous factor VIII is not present in their blood and thus it appears as a foreign antigen to the immune system. Approximately 29-33% of new patients will produce antibodies that bind and neutralize the therapeutically administered factor VIII (see Lusher J. M. *Semin Thromb Hemost.* 2002, 28(3), pp 273-276). These neutralizing antibodies require the administration of larger amounts of factor VIII in order to maintain normal blood clotting parameters; an expensive regimen of treatment in order to induce immune tolerance (see Briet E et al. *Adv. Exp. Med. Bio.* 2001, 489, pp 89-97). Another immunogenic example is adenoviral vectors. Retroviral therapy remains experimental and is of limited utility. One reason is that the application of a therapeutic virus generates an immune response capable of blocking any subsequent administration of the same or similar virus (see Yiping Yang et al. *J. of Virology.* 1995, 69, pp 2004-2015). This ensures that retroviral therapies must be based on the transient expression of a protein or the direct incorporation of viral sequence into the host genome. Directed research has identified multiple viral neutralizing epitopes recognized by host antibodies (see Hanne, Gahery-Segard et al. *J. of Virology* 1998. 72, pp 2388-2397) suggesting that viral modifications will not be sufficient to overcome this obstacle. This invention will enable a process whereby an adenoviral therapy will have utility for repeated application. Another example of an immunogenic agent that elicits neutralizing antibodies is the well-known cosmetic agent Botox. Botulin toxin protein, is purified from the fermentation of *Clostridium botulinum*. As a therapeutic agent, it is used for muscle disorders such as cervical dystonia in addition to cosmetic application. After repeated exposure patients generate neutralizing antibodies to the toxin that results in reduced efficacy (see Birklein F. et al. *Ann Neurol.* 2002, 52, pp 68-73 and Rollnik, J. D. et al. *Neurol. Clin. Neurophysiol.* 2001, 2001(3), pp 2-4). A "deleterious immune response" also encompasses diseases caused by therapeutic agents. A specific example of this is the immune response to therapy with recombinant human erythropoietin (EPO). Erythropoietin is used to stimulate the growth or red cells and restore red blood cell counts in patients who have undergone chemotherapy or dialysis. A small percentage of patients develop antibodies to EPO and subsequently are unresponsive to both therapeutically administered EPO and their own endogenous EPO (see Casadevall, N. et al., *NEJM.* 2002, 346, pp 469-475). They contract a disorder, pure red cell aplasia, in which red blood cell production is severely diminished (see Gershon S. K. et. al. *NEJM.* 2002, 346, pp 1584-1586). This complication of EPO therapy is lethal if untreated. Another specific example is the murine antibody, OKT3 (a.k.a., Orthoclone) a monoclonal antibody directed towards CD-3 domain of activated T-cells. In clinical trials 20-40% of patients administered OKT3 produce antibodies versus the therapy.

These antibodies, besides neutralizing the therapy, also stimulate a strong host immune reaction. The immune reaction is severe enough that patients with high titers of human anti-mouse antibodies are specifically restricted from taking the drug (see Orthoclone package label). A final example is a human antibody therapeutic. Humira® is a monoclonal antibody directed against TNF and is used to treat rheumatoid arthritis patients. When taken alone ~12% of patients develop neutralizing antibodies. In addition, a small percentage of patients given the drug also contract a systemic lupus erthematosus-like condition that is an IgG-mediated immune response induced by the therapeutic agent (see Humira package label).

Another example of "deleterious immune response" is a host reaction to small molecule drugs. It is known to those skilled in the art that certain chemical structures will conjugate with host proteins to stimulate immune recognition (see Ju. C. et al. 2002. Current Drug Metabolism 3, pp 367-377 and Kimber I. et al. 2002, Toxicologic Pathology 30, pp 54-58.) A substantial portion of these host reactions are IgG mediated. Specific "deleterious immune responses" that are IgG mediated include: hemolytic anemia, Steven-Johnson syndrome and drug induced Lupus.

"Halo" refers to fluoro, chloro, bromo or iodo.

"Haloalkyl" refers to alkyl as defined above substituted by one or more, preferably one to seven, "halo" atoms, as such terms are defined in this Application. Haloalkyl includes monohaloalkyl, dihaloalkyl, trihaloalkyl, perhaloalkyl and the like e.g. chloromethyl, dichloromethyl, difluoromethyl, trifluoromethyl, 2,2,2-trifluoroethyl, perfluoroethyl, 2,2,2-trifluoro-1,1-dichloroethyl, and the like).

"Haloalkylene" means alkylene radical as defined above wherein one to four, preferably one or two hydrogen atoms in the alkylene chain has(have) been replaced by fluorine atom(s).

"Haloalkoxy" refers to a —OR radical where R is haloalkyl group as defined above e.g., trifluoromethoxy, 2,2,2-trifluoroethoxy, difluoromethoxy, and the like.

"Heteroaryl" as a group or part of a group denotes an aromatic monocyclic, bicyclic, or multicyclic moiety of 5 to 10 ring atoms in which one or more, preferably one, two, or three, of the ring atom(s) is(are) selected from nitrogen, oxygen or sulfur, the remaining ring atoms being carbon. Representative heteroaryl rings include, but are not limited to, pyrrolyl, furanyl, thienyl, oxazolyl, isoxazolyl, thiazolyl, imidazolyl, triazolyl, tetrazolyl, pyridinyl, pyrimidinyl, pyrazinyl, pyridazinyl, indolyl, benzofuranyl, benzothiophenyl, benzimidazolyl, quinolinyl, isoquinolinyl, quinazolinyl, quinoxalinyl, pyrazolyl, and the like.

"Heteroaralkyl" refers to a -(alkylene)-heteroaryl radical where alkylene and heteroaryl are as defined above, e.g., pyridinylmethyl, pyridinylethyl, pyrimidinylmethyl, and the like.

"Heterocycloalkyl" refers to a saturated or partially unsaturated, monocyclic or bicyclic moiety of 4, 5 or 6 carbon ring atoms wherein one or more, preferably one, two, or three of the carbon ring atoms are replaced by a heteroatom selected from —N═, —N—, —O—, —S—, —SO—, or —S(O)$_2$— and further wherein one or two ring atoms are optionally replaced by a keto (—CO—) group. The heterocycloalkyl ring is optionally fused to cycloalkyl, aryl or heteroaryl ring as defined herein. Representative examples include, but are not limited to, 4-oxo-5-aza-benzospiro[2.4]hept-5-yl, imidazolidinyl, morpholinyl, thiomorpholinyl, thiomorpholino-1-oxide, thiomorpholino-1,1-dioxide, tetrahydrofuranyl, tetrahydropyranyl, tetrahydrothiopyranyl, 1-oxo-tetrahydrothiopyranyl, 1,1-dioxotetrathiopyranyl, indolinyl, piperazinyl, piperidyl, pyrrolidinyl, pyrrolinyl, and the like.

"Heterocycloalkylalkyl" refers to a -(alkylene)-R radical where R is heterocycloalkyl as defined above e.g., pyrrolidinylmethyl, tetrahydrofuranylethyl, pyridinylmethyl, and the like.

"Hydroxy" means —OH radical. Unless indicated otherwise, the compounds of the invention containing hydroxy radicals include protected derivatives thereof. Suitable protecting groups for hydroxy moieties include benzyl and the like.

"Hydroxyalkyl" refers to alkyl as defined above substituted by one or more, preferably one to three hydroxyl groups e.g., hydroxymethyl, hydroxyethyl, and the like.

"Isomers" mean compounds of Formula (I) having identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes "optical isomers". A carbon atom bonded to four nonidentical substituents is termed a "chiral center". A compound with one chiral center that has two enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992). It is understood that the names and illustration used in this Application to describe compounds of Formula (I) are meant to be encompassed all possible stereoisomers.

"Optional" or "optionally" or "may be" means that the subsequently described event or circumstance may or may not occur, and that the description includes instances where the event or circumstance occurs and instances in which it does not. For example, the phrase "wherein the aromatic ring in $R^a$ is optionally substituted with one or two substituents independently selected from alkyl" means that the aromatic ring may or may not be substituted with alkyl in order to fall within the scope of the invention.

The present invention also includes N-oxide derivatives of a compound of Formula (I). N-oxide derivative mean a compound of Formula (I) in which a nitrogen atom is in an oxidized state (i.e., N→O) e.g., pyridine N-oxide, and which possess the desired pharmacological activity.

"Pathology" of a disease means the essential nature, causes and development of the disease as well as the structural and functional changes that result from the disease processes.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of Formula (I) which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methylsulfonic acid, ethanesulfonic acid, 1,2-ethanedisulfonic acid, 2-hydroxy-ethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

The present invention also includes prodrugs of a compound of Formula (I). Prodrug means a compound that is convertible in vivo by metabolic means (e.g. by hydrolysis) to a compound of Formula (I). For example an ester of a compound of Formula (I) containing a hydroxy group may be convertible by hydrolysis in vivo to the parent molecule. Alternatively an ester of a compound of Formula (I) containing a carboxy group may be convertible by hydrolysis in vivo to the parent molecule. Suitable esters of compounds of Formula (I) containing a hydroxy group, are for example acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methylsulphonates, ethanesulphonates, benzenesulphonates, p-toluenesulphonates, cyclohexylsulphamates and quinates. Suitable esters of compounds of Formula (I) containing a carboxy group, are for example those described by Leinweber, F. J. *Drug Metab. Res.*, 1987, 18, page 379. An especially useful class of esters of compounds of Formula (I) containing a hydroxy group, may be formed from acid moieties selected from those described by Bundgaard et al., *J. Med. Chem.*, 1989, 32, pp 2503-2507, and include substituted (aminomethyl)-benzoates, for example, dialkylamino-methylbenzoates in which the two alkyl groups may be joined together and/or interrupted by an oxygen atom or by an optionally substituted nitrogen atom, e.g. an alkylated nitrogen atom, more especially (morpholino-methyl) benzoates, e.g. 3- or 4-(morpholinomethyl)-benzoates, and (4-alkylpiperazin-1-yl)benzoates, e.g. 3- or 4-(4-alkylpiperazin-1-yl)benzoates.

"Protected derivatives" means derivatives of compounds of Formula (I) in which a reactive site or sites are blocked with protecting groups. Protected derivatives of compounds of Formula (I) are useful in the preparation of compounds of Formula (I) or in themselves may be active cathepsin S inhibitors. A comprehensive list of suitable protecting groups can be found in T. W. Greene, *Protective Groups in Organic Synthesis*, 3rd edition, John Wiley & Sons, Inc. 1999.

"Therapeutically effective amount" means that amount which, when administered to an animal for treating a disease, is sufficient to effect such treatment for the disease.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

"Treatment" or "treating" with respect to combination therapy i.e., use with a biologic means any administration of a compound of the present invention and includes:

(1) preventing the immune response from occurring in an animal which may be predisposed to the immune response but does not yet experience or display the pathology or symptomatology of the immune response, (2) inhibiting the immune response in an animal that is experiencing or displaying the pathology or symptomatology of the immune response (i.e., arresting further development of the pathology and/or symptomatology), or (3) ameliorating the immune response in an animal that is experiencing or displaying the pathology or symptomatology of the immune response (i.e., reducing in degree or severity, or extent or duration, the overt manifestations of the immune response or reversing the pathology and/or symptomatology e.g., reduced binding and presentation of antigenic peptides by MHC class II molecules, reduced activation of T-cells and B-cells, reduced humoral and cell-mediated responses and, as appropriate to the particular immune response, reduced inflammation, congestion, pain, necrosis, reduced loss in the efficacy of a biologic agent, and the like).

The expression " . . . wherein the aromatic or alicyclic ring in $R^3$ is optionally substituted with one, two, or three $R^a$ independently selected from alkyl, haloalkyl, alkoxy, hydroxy, haloalkoxy, halo, nitro, cyano, carboxy, alkoxycarbonyl, aryl, heteroaryl, amino, alkylamino, dialkylamino, or acyl . . . " includes instances where the aromatic or alicyclic ring is directly linked to $R^3$ or where the aromatic or alicyclic ring is part of a group that is directly linked to $R^3$ e.g., the alicyclic and aromatic ring in -alkylene-$SO_2$-cycloalkylalkyl, -alkylene-$SO_2$-aralkyl, -alkylene-$SO_2$-heterocycloalkylalkyl, -alkylene-$SO_2$-heteroaralkyl, or -alkylene-$SO_2$-haloalkylene-heteroaryl groups that are attached to $R^3$ may or may not be substituted with $R^a$ group(s).

Preferred Embodiments

I. Certain compounds of Formula (I) within the broadest scope set forth in the Summary of the Invention are preferred. For example:

A. One preferred group of compounds is that wherein $R^1$ and $R^2$ are hydrogen.

B. Another preferred group of compounds is that wherein $R^1$ and $R^2$ together with the carbon atom to which they are attached form cycloalkylene, preferably $R^1$ and $R^2$ together with the carbon atom to which they are attached form cyclopropylene.

C. Another preferred group of compounds is that wherein $R^1$ and $R^2$ together with the carbon atom to which they are attached form tetrahydropyran-4-yl, tetrahydrothiopyran-4-yl, or 1,1-dioxohexahydrothiopyran-4-yl.

(a) Within the above preferred groups A, B, and C and the more preferred groups contained therein, a more preferred group of compounds is that wherein:

$R^3$ is -alkylene-$SO_2$— heteroaralkyl, preferably the heteroaryl ring in the heteroalkyl moiety is pyridinyl, pyrazinyl, pyridazinyl, pyrimidinyl, quinolinyl, or isoquinolinyl and wherein the heteroaryl ring is optionally substituted with one, two, or three $R^a$ independently selected from alkyl, haloalkyl, alkoxy, hydroxy, haloalkoxy, halo, nitro, cyano, carboxy, alkoxycarbonyl, aryl, heteroaryl, amino, alkylamino, dialkylamino, or acyl and further wherein the aromatic ring in $R^a$ is optionally substituted with one, two, or three $R^b$ independently selected from alkyl, alkoxy, hydroxyl, or halo. Preferably, $R^3$ is 4-$CF_3$-pyridin-3-ylmethane-sulfonylmethyl, pyridin-3-ylmethanesulfonylmethyl, pyridazin-3-ylmethanesulfonylmethyl, 2-$CF_3$-furan-5-ylmethanesulfonylmethyl, pyrimidin-5-ylmethanesulfonylmethyl, 2-$CH_3$-thiazol-4-ylmethanesulfonylmethyl, or pyridin-4-ylmethane-sulfonylmethyl.

(b) Within the above preferred groups A, B, and C and the more preferred groups contained therein, another even more preferred group of compounds is that wherein:

$R^3$ is -alkylene-$SO_2$—$CF_2$-heteroaryl, preferably the heteroaryl ring in the heteroaralkyl moiety is pyridinyl, pyrazinyl, pyridazinyl, pyrimidinyl, quinolinyl, or isoquinolinyl and wherein the heteroaryl ring is optionally substituted with one, two, or three $R^a$ independently selected from alkyl, halo alkyl, alkoxy, hydroxy, halo alkoxy, halo, nitro, cyano, carboxy, alkoxycarbonyl, aryl, heteroaryl, amino, alkylamino, dialkylamino, or acyl and further wherein the aromatic ring in $R^a$ is optionally substituted with one, two, or three $R^b$ independently selected from alkyl, alkoxy, hydroxyl, or halo. Preferably, $R^3$ is 4-$CF_3$-pyridin-3-yl-$CF_2SO_2$-methyl, pyridin-3-yl-$CF_2SO_2$-methyl, pyridazin-3-yl-$CF_2SO_2$-methyl, pyrimidin-5-yl-$CF_2SO_2$-methyl, or pyridin-4-yl-$CF_2SO_2$-methyl.

Within the above preferred groups A, A(a-b), B, B(a-b), C, and C(a-b) and the more preferred groups contained therein, a particularly preferred group of compounds is that wherein:

$R^4$ is phenyl optionally substituted with one or two fluoro. Preferably, $R^4$ is 4-fluorophenyl, 2,4-difluorophenyl, or 3,4-difluorophenyl;

and the stereochemistry at the carbon to which $R^3$ is attached is (R) and to which $R^4$ is attached is (S).

(D) Another preferred group of compounds is that wherein:
$R^1$ and $R^2$ form cyclopropylene;
$R^3$ is 4-$CF_3$-pyridin-3-ylmethanesulfonylmethyl, pyridin-3-ylmethanesulfonylmethyl, pyridazin-3-ylmethanesulfonylmethyl, 2-$CF_3$-furan-5-ylmethanesulfonylmethyl, pyrimidin-5-ylmethanesulfonylmethyl, 2-$CH_3$-thiazol-4-ylmethanesulfonylmethyl, pyridin-4-ylmethanesulfonylmethyl, pyrimidin-4-ylmethanesulfonylmethyl, 2-(1-oxopyrrol-1-yl)ethanesulfonyl-methyl, cyclopropylmethanesulfonylmethyl, 3,3,3-trifluoropropane-1-sulfonylmethyl, 2-$CF_3$-pyridin-5-ylmethanesulfonylmethyl, 4-[1.2.4]-triazol-1-ylphenylmethanesulfonylmethyl, 2-(2-oxo-2,3-dihydrobenzimidazol-1-yl)-ethanesulfonylmethyl, 5-oxopyrrolidin-2-ylmethanesulfonylmethyl, 2-F-pyridin-3-ylmethanesulfonylmethyl, 3-$CH_3$-oxetan-3-ylmethanesulfonylmethyl, 2-phenylethanesulfonylmethyl, fluoro-pyridin-2-ylmethanesulfonylmethyl, fluoro-pyrazin-2-ylmethanesulfonylmethyl, difluoro-pyridin-2-ylmethanesulfonylmethyl, difluoro-pyridin-3-ylmethanesulfonylmethyl, quinolin-2-ylmethanesulfonylmethyl, benzo[1.2.5]thiadiazol-4-ylmethanesulfonylmethyl, benzothiazol-2-ylmethanesulfonylmethyl, 5-methylisoxazol-3-ylmethanesulfonylmethyl, 2-methylpropylsulfonylmethyl, 2,6-difluorophenylmethanesulfonylmethyl, 2,4-difluorophenylmethanesulfonylmethyl, quinolin-3-ylmethanesulfonylmethyl, 4,4,4-trifluorobutyl-1-sulfonylmethyl, 2-$CF_3$-phenylmethanesulfonylmethyl, 2-$CF_3O$-phenylmethanesulfonylmethyl, 2-pyridin-2-ylethanesulfonylmethyl, 2-pyridin-3-ylethanesulfonylmethyl, quinolin-8-ylmethanesulfonylmethyl, 5-methyl-3-phenylisoxazol-4-ylmethanesulfonylmethyl, 4-methyl-2-phenyl-[1.2.3]triazol-5-ylmethanesulfonylmethyl, 2-cyanophenylmethanesulfonylmethyl, 3-methoxycarbonylphenylmethanesulfonylmethyl, pyridin-2-ylmethanesulfonylmethyl, 1-oxopyridin-2-ylmethanesulfonylmethyl, 1-oxopyridin-3-ylmethanesulfonylmethyl, quinoxalin-2-ylmethanesulfonylmethyl, tetrahydropyran-2RS-ylmethanesulfonylmethyl, 2,6-dichlorophenylmethanesulfonylmethyl, 3-methoxycarbonyl-furan-2-ylmethanesulfonylmethyl, 5-methylisoxazol-3-ylmethanesulfonylmethyl, 2,2-dimethylpropylsulfonylmethyl, ethanesulfonylmethyl, methanesulfonylmethyl, propane-1-sulfonylmethyl, 1H-indol-2-ylmethanesulfonylmethyl, 2-(1H-indol-3-yl)ethanesulfonylmethyl, 2,2,2-trifluoroethanesulfonylmethyl, benzisoxazol-3-ylmethanesulfonylmethyl, 2-tert-butyl-[1.3.4]thiadiazol-5-ylmethanesulfonylmethyl, 2,4,6-trifluorophenylmethanesulfonylmethyl, 2-pyridin-2-ylethanesulfonylmethyl, 1-ethyl-2,5-dioxopyrrolidin-3-ylmethanesulfonylmethyl or benzisoxazol-3-ylmethanesulfonylmethyl;

$R^4$ is 4-fluorophenyl, 2,3-difluorophenyl, 2,4-difluorophenyl, 2,5-difluorophenyl, or 3,5-difluorophenyl, more preferably 2,4-difluorophenyl;

$R^{4'}$ is difluoromethyl, trifluoromethyl, or 1,1,2,2,2-pentafluoroethyl, more preferably trifluoromethyl.

(D) Another preferred group of compounds is that wherein:
$R^1$ and $R^2$ form cyclopropylene;
$R^3$ is 4-$CF_3$-pyridin-3-ylmethanesulfonylmethyl, pyridin-3-ylmethanesulfonylmethyl, pyridazin-3-ylmethanesulfonylmethyl, 2-$CF_3$-furan-5-ylmethanesulfonylmethyl, pyrimidin-5-ylmethanesulfonylmethyl, 2-$CH_3$-thiazol-4-ylmethanesulfonylmethyl, pyridin-4-ylmethanesulfonylmethyl, pyrimidin-4-ylmethanesulfonylmethyl, 2-(1-oxopyrrol-1-yl)ethanesulfonyl-methyl, cyclopropylmethanesulfonylmethyl, 3,3,3-trifluoropropane-1-sulfonylmethyl, 2-$CF_3$-pyridin-5-ylmethanesulfonylmethyl, 4-[1.2.4]-triazol-1-ylphenylmethanesulfonylmethyl, 2-(2-oxo-2,3-dihydrobenzimidazol-1-yl)-ethanesulfonylmethyl, 5-oxopyrrolidin-2-ylmethanesulfonylmethyl, 2-F-pyridin-3-ylmethanesulfonylmethyl, 3-$CH_3$-oxetan-3-ylmethanesulfonylmethyl, 2-phenylethanesulfonylmethyl, fluoro-pyridin-2-ylmethanesulfonylmethyl, fluoro-pyrazin-2-ylmethanesulfonylmethyl, difluoro-pyridin-2-ylmethanesulfonylmethyl, difluoro-pyridin-3-ylmethanesulfonylmethyl, quinolin-2-ylmethanesulfonylmethyl, benzo[1.2.5]thiadiazol-4-ylmethanesulfonylmethyl, benzothiazol-2-ylmethanesulfonylmethyl, 5-methylisoxazol-3-ylmethanesulfonylmethyl, 2-methylpropylsulfonylmethyl, 2,6-difluorophenylmethanesulfonylmethyl, 2,4-difluorophenylmethanesulfonylmethyl, quinolin-3-ylmethanesulfonylmethyl, 4,4,4-trifluorobutyl-1-sulfonylmethyl, 2-$CF_3$-phenylmethanesulfonylmethyl, 2-$CF_3O$- phenylmethanesulfonylmethyl, 2-pyridin-2-ylethanesulfonylmethyl, 2-pyridin-3-ylethanesulfonylmethyl, quinolin-8-ylmethanesulfonylmethyl, 5-methyl-3-phenylisoxazol-4-ylmethanesulfonylmethyl, 4-methyl-2-phenyl-[1.2.3]triazol-5-ylmethanesulfonylmethyl, 2-cyanophenylmethanesulfonylmethyl, 3-methoxycarbonylphenylmethanesulfonylmethyl, pyridin-2-ylmethanesulfonylmethyl, 1-oxopyridin-2-ylmethanesulfonylmethyl, 1-oxopyridin-3-ylmethanesulfonylmethyl, quinoxalin-2-ylmethanesulfonylmethyl, tetrahydropyran-2RS-ylmethanesulfonylmethyl, 2,6-dichlorophenylmethanesulfonylmethyl, 3-methoxycarbonyl-furan-2-ylmethanesulfonylmethyl, 5-methylisoxazol-3-ylmethanesulfonylmethyl, 2,2-dimethylpropylsulfonylmethyl, ethanesulfonylmethyl, methanesulfonylmethyl, propane-1-sulfonylmethyl, 1H-indol-2-ylmethanesulfonylmethyl, 2-(1H-indol-3-yl)ethanesulfonylmethyl, 2,2,2-trifluoroethanesulfonylmethyl, benzisoxazol-3-ylmethanesulfonylmethyl, 2-tert-butyl-[1.3.4]thiadiazol-5-ylmethanesulfonylmethyl, 2,4,6-trifluorophenylmethanesulfonylmethyl, 2-pyridin-2-ylethanesulfonylmethyl, 1-ethyl-2,5-dioxopyrrolidin-3-ylmethanesulfonylmethyl or benzisoxazol-3-ylmethanesulfonylmethyl;

$R^4$ is hydrogen;

$R^{4'}$ is difluoromethyl, trifluoromethyl, or 1,1,2,2,2-pentafluoroethyl, more preferably trifluoromethyl.

(F) Yet another preferred group of compounds is that wherein $R^3$ is -alkylene-SO$_2$-haloalkylene-heteroaryl, more preferably -alkylene-SO$_2$—CF$_2$-heteroaryl.

Within this preferred group a more preferred group is that wherein $R^1$ and $R^2$ are cyclopropylene.

(G) Yet another preferred group of compounds is that wherein:

$R^3$ is 3,5-dimethylisoxazol-4-ylmethanesulfonylmethyl; 2-CF$_3$-methylphenylmethane-sulfonylmethyl, 3-CF$_3$pyridin-2-ylmethanesulfonylmethyl, 2-F-furan-5-ylmethanesulfonyl-methyl, 2-methylthiazol-4-ylmethanesulfonylmethyl, tetrahydropyran-4-ylmethane-sulfonylmethyl, 1,1-dioxo-1λ$^6$-hexahydrothiopyran-4-ylmethanesulfonylmethyl, 1-ethylpiperidin-4-ylmethanesulfonylmethyl, 2-oxo-tetrahydropyrimidin-4-ylmethane-sulfonylmethyl, 1-ethyl-2-oxopiperidin-4-ylmethanesulfonylmethyl, 1-acetylpiperidin-4-ylmethanesulfonylmethyl, 1-ethoxycarbonylpiperidin-4-ylmethanesulfonylmethyl, 1-methylsulfonylpiperidin-4-ylmethanesulfonylmethyl, 1-cyclopropylpiperidin-4-ylmethane-sulfonylmethyl, 1-acetylazetidin-3-ylmethanesulfonylmethyl, 1-ethoxycarbonylazetidin-3-ylmethanesulfonylmethyl, 1-methylsulfonylazetidin-3-ylmethanesulfonylmethyl, 1-ethyl azetidin-3-ylmethanesulfonylmethyl, 1-cyclopropylazetidin-3-ylmethanesulfonylmethyl furan-2-ylmethanesulfonylmethyl, difluoro-(4-fluorophenyl) methanesulfonylmethyl, difluoro-(pyrazin-2-yl) methanesulfonylmethyl, difluoro-(2-difluoromethoxyphenyl)-methanesulfonylmethyl, 1-acetylpiperidin-4-ylsulfonylmethyl, 1-ethoxycarbonylpiperidin-4-ylsulfonylmethyl, 1-cyclopropylpiperidin-4-ylsulfonylmethyl, 2-(pyridin-2-yl)ethanesulfonyl-methyl, 2-(pyridin-3-yl)ethanesulfonylmethyl, 2-(pyridin-4-yl) ethanesulfonylmethyl, 3-(pyridin-2-yl) propanesulfonylmethyl, 2,6-difluorophenylmethanesulfonyl, [1.3.5]triazin-2-ylmethanesulfonylmethyl, [1.3.4]thiadiazol-2-ylmethanesulfonylmethyl, oxazol-5-ylmethanesulfonylmethyl, thiazol-5-ylmethanesulfonylmethyl, 4-fluorophenylmethanesulfonylmethyl, 4-aminocarbonylphenyl-methanesulfonylmethyl, 4-piperazin-4-ylphenylmethanesulfonylmethyl, 5-fluoroindol-3-ylmethanesulfonylmethyl, 4,6-difluoroindol-3-ylmethanesulfonylmethyl, 1-methylindol-3-ylmethanesulfonylmethyl, 4-fluoroindol-3-ylmethanesulfonylmethyl, 2-(5-fluoroindol-3-yl)ethanesulfonylmethyl, 2-(4,6-difluoroindol-3-yl) ethanesulfonylmethyl, 2-(1-methylindol-3-yl) ethanesulfonylmethyl, 2-(4-fluoroindol-3-yl) ethanesulfonylmethyl, 2-quinolin-3-ylmethanesulfonylmethyl, 2-quinolin-2-ylethanesulfonylmethyl, isoquinolin-3-ylmethanesulfonylmethyl, 2-(isoquinolin-3-yl)ethanesulfonylmethyl, 2,4-difluoropyridin-3-ylmethane-sulfonylmethyl, 3,4-difluoropyridin-4-ylmethanesulfonylmethyl, 2-(2,4-difluoropyridin-3-yl)ethanesulfonylmethyl, 2-(3,4-difluoropyridin-4-yl)ethanesulfonylmethyl, fluoro-(2,4-difluoropyridin-3-yl)methanesulfonylmethyl, fluoro-(3,4-difluoropyridin-4-yl)methane-sulfonylmethyl, 2,4-diCF$_3$pyridin-3-ylmethanesulfonylmethyl, 3,4-diCF$_3$pyridin-4-ylmethane-sulfonylmethyl, 2-(2,4-diCF$_3$pyridin-3-yl) ethanesulfonylmethyl, 2-(3,4-diCF$_3$pyridin-4-yl) ethanesulfonylmethyl, fluoro-(2,4-diCF$_3$pyridin-3-yl) methanesulfonylmethyl, fluoro-(3,4-diCF$_3$pyridin-4-yl) methanesulfonylmethyl, 4-F-pyridin-3-ylmethanesulfonylmethyl, 3-P-pyridin-5-ylmethanesulfonylmethyl, 2-F-pyridin-5-ylmethanesulfonylmethyl, 2-F-pyridin-3-ylmethanesulfonylmethyl, 5-F-pyridin-2-ylmethanesulfonylmethyl, 4-F-pyridin-2-ylmethane-sulfonylmethyl, 4-F-1-oxopyridin-3-ylmethanesulfonylmethyl, 3-F-1-oxopyridin-5-ylmethane-sulfonylmethyl, 2-F-1-oxopyridin-5-ylmethanesulfonylmethyl, 2-F-1-oxopyridin-3-ylmethane-sulfonylmethyl, 5-F-1-oxopyridin-2-ylmethanesulfonylmethyl, 4-F-1-oxopyridin-2-ylmethane-sulfonylmethyl, 4-CF$_3$-pyridin-2-ylmethanesulfonylmethyl, 3-CF$_3$-pyridin-5-ylmethane-sulfonylmethyl, 3-F-pyridin-2-ylmethanesulfonylmethyl, 2-CF$_3$-pyridin-3-ylmethane-sulfonylmethyl, 4-CF$_3$-1-oxopyridin-2-ylmethanesulfonylmethyl, 3-CF$_3$-1-oxopyridin-5-ylmethanesulfonylmethyl, 3-F-1-oxopyridin-2-ylmethanesulfonylmethyl, 2-CF$_3$-1-oxopyridin-3-ylmethanesulfonylmethyl, 5-CF$_3$-1-oxopyridin-2-ylmethanesulfonylmethyl, 2-CH$_3$-pyridin-6-ylmethanesulfonylmethyl, 3-CH$_3$-pyridin-2-ylmethanesulfonylmethyl, 4-CH$_3$-pyridin-3-ylmethanesulfonylmethyl, 3-CH$_3$-pyridin-4-ylmethanesulfonylmethyl, 2-(2-CH$_3$-pyridin-6-yl) ethanesulfonylmethyl, 2-(3-CF$_3$-pyridin-2-yl) ethanesulfonylmethyl, 2-(4-CF$_3$-pyridin-3-yl) ethanesulfonylmethyl, 2-(3-CF$_3$-pyridin-4-yl) ethanesulfonylmethyl, 2-C$_2$H$_5$-pyridin-6-ylmethanesulfonylmethyl, 3-C$_2$H$_5$-pyridin-2-ylmethanesulfonylmethyl, 4-C$_2$H$_5$-pyridin-3-ylmethanesulfonylmethyl, 3-C$_2$H$_5$-pyridin-4-ylmethanesulfonylmethyl, 2-(2-C$_2$H$_5$-pyridin-6-yl) ethanesulfonylmethyl, 2-(3-C$_2$H$_5$-pyridin-2-yl) ethanesulfonylmethyl, 2-(4-C$_2$H$_5$-pyridin-3-yl) ethanesulfonylmethyl, 2-(3-C$_2$H$_5$-pyridin-4-yl) ethanesulfonylmethyl, 2-(2-CH$_3$-pyridin-3-yl) ethanesulfonylmethyl, 2-CF$_3$-pyridin-3-ylmethanesulfonylmethyl, 2-(3-CF$_3$-pyridin-4-yl) ethanesulfonylmethyl, 3-CF$_3$-pyridin-4-ylmethanesulfonylmethyl, cinnolin-3-ylmethanesulfonylmethyl, 2-(cinnolin-3-yl)ethanesulfonylmethyl, phthalazin-1-ylmethanesulfonylmethyl, 2-phthalazin-1-ylethanesulfonylmethyl, 2-(quinoxalin-2-yl)ethanesulfonylmethyl, quinazolin-2-ylmethanesulfonylmethyl, 2-(quinazolin-2-yl)ethanesulfonylmethyl, [1,8]naphthyridin-2-ylmethanesulfonylmethyl, 2-([1,8]naphthyridin-2-yl)ethanesulfonylmethyl, [1,8]naphthyridin-3-ylmethanesulfonylmethyl, 2-([1,8]naphthyridin-3-yl)ethanesulfonylmethyl, 3-Cl-pyridin-2-ylmethanesulfonylmethyl, 4-Cl-pyridin-3-ylmethanesulfonylmethyl, 3-Cl-pyridin-4-ylmethanesulfonylmethyl, 3-F-pyridin-2-ylmethanesulfonylmethyl, 4-F-pyridin-3-ylmethanesulfonyl-methyl, 3-F-pyridin-4-ylmethanesulfonylmethyl, isoquinolin-4-ylmethanesulfonylmethyl, 6-phenylpyridin-2-ylmethanesulfonylmethyl, 3-phenylpyridin-2-ylmethanesulfonylmethyl, 4-phenylpyridin-3-ylmethanesulfonylmethyl, 3-phenylpyridin-4-ylmethanesulfonylmethyl, 2-(6-phenylpyridin-2-yl)ethanesulfonylmethyl, 2-(3-phenylpyridin-2-yl)ethanesulfonylmethyl, 2-(4-phenylpyridin-3-yl)ethanesulfonylmethyl, 2-(3-phenylpyridin-4-yl)ethanesulfonylmethyl, 6-(pyridin-2-yl)pyridin-2-ylmethanesulfonylmethyl, 3-(pyridin-2-yl)pyridin-2-ylmethanesulfonylmethyl, 4-(pyridin-2-yl)pyridin-3-ylmethanesulfonylmethyl, 3-(pyridin-2-yl)pyridin-4-ylmethanesulfonylmethyl, 2-[6-(pyridin-2-yl)pyridin-2-yl]ethanesulfonylmethyl, 2-[3-(pyridin-2-yl)pyridin-2-yl]ethanesulfonylmethyl, 2-[4-(pyridin-2-yl)pyridin-3-yl]ethanesulfonylmethyl, 2-[3-(pyridin-2-yl)pyridin-4-yl]ethanesulfonylmethyl, 6-(pyridin-3-yl)pyridin-2-ylmethanesulfonylmethyl, 3-(pyridin-3-yl)pyridin-2-ylmethanesulfonylmethyl, 4-(pyridin-3-yl)pyridin-3-ylmethanesulfonylmethyl, 3-(pyridin-3-yl)pyridin-4-ylmethanesulfonylmethyl, 2-[6-(pyridin-3-yl)pyridin-2-yl]ethanesulfonylmethyl, 2-[3-(pyridin-3-yl)pyridin-2-yl]ethanesulfonylmethyl, 2-[4-(pyridin-3-yl)pyridin-3-yl]ethanesulfonylmethyl, 2-[3-(pyridin-3-yl)pyridin-4-yl]ethanesulfonylmethyl, 6-(pyridin-4-yl)pyridin-2-ylmethanesulfonylmethyl, 3-(pyridin-4-yl)pyridin-2-ylmethanesulfonylmethyl, 4-(pyridin-4-yl)pyridin-3-ylmethanesulfonylmethyl, 3-(pyridin-4-yl)pyridin-4-ylmethanesulfonylmethyl, 2-[6-(pyridin-4-yl)pyridin-2-yl]-ethanesulfonylmethyl, 2-[3-(pyridin-4-yl)pyridin-2-yl]ethanesulfonylmethyl, 2-[4-(pyridin-4-yl)pyridin-3-yl]ethanesulfonylmethyl, 2-[3-(pyridin-4-yl)pyridin-4-yl]ethanesulfonylmethyl, 2,2-dimethylcyclopropylmethanesulfonylmethyl, biphen-2-ylmethanesulfonylmethyl, 2-thiophen-2-ylphenylmethanesulfonylmethyl, 2-thiazol-2-ylphenylmethanesulfonylmethyl, 2-thiazol-5-ylphenylmethanesulfonylmethyl, 2-[1.2.3]thiadiazol-5-ylphenylmethane-sulfonylmethyl, 2-isoxazol-5-ylphenylmethanesulfonylmethyl, 2-(1-methylpyrazol-5-yl)phenylmethanesulfonylmethyl, 2-[1.2.3]triazol-5-ylphenylmethanesulfonylmethyl, 2-[1.2.3]oxadiazol-5-ylphenylmethanesulfonylmethyl, 2-[(1.2.3)triazol-5-yl]phenylmethanesulfonylmethyl, 2-[(1.2.3)triazol-1-yl]phenylmethanesulfonylmethyl, oxazolo[5,4-b]pyridin-2-ylmethane-sulfonylmethyl, oxazolo[4,5-c]pyridin-2-ylmethanesulfonylmethyl, oxazolo[4,5-b]pyridin-2-ylmethanesulfonylmethyl, benzimidazol-5-ylmethanesulfonylmethyl, benzimidazol-4-ylmethanesulfonylmethyl, 3H-imidazo[4,5-b]pyridin-2-ylmethanesulfonylmethyl, 3H-imidazo[4,5-c]pyridin-2-ylmethanesulfonylmethyl, 3-CF$_3$-3H-imidazo[4,5-b]pyridin-2-ylmethanesulfonylmethyl, 3-CF$_3$3H-imidazo[4,5-c]pyridin-2-ylmethanesulfonylmethyl, 1-CF$_3$-1H-imidazo[4,5-c]pyridin-2-ylmethanesulfonylmethyl, 1-CF$_3$-1H-imidazo[4,5-b]pyridin-2-ylmethanesulfonylmethyl, thiazolo[5,4-b]pyridin-2-ylmethanesulfonylmethyl, thiazolo[4,5-c]pyridin-2-ylmethanesulfonylmethyl, thiazolo[4,5-b]pyridin-2-ylmethanesulfonylmethyl, 5-CF$_3$thiazolo[5,4-b]pyridin-2-ylmethanesulfonylmethyl, 4-CF$_3$-thiazolo[4,5-c]pyridin-2-ylmethanesulfonylmethyl, 7-CF$_3$-thiazolo[4,5-b]pyridin-2-ylmethanesulfonylmethyl, 3-CF$_3$-1H-pyrrolo[2,3-b]pyridin-2-ylmethanesulfonylmethyl, 3-CF$_3$-1H-pyrrolo[3,2-c]pyridin-2-ylmethanesulfonylmethyl, 3-CF$_3$-1H-pyrrolo[3,2-b]pyridin-2-ylmethanesulfonylmethyl, imidazo[1,2-c]pyrimidin-2-methanesulfonylmethyl, 8-CF$_3$-imidazo[1,2-c]pyrimidin-2-methanesulfonylmethyl, imidazo[1,2-a]pyrimidin-2-methanesulfonylmethyl, 8-CF$_3$-imidazo[1,2-b]pyridazin-2-ylmethanesulfonylmethyl, imidazo[1,2-a]pyrazin-2-methanesulfonylmethyl, 8-CF$_3$-imidazo[1,2-a]pyrazin-2-methanesulfonylmethyl, pyrazolo[1,5-c]pyrimidin-2-ylmethanesulfonylmethyl, 3-CF$_3$-pyrazolo[1,5-c]pyrimidin-2-ylmethanesulfonylmethyl, 4-CF$_3$-pyrazolo[1,5-c]pyrimidin-2-ylmethanesulfonylmethyl, imidazo[1,2-d][1,2,4]triazin-2-methanesulfonylmethyl, 3-CF$_3$-imidazo[1,2-d][1,2,4]triazin-2-methanesulfonylmethyl, [1,3]benzoxazol-2-ylmethanesulfonylmethyl, 5-F-[1,3]benzoxazol-2-ylmethanesulfonylmethyl [1,3]benzoxazol-4-ylmethanesulfonylmethyl, 2-CF$_3$-[1,3]benzoxazol-4-ylmethanesulfonyl-methyl, [1,3]benzoxazol-7-ylmethanesulfonylmethyl, 2-CF$_3$-[1,3]benzoxazol-7-ylmethane-sulfonylmethyl, [1,2]benzoxazol-3-ylmethanesulfonylmethyl, [1,2]benzoxazol-4-ylmethanesulfonylmethyl, 5-CF$_3$-[1,2]benzoxazol-4-ylmethanesulfonylmethyl, 3-CF$_3$-[1,2]benzoxazol-4-ylmethanesulfonylmethyl, 6-CF$_3$-[1,2]benzoxazol-7-ylmethane-sulfonylmethyl, 6-CN-[1,2]benzoxazol-7-ylmethanesulfonylmethyl, 3-CF$_3$-[1,2]benzoxazol-7-ylmethanesulfonylmethyl, 5-CF$_3$-[1,2]benzoxazol-3-ylmethanesulfonylmethyl, [2,3]benzoxazol-7-ylmethanesulfonylmethyl, 6-CF$_3$-[2,3]benzoxazol-7-ylmethanesulfonylmethyl, 1-CF$_3$-[2,3]benzoxazol-7-ylmethanesulfonylmethyl, 5-CF$_3$-[2,3]benzoxazol-4-ylmethanesulfonylmethyl, 5-CN-[2,3]benzoxazol-4-ylmethanesulfonylmethyl, 1-CF$_3$-[2,3]benzoxazol-4-ylmethanesulfonylmethyl, benzothiazol-2-ylmethanesulfonylmethyl, 5-F-benzothiazol-2-ylmethanesulfonylmethyl, benzothiazol-4-ylmethanesulfonylmethyl, 2-CF$_3$-benzothiazol-4-ylmethanesulfonylmethyl, benzothiazol-7-ylmethanesulfonylmethyl, 2-CF$_3$-benzothiazol-7-ylmethanesulfonylmethyl, [1,2]benzothiazol-3-ylmethanesulfonylmethyl, [1,2]benzothiazol-4-ylmethanesulfonylmethyl, 5-CF$_3$-[1,2]benzothiazol-4-ylmethanesulfonylmethyl, 3-CF$_3$-[1,2]benzothiazol-4-ylmethanesulfonylmethyl, 6-CF$_3$-[1,2]benzothiazol-7-ylmethanesulfonylmethyl, 6-CN-[1,2]benzothiazol-7-ylmethanesulfonylmethyl, 3-CF$_3$-[1,2]benzothiazol-7-ylmethanesulfonylmethyl, 5-F-[1,2]benzothiazol-3-ylmethanesulfonylmethyl, [2,3]benzothiazol-7-ylmethanesulfonylmethyl, 6-CF$_3$-[2,3]benzothiazol-7-ylmethane-sulfonylmethyl, 1-CF$_3$-[2,3]benzothiazol-7-ylmethanesulfonylmethyl, 5-CF$_3$-[2,3]benzothiazol-4-ylmethanesulfonylmethyl, 5-CN-[2,3]benzothiazol-4-ylmethanesulfonylmethyl, 1-CF$_3$-[2,3]benzothiazol-4-ylmethanesulfonylmethyl, 4-CF$_3$-2-CH$_3$-thiazol-5-ylmethanesulfonylmethyl, 4-CF$_3$-thiazol-5-ylmethanesulfonylmethyl, 4-CF$_3$-2-phenyl-thiazol-5-ylmethanesulfonylmethyl, 5-CF$_3$-2-CH$_3$-thiazol-4-ylmethanesulfonylmethyl, 5-CF$_3$-thiazol-4-ylmethanesulfonylmethyl, 5-CF$_3$-2-phenyl-thiazol-4-ylmethanesulfonylmethyl, 5-CH$_3$-thiazol-2- ylmethanesulfonylmethyl, 5-CF₃-thiazol-2-ylmethanesulfonylmethyl, 5-phenyl-thiazol-2-ylmethanesulfonylmethyl, 4-CH₃-thiazol-2-ylmethanesulfonyl-methyl, 4-CF₃-thiazol-2-ylmethanesulfonylmethyl, 4-phenyl-thiazol-2-ylmethanesulfonylmethyl, 5-CH₃-2-(pyridin-2-yl)-[1,2,3]triazol-4-ylmethanesulfonylmethyl, 5-CF₃-2-(pyridin-2-yl)-[1,2,3]triazol-4-ylmethanesulfonylmethyl, 5-CF₃-2-(4-methylsulfonylphenyl)-[1,2,3]triazol-4-ylmethane-sulfonylmethyl, 4,5-dimethyl-[1,2,4]triazol-3-ylmethanesulfonylmethyl, 5-CF₃-4-CH₃-[1,2,4]triazol-3-ylmethanesulfonylmethyl, 4-CH₃-5-phenyl-[1,2,4]triazol-3-ylmethane-sulfonylmethyl, 5-CF₃-4-cyclopropyl-[1,2,4]triazol-3-ylmethanesulfonylmethyl, 2,5-dimethyl-[1,2,4]triazol-3-ylmethanesulfonylmethyl, 5-CF₃-2-CH₃-[1,2,4]triazol-3-ylmethane-sulfonylmethyl, 2-CH₃-5-phenyl-[1,2,4]triazol-3-ylmethanesulfonylmethyl, 2-cyclopropyl-5-phenyl-[1,2,4]triazol-3-ylmethanesulfonylmethyl, 5-CF₃-1-CH₃-[1,2,4]triazol-3-ylmethane-sulfonylmethyl, 1-CH₃-5-phenyl-[1,2,4]triazol-3-ylmethanesulfonylmethyl, 5-CH₃-1-phenyl-[1,2,4]triazol-3-ylmethanesulfonylmethyl, 3-CH₃-[1,2,4]oxadiazol-5-ylmethanesulfonylmethyl 3-CF₃-[1,2,4]oxadiazol-5-ylmethanesulfonylmethyl, 3-phenyl-[1,2,4]oxadiazol-5-ylmethanesulfonylmethyl, 5-CH₃-[1,2,4]oxadiazol-3-ylmethanesulfonylmethyl, 5-CF₃-[1,2,4]oxadiazol-3-ylmethanesulfonylmethyl, 5-phenyl-[1,2,4]oxadiazol-3-ylmethanesulfonylmethyl, 2-CH₃-[1,3,4]oxadiazol-5-ylmethanesulfonylmethyl, 2-CF₃-[1,3,4]oxadiazol-5-ylmethanesulfonylmethyl, 2-phenyl-[1,3,4]oxadiazol-5-ylmethanesulfonylmethyl, 3-CH₃-[1,2,4]thiadiazol-5-ylmethanesulfonylmethyl, 3-CF₃-[1,2,4]thiadiazol-5-ylmethanesulfonylmethyl, 3-phenyl-[1,2,4]thiadiazol-5-ylmethanesulfonylmethyl, 5-CH₃-[1,2,4]thiadiazol-3-ylmethane-sulfonylmethyl, 5-CF₃-[1,2,4]thiadiazol-3-ylmethanesulfonylmethyl, 5-phenyl-[1,2,4]thiadiazol-3-ylmethanesulfonylmethyl, 2-CH₃-[1,3,4]thiadiazol-5-ylmethanesulfonylmethyl, 2-CF₃-[1,3,4]thiadiazol-5-ylmethanesulfonylmethyl, 2-phenyl-[1,3,4]thiadiazol-5-ylmethane-sulfonylmethyl, 2,2-difluoropyrrolidinylmethanesulfonylmethyl, 3,3-difluoropyrrolidinyl-methanesulfonylmethyl, 3-CF₃—N—CH₃-pyrrol-2-ylmethanesulfonylmethyl, 3-CN—N—CH₃-pyrrol-2-ylmethanesulfonylmethyl, 4-CF₃—N—CH₃-pyrrol-2-ylmethanesulfonylmethyl, 4-(1-CH₃-1-hydroxyethyl)-N—CH₃-pyrrol-2-ylmethanesulfonylmethyl, 1,3-dimethylpyrrol-2-ylmethanesulfonylmethyl, 4-CF₃—N—CH₃-pyrrol-3-ylmethanesulfonylmethyl, 4-CN—N—CH₃-pyrrol-3-ylmethanesulfonylmethyl, 4-CN-N-(3,3,3-trifluoropropyl)-pyrrol-3-ylmethanesulfonylmethyl, 2-CF₃—N—CH₃-pyrrol-3-ylmethanesulfonylmethyl, 2-CF₃-N-phenyl-pyrrol-3-ylmethane-sulfonylmethyl, 4-CF₃-pyrrol-2-ylmethanesulfonylmethyl, 4-(1-CH₃-1-hydroxyethyl)-pyrrol-2-ylmethanesulfonylmethyl, 3-CH₃-pyrrol-2-ylmethanesulfonylmethyl, 4-CF₃-pyrrol-3-ylmethane-sulfonylmethyl, 2-CF₃-pyrrol-3-ylmethanesulfonylmethyl, 3-CF₃-pyrrol-2-ylmethane-sulfonylmethyl, 2-CF₃-pyrrol-4-ylmethanesulfonylmethyl, 2-CF₃—N—CH₃-pyrrol-4-yl-methane-sulfonylmethyl, 3-CF₃-fur-2-ylmethanesulfonylmethyl, 3-CN-fur-2-ylmethanesulfonylmethyl, 3-CF₃-fur-4-ylmethanesulfonylmethyl, 3-CN-fur-4-ylmethanesulfonylmethyl, 2-CF₃-fur-3-ylmethanesulfonylmethyl, 3-CF₃-thiazol-2-ylmethanesulfonylmethyl, 3-CN-thiazol-2-ylmethanesulfonylmethyl, 3-CF₃-thiazol-4-ylmethanesulfonylmethyl, 3-CN-thiazol-4-ylmethanesulfonylmethyl, 2-CF₃-thiazol-3-ylmethanesulfonylmethyl, N—CH₃-3-CF₃-1H-pyrazol-5-ylmethanesulfonylmethyl, N—CH₃-3-(1-CH₃-1-hydroxyethyl)-1H-pyrazol-5-ylmethane-sulfonylmethyl, N—CH₃-3-phenyl-1H-pyrazol-5-ylmethanesulfonylmethyl, N—CH₃-3-CF₃-1H-pyrazol-4-ylmethanesulfonylmethyl, N—CH₃-4-CN-1H-pyrazol-3-ylmethanesulfonylmethyl, N-phenyl-4-CN-1H-pyrazol-3-ylmethanesulfonylmethyl, N-phenyl-3-CF₃-1H-pyrazol-4-ylmethanesulfonylmethyl, N-phenyl-5-CF₃-1H-pyrazol-4-ylmethanesulfonylmethyl, (N—CH₃-4-CF₃-1H-imidazol-2-ylmethane)-sulfonylmethyl, [N—CH₃-4-(1-CH₃-1-hydroxyethyl)-1H-imidazol-2-ylmethane]-sulfonylmethyl, (N—CH₃-4-phenyl-1H-imidazol-2-ylmethane)-sulfonylmethyl, N—CH₃-3-CF₃-1H-pyrazol-4-ylmethanesulfonylmethyl, (N—CH₃-2-CF₃-1H-imidazol-5-ylmethane)-sulfonylmethyl, (N—CH₃-2-phenyl-1H-imidazol-5-ylmethane)-sulfonylmethyl, (N—CH₃-5-CF₃-1H-imidazol-4-ylmethane)-sulfonylmethyl, (N-phenyl-5-CF₃-1H-imidazol-4-ylmethane)-sulfonylmethyl, 4-CN-[1,2]oxazol-5-ylmethanesulfonylmethyl 4-CN-3-phenyl-[1,2]oxazol-5-ylmethanesulfonylmethyl, 4-CN-[1,2]oxazol-3-ylmethanesulfonylmethyl, 4-CN-5-phenyl-[1,2]oxazol-3-ylmethanesulfonylmethyl, 4-CN-isothiazol-5-ylmethanesulfonylmethyl, 4-CN-3-phenyl-isothiazol-5-ylmethanesulfonylmethyl, 4-CN-isothiazol-3-ylmethanesulfonylmethyl, 4-CN-5-phenyl-isothiazol-3-ylmethane-sulfonylmethyl, 4-CF₃-[1,2]oxazol-5-ylmethanesulfonylmethyl, 4-CF₃-3-CH₃-[1,2]oxazol-5-ylmethanesulfonylmethyl, 4-CF₃-3-phenyl-[1,2]oxazol-5-ylmethanesulfonylmethyl, 4-CF₃-[1,2]oxazol-3-ylmethanesulfonylmethyl, 4-CF₃-5-CH₃-[1,2]oxazol-3-ylmethanesulfonylmethyl 4-CF₃-5-phenyl-[1,2]oxazol-3-ylmethanesulfonylmethyl. 3-CF₃-[1,2]oxazol-4-ylmethanesulfonylmethyl, 5-CF₃-[1,2]oxazol-4-ylmethanesulfonylmethyl, 4-CF₃-[1,2]oxazol-5-ylmethanesulfonylmethyl, 4-CF₃-3-CH₃-[1,2]oxazol-5-ylmethanesulfonylmethyl, 4-CF₃-3-phenyl-[1,2]oxazol-5-ylmethanesulfonylmethyl, 4-CF₃-[1,2]oxazol-3-ylmethanesulfonylmethyl, 4-CF₃-5-CH₃-[1,2]oxazol-3-ylmethanesulfonylmethyl, 4-CF₃-5-phenyl-[1,2]oxazol-3-ylmethanesulfonylmethyl, 3-CF₃-[1,2]oxazol-4-ylmethanesulfonylmethyl, 5-CF₃-[1,2]oxazol-4-ylmethanesulfonylmethyl, 4-CH₃-[1,2]oxazol-5-ylmethanesulfonylmethyl, 4-CH₃-3-phenyl-[1,2]oxazol-5-ylmethanesulfonylmethyl, 4-CH₃-[1,2]oxazol-3-ylmethanesulfonylmethyl, 4-CH₃-5-phenyl-[1,2]oxazol-3-ylmethanesulfonylmethyl, 3-CH₃-[1,2]oxazol-4-ylmethane-sulfonylmethyl, 5-CH₃-[1,2]oxazol-4-ylmethanesulfonylmethyl, 4-CH₃-isothiazol-5-ylmethane-sulfonylmethyl, 4-CH₃-3-phenyl-isothiazol-5-ylmethanesulfonylmethyl, 4-CH₃-isothiazol-3-ylmethanesulfonylmethyl, 4-CH₃-5-phenyl-isothiazol-3-ylmethanesulfonylmethyl, 3-CH₃-isothiazol-4-ylmethanesulfonylmethyl, 5-CH₃-isothiazol-4-ylmethanesulfonylmethyl, 4-CF₃-2-CH₃-[1,3]oxazol-5-ylmethanesulfonylmethyl, 4-CF₃-[1,3]oxazol-5-ylmethanesulfonylmethyl, 4-CF₃-2-phenyl-[1,3]oxazol-5-ylmethanesulfonylmethyl, 5-CF₃-2-CH₃-[1,3]oxazol-4-yl-methanesulfonylmethyl, 5-CF₃-[1,3]oxazol-4-ylmethanesulfonylmethyl, 5-CF₃-2-phenyl-[1,3]oxazol-4-ylmethanesulfonylmethyl, 5-CH₃-[1,3]oxazol-2-ylmethanesulfonylmethyl, 5-CF₃-[1,3]oxazol-2-ylmethanesulfonylmethyl, 5-phenyl-[1,3]oxazol-2-ylmethane-sulfonylmethyl, 4-CH₃-[1,3]oxazol-2-ylmethanesulfonylmethyl, 4-CF₃-[1,3]oxazol-2-ylmethanesulfonylmethyl, 4-phenyl-[1,3]oxazol-2-ylmethanesulfonylmethyl, N-methyl-indol-2-ylmethanesulfonylmethyl, 3-CF₃-indol-2-ylmethanesulfonylmethyl, 3-CF₃-N-methyl-indol-2- ylmethanesulfonylmethyl, 5-fluoro-N-methyl-indol-2-ylmethanesulfonylmethyl, N-methyl-indol-3-ylmethanesulfonylmethyl, 2-CF$_3$-indol-3-ylmethanesulfonylmethyl, 2-CF$_3$-N-methyl-indol-3-ylmethanesulfonylmethyl, 5-fluoro-N-methyl-indol-3-ylmethanesulfonylmethyl, 5-CF$_3$-N-methyl-indol-4-ylmethanesulfonylmethyl, 5-CN-N-methyl-indol-4-ylmethanesulfonylmethyl, 2-CF$_3$-N-methyl-indol-4-ylmethanesulfonylmethyl, 3-CF$_3$-N-methyl-indol-4-ylmethanesulfonylmethyl, 6-CF$_3$-N-methyl-indol-7-ylmethanesulfonylmethyl, 6-CN-N-methyl-indol-7-ylmethanesulfonylmethyl, 2-CF$_3$-N-methyl-indol-7-ylmethanesulfonylmethyl, 3-CF$_3$-N-methyl-indol-7-ylmethanesulfonylmethyl, benzofuran-2-ylmethanesulfonylmethyl, 3-CF$_3$-benzofuran-2-ylmethanesulfonylmethyl, 3-CN-benzofuran-2-ylmethanesulfonylmethyl, 5-F-benzofuran-2-ylmethanesulfonylmethyl, benzofuran-3-ylmethanesulfonylmethyl, 2-CF$_3$-benzofuran-3-ylmethanesulfonylmethyl, 2-CH$_3$-benzofuran-3-ylmethanesulfonylmethyl, 5-F-benzofuran-3-ylmethanesulfonylmethyl, 5-CF$_3$-benzofuran-4-ylmethanesulfonylmethyl, 5-CN-benzofuran-4-ylmethanesulfonylmethyl, 2-CF$_3$-benzofuran-4-ylmethanesulfonylmethyl, 3-CF$_3$-benzofuran-4-ylmethanesulfonylmethyl, 6-CF$_3$-benzofuran-7-ylmethanesulfonylmethyl, 6-CN-benzofuran-7-ylmethanesulfonylmethyl, 2-CF$_3$-benzofuran-7-ylmethanesulfonylmethyl, 3-CF$_3$-benzofuran-7-ylmethanesulfonylmethyl, benzothien-2-ylmethanesulfonylmethyl, (3-CF$_3$-benzothien-2-ylmethane)-sulfonylmethyl, (3-CN-benzothien-2-ylmethane)-sulfonylmethyl, (5-F-benzothien-2-ylmethane)-sulfonylmethyl, benzothien-3-ylmethanesulfonylmethyl, (2-CF$_3$-benzothien-3-ylmethane)-sulfonylmethyl, (2-CH$_3$-benzothien-3-ylmethane)-sulfonylmethyl, (5-fluoro-benzothien-3-ylmethane)-sulfonylmethyl, (5-CF$_3$-benzothien-4-ylmethane)-sulfonylmethyl, (5-CN-benzothien-4-ylmethane)-sulfonylmethyl, (2-CF$_3$-benzothien-4-ylmethane)-sulfonylmethyl, (3-CF$_3$-benzothien-4-ylmethane)-sulfonylmethyl, (6-CF$_3$-benzothien-7-ylmethane)-sulfonylmethyl, (6-CN-benzothien-7-ylmethane)-sulfonylmethyl, (2-CF$_3$-benzothien-7-ylmethane)-sulfonylmethyl, (3-CF$_3$-benzothien-7-ylmethane)-sulfonylmethyl, N-methyl-benzimidazol-2-ylmethanesulfonylmethyl, (5-fluoro-N-methyl-benzimidazol-2-ylmethane)-sulfonylmethyl, (N-methyl-indazol-3-ylmethane)-sulfonylmethyl, (5-fluoro-N-methyl-indazol-3-ylmethane)-sulfonylmethyl, (2-CF$_3$-N-methyl-benzimidazol-4-ylmethane)-sulfonylmethyl, (2-CF$_3$-N-methyl-benzimidazol-7-ylmethane)-sulfonylmethyl, (N-methyl-indazol-4-ylmethane)-sulfonylmethyl, (5-CF$_3$-N-methyl-indazol-4-ylmethane)-sulfonylmethyl, (3-CF$_3$-N-methyl-indazol-4-ylmethane)-sulfonylmethyl, (6-CF$_3$-N-methyl-indazol-7-ylmethane)-sulfonylmethyl, (6-CN-N-methyl-imidazol-7-ylmethane)-sulfonylmethyl, or (3-CF$_3$-N-methyl-indazol-7-ylmethane)-sulfonylmethyl.

(i) Within this group (G), a preferred group of compounds is that wherein:
R$^4$ is hydrogen; and
R$^{4'}$ is 1,1,2,2-tetrafluoroethyl or 1,1,2,2,2-pentafluoroethyl.

(ii) Within this group (G), another preferred group of compounds is that wherein:
R$^{4'}$ is difluoromethyl or trifluoromethyl; and
R$^4$ is phenyl, 2-fluorophenyl, or 2,4-difluorophenyl.

(iii) Within this group (G), yet another preferred group of compounds is that wherein:
R$^4$ is difluoromethyl or trifluoromethyl; and
R$^{4'}$ is 1,1,2,2-tetrafluoroethyl or 1,1,2,2,2-pentafluoroethyl.

(iv) Within this group (G), yet another preferred group of compounds is that wherein:
R$^4$ is methyl or ethyl; and
R$^{4'}$ is 1,1,2,2-tetrafluoroethyl or 1,1,2,2,2-pentafluoroethyl.

Within the above preferred group (G), G(i), G(ii), G(iii) and G(iv), a particularly preferred group of compounds is that wherein R$^1$ and R$^2$ together with the carbon atom to which they are attached form cycloalkylene, preferably R$^1$ and R$^2$ together with the carbon atom to which they are attached form cyclopropylene.

Within the above preferred group (G), G(i), G(ii), G(iii) and G(iv), another particularly preferred group of compounds is that wherein R$^1$ and R$^2$ together with the carbon atom to which they are attached form piperidin-4-yl substituted at the nitrogen with ethyl, trifluoroethyl or cyclopropyl.

Within the above preferred group (G), G(i), G(ii), G(iii) and G(iv), yet another particularly preferred group of compounds is that wherein R$^1$ and R$^2$ together with the carbon atom to which they are attached form tetrahydropyran-4-yl, tetrahydrothiopyran-4-yl, or 1,1-dioxohexahydrothiopyran-4-yl.

Reference to the preferred embodiments set forth above is meant to include all combinations of particular and preferred groups unless stated otherwise.

Compounds of Formula (I) where R$^1$ and R$^2$ together form cyclopropylene and R$^3$, R$^4$, and R$^{4'}$ are as defined in Table I below are:

TABLE I

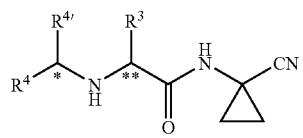

(I)

| Cpd # | Stereochem at (*C, **C) | R$^{4'}$ | R$^3$ | R$^4$ |
|---|---|---|---|---|
| 1 | (S, R) | CF$_3$ | 4-CF$_3$-pyridin-3-ylmethanesulfonylmethyl | 4-Fphenyl |
| 2 | (S, R) | CF$_3$ | pyridin-3-ylmethanesulfonylmethyl | 4-F-phenyl |
| 3 | (S, R) | CF$_3$ | pyridazin-3-ylmethanesulfonylmethyl | 4-F-phenyl |
| 4 | (S, R) | CF$_3$ | 2-CF$_3$-furan-5-ylmethanesulfonylmethyl | 4-F-phenyl |

TABLE I-continued

Structure (I):

R⁴-*CH(R⁴')-NH-**CH(R³)-C(=O)-NH-C(cyclopropyl)(CN)

| Cpd # | Stereochem at (*C, **C) | R⁴' | R³ | R⁴ |
|---|---|---|---|---|
| 5 | (S, R) | CF₃ | pyrimidin-5-ylmethanesulfonylmethyl | 4-F-phenyl |
| 6 | (S, R) | CF₃ | 2-CH₃-thiazol-4-ylmethanesulfonylmethyl | 4-F-phenyl |
| 7 | (S, R) | CF₃ | pyridin-4-ylmethanesulfonylmethyl | 4-F-phenyl |
| 8 | (S, R) | CF₃ | pyrimidin-4-ylmethanesulfonylmethyl | 4-F-phenyl |
| 9 | (S, R) | CF₃ | 2-(1-oxopyrrol-1-yl)ethanesulfonylmethyl | 4-F-phenyl |
| 10 | (R, R) | CF₃ | pyridin-3-ylmethanesulfonylmethyl | 4-F-phenyl |
| 11 | (S, R) | CF₃ | cyclopropylmethanesulfonylmethyl | 3-F-phenyl |
| 12 | (S, R) | CF₃ | 3,3,3-trifluoropropane-1-sulfonylmethyl | 4-F-phenyl |
| 13 | (S, R) | CF₃ | 2-CF₃-pyridin-5-ylmethanesulfonylmethyl | 4-F-phenyl |
| 14 | (S, R) | CF₃ | 4-[1.2.4]-triazol-1-ylphenylmethane-sulfonylmethyl | 4-F-phenyl |
| 15 | (S, R) | CF₃ | 2-(2-oxo-2,3-dihydrobenzimidazol-1-yl)-ethanesulfonylmethyl | 4-F-phenyl |
| 16 | (S, R) | CF₃ | 5-oxopyrrolidin-2-ylmethanesulfonylmethyl | 4-F-phenyl |
| 17 | (S, R) | CF₃ | 2-F-pyridin-3-ylmethanesulfonylmethyl | 4-F-phenyl |
| 18 | (S, R) | CF₃ | 3-CH₃-oxetan-3-ylmethanesulfonylmethyl | 4-F-phenyl |
| 19 | (S, R) | CF₃ | 2-phenylethanesulfonylmethyl | 4-F-phenyl |
| 20 | (R, R) | CF₃ | 3,3,3-trifluoropropane-1-sulfonylmethyl | 4-F-phenyl |
| 21 | (S, R) | CF₃ | fluoro-pyridin-2-ylmethanesulfonylmethyl | 4-F-phenyl |
| 22 | (S, R) | CF₃ | fluoro-pyrazin-2-ylmethanesulfonylmethyl | 4-F-phenyl |
| 23 | (S, R) | CF₃ | difluoro-pyridin-2-ylmethanesulfonylmethyl | 4-F-phenyl |
| 24 | (S, R) | CF₃ | difluoro-pyridin-3-ylmethanesulfonylmethyl | 4-F-phenyl |
| 25 | (S, R) | CF₃ | quinolin-2-ylmethanesulfonylmethyl | 4-F-phenyl |
| 26 | (S, R) | CF₃ | benzo[1.2.5]thiadiazol-4-yl-methanesulfonylmethyl | 4-F-phenyl |
| 27 | (S, R) | CF₃ | benzothiazol-2-ylmethanesulfonylmethyl | 4-F-phenyl |
| 28 | (S, R) | CF₃ | 5-methylisoxazol-3-ylmethanesulfonylmethyl | 4-F-phenyl |
| 29 | (S, R) | CF₃ | 2-methylpropylsulfonylmethyl | 4-F-phenyl |
| 30 | (S, R) | CF₃ | cyclobutylmethanesulfonylmethyl | 4-F-phenyl |
| 31 | (S, R) | CF₃ | 2,6-difluorophenylmethanesulfonylmethyl | 4-F-phenyl |
| 32 | (S, R) | CF₃ | 2,4-difluorophenylmethanesulfonylmethyl | 4-F-phenyl |
| 33 | (S, R) | CF₃ | quinolin-3-ylmethanesulfonylmethyl | 4-F-phenyl |
| 34 | (S, R) | CF₃ | 4,4,4-trifluorobutyl-1-sulfonylmethyl | 4-F-phenyl |
| 35 | (S, R) | CF₃ | 2-CF₃-phenylmethanesulfonylmethyl | 4-F-phenyl |
| 36 | (S, R) | CF₃ | 2-CF₃O-phenylmethanesulfonylmethyl | 4-F-phenyl |
| 37 | (S, R) | CF₃ | cyclopropylmethanesulfonylmethyl | 3,5-diF-phenyl |
| 38 | (S, R) | CF₃ | cyclopropylmethanesulfonylmethyl | 2,5-diF-phenyl |
| 39 | (S, R) | CF₃ | 2-pyridin-2-ylethanesulfonylmethyl | 4-F-phenyl |
| 40 | (S, R) | CF₃ | 2-pyridin-3-ylethanesulfonylmethyl | 4-F-phenyl |
| 41 | (S, R) | CF₃ | quinolin-8-ylmethanesulfonylmethyl | 4-F-phenyl |
| 42 | (S, R) | CF₃ | cyclopropylmethanesulfonylmethyl | 2,3-diF-phenyl |
| 43 | (S, R) | CF₃ | cyclopropylmethanesulfonylmethyl | 2,4-diF-phenyl |
| 44 | (S, R) | CF₃ | 5-methyl-3-phenylisoxazol-4-yl-methanesulfonylmethyl | 4-F-phenyl |
| 45 | (S, R) | CF₃ | 4-methyl-2-phenyl-[1.2.3]triazol-5-ylmethane-sulfonylmethyl | 4-F-phenyl |
| 46 | (S, R) | CF₃ | 2-cyanophenylmethanesulfonylmethyl | 4-F-phenyl |
| 47 | (S, R) | CF₃ | 3-methoxycarbonylphenylmethanesulfonylmethyl | 4-F-phenyl |
| 48 | (S, R) | CHF₂ | cyclopropylmethanesulfonylmethyl | 4-F-phenyl |
| 49 | (RS, R) | CF₃ | cyclopropylmethanesulfonylmethyl | 2-Cl-pyridin-5-yl |
| 50 | (S, R) | CF₂CF₃ | pyridin-2-ylmethanesulfonylmethyl | 4-F-phenyl |
| 51 | (S, R) | CF₂CF₃ | 1-oxopyridin-2-ylmethanesulfonylmethyl | 4-F-phenyl |
| 52 | (S, R) | CF₂CF₃ | pyridin-3-ylmethanesulfonylmethyl | 4-F-phenyl |
| 53 | (S, R) | CF₂CF₃ | 1-oxopyridin-3-ylmethanesulfonylmethyl | 4-F-phenyl |
| 54 | (S, R) | CF₂CF₃ | cyclopropylmethanesulfonylmethyl | 4-F-phenyl |
| 55 | (S, R) | CF₃ | quinoxalin-2-ylmethanesulfonylmethyl | 4-F-phenyl |
| 56 | (S, R) | CF₃ | tetrahydropyran-2(RS)-ylmethanesulfonylmethyl | 4-F-phenyl |
| 57 | (S, R) | CF₃ | 2,6-dichlorophenylmethanesulfonylmethyl | 4-F-phenyl |
| 58 | (S, R) | CF₃ | 3-methoxycarbonylfuran-2-yl-methanesulfonylmethyl | 4-F-phenyl |
| 59 | (S, R) | CF₂CF₃ | 5-methylisoxazol-3-ylmethanesulfonylmethyl | 4-F-phenyl |
| 60 | (S, R) | CF₃ | 2,2-dimethylpropylsulfonylmethyl | 4-F-phenyl |
| 61 | (R, R) | CF₂CF₃ | pyridin-3-ylmethanesulfonylmethyl | 4-F-phenyl |
| 62 | (S, R) | CF₃ | ethanesulfonylmethyl | 4-F-phenyl |

TABLE I-continued (I)

Structure: R4-*CH(R4')-NH-**CH(R3)-C(=O)-NH-C(CN)(cyclopropyl)

| Cpd # | Stereochem at (*C, **C) | R4' | R3 | R4 |
|---|---|---|---|---|
| 63 | (R, R) | $CF_3$ | cyclopropylmethanesulfonylmethyl | 2,5-diF-phenyl |
| 64 | (S, R) | $CF_3$ | cyclopropylmethanesulfonylmethyl | 2,6-diF-phenyl |
| 65 | (R, R) | $CF_3$ | cyclopropylmethanesulfonylmethyl | 2,6-diF-phenyl |
| 66 | (R, R) | $CF_3$ | cyclopropylmethanesulfonylmethyl | 2,3-diF-phenyl |
| 67 | (R, R) | $CF_3$ | cyclopropylmethanesulfonylmethyl | 2,4-diF-phenyl |
| 68 | (S, R) | $CF_3$ | methanesulfonylmethyl | 4-F-phenyl |
| 69 | (S, R) | $CF_3$ | propane-1-sulfonylmethyl | 4-F-phenyl |
| 70 | (S, R) | $CF_3$ | 1H-indol-2-ylmethanesulfonylmethyl | 4-F-phenyl |
| 71 | (S, R) | $CF_3$ | cyclopropylmethanesulfonylmethyl | 2-F-phenyl |
| 72 | (R, R) | $CF_3$ | cyclopropylmethanesulfonylmethyl | 2-F-phenyl |
| 73 | (S, R) | $CF_3$ | pyridin-2-ylmethanesulfonylmethyl | 3,4-diF-phenyl |
| 74 | (S, R) | $CF_3$ | pyridin-3-ylmethanesulfonylmethyl | 3,4-di-Fphenyl |
| 75 | (S, R) | $CF_3$ | 2-(1H-indol-3-yl)ethanesulfonylmethyl | 4-F-phenyl |
| 76 | (S, R) | $CF_3$ | tetrahydropyran-4-ylmethanesulfonylmethyl | 4-F-phenyl |
| 77 | (S, R) | $CF_3$ | 1-oxopyridin-2-ylmethanesulfonylmethyl | 2-F-phenyl |
| 78 | (R, R) | $CF_3$ | 1-oxopyridin-2-ylmethanesulfonylmethyl | 2-F-phenyl |
| 79 | (S, R) | $CF_3$ | pyridin-2-ylmethanesulfonylmethyl | 2-F-phenyl |
| 80 | (R, R) | $CF_3$ | pyridin-2-ylmethanesulfonylmethyl | 2-F-phenyl |
| 81 | (S, R) | $CF_3$ | cyclopropylmethanesulfonylmethyl | 2,3,4-triF-phenyl |
| 82 | (R, R) | $CF_3$ | cyclopropylmethanesulfonylmethyl | 2,3,4-triF-phenyl |
| 83 | (S, R) | $CF_3$ | 2,2,2-trifluoroethanesulfonylmethyl | 2-F-phenyl |
| 84 | (S, R) | $CF_3$ | benzisoxazol-3-ylmethanesulfonylmethyl | 2-F-phenyl |
| 85 | (RS, R) | $CF_3$ | cyclopropylmethanesulfonylmethyl | 3-OH-6-$CH_3$-pyridin-2-yl |
| 86 | (S, R) | $CF_3$ | 2-tert-butyl-[1.3.4]thiadiazol-5-ylmethanesulfonylmethyl | 4-F-phenyl |
| 87 | (S, R) | $CF_3$ | 2,4,6-trifluorophenylmethanesulfonylmethyl | 4-F-phenyl |
| 88 | (S, R) | $CF_2CF_3$ | 2-pyridin-2-ylethanesulfonylmethyl | 4-F-phenyl |
| 89 | (S, R) | $CF_3$ | 1-ethyl-2,5-dioxopyrrolidin-3-ylmethanesulfonylmethyl | 4-F-phenyl |
| 90 | (S, R) | $CF_3$ | benzisoxazol-3-ylmethanesulfonylmethyl | 4-F-phenyl |
| 91 | (S, R) | $CF_3$ | cyclopropylmethanesulfonylmethyl | 2,4,5-triF-phenyl |
| 92 | (S, S) | $CF_3$ | 2-cyclopropylmethylsulfonylethyl | 4-F-phenyl |
| 93 | (S, S) | $CF_3$ | 2-methylsulfonylethyl | 4-F-phenyl |
| 94 | (S, S) | $CF_3$ | 2-phenylsulfonylethyl | 4-F-phenyl |
| 95 | (S, S) | $CF_3$ | 2-(4-trifluoromethylphenylsulfonyl)ethyl | 4-F-phenyl |
| 96 | (S, S) | $CF_3$ | 2-(4-methylsulfonylphenylsulfonyl)ethyl | 4-F-phenyl |
| 97 | (S, R) | $CF_3$ | butylsulfonylmethyl | 4-F-phenyl |
| 98 | (S, R) | $CF_3$ | pentylsulfonylmethyl | 4-F-phenyl |
| 99 | (S, R) | $CF_3$ | hexylsulfonylmethyl | 4-F-phenyl |
| 100 | (S, R) | $CF_3$ | heptylsulfonylmethyl | 4-F-phenyl |
| 101 | (S, R) | $CF_3$ | 3-phenylisooxazol-5-ylmethylsulfonylmethyl | 4-F-phenyl |
| 102 | (S, R) | $CF_3$ | 5-phenyloxazol-4-ylmethylsulfonylmethyl | 4-F-phenyl |
| 103 | (S, R) | $CF_3$ | [1,2,4]oxadiaxol-3-ylmethylsulfonylmethyl | 4-F-phenyl |
| 104 | (S, R) | $CF_3$ | 5-phenyl[1,2,4]oxadiaxol-3-ylmethylsulfonylmethyl | 4-F-phenyl |
| 105 | (S, R) | $CF_3$ | 5-thiophen-2-yl[1,2,4]oxadiaxol-3-ylmethylsulfonylmethyl | 4-F-phenyl |
| 106 | (S, R) | $CF_3$ | 3-thiophen-5-yl[1,2,4]oxadiaxol-3-ylmethylsulfonylmethyl | 4-F-phenyl |
| 107 | (S, R) | $CF_3$ | 3,5-dimethylisooxadiaxol-4-ylmethylsulfonylmethyl | 4-F-phenyl |
| 108 | (S, R) | $CF_3$ | 6-methylpyridin-2-ylmethylsulfonylmethyl | 4-F-phenyl |
| 109 | (S, R) | $CF_3$ | 3-trifluoromethyl-pyridin-4-ylmethanesulfonylmethyl | 4-F-phenyl |
| 110 | (S, R) | $CF_3$ | cyclopropylmethylsulfonylmethyl | 2,4,6-triF-phenyl |
| 111 | (R, R) | $CF_3$ | cyclopropylmethylsulfonylmethyl | 2,4,6-triF-phenyl |

TABLE I-continued (I)

Structure: R4-*CH(R4')-NH-**CH(R3)-C(=O)-NH-C(CN)(cyclopropyl)

| Cpd # | Stereochem at (*C, **C) | R4' | R3 | R4 |
|---|---|---|---|---|
| 112 | (R) | CF$_2$CHF$_2$ | cyclopropylmethylsulfonylmethyl | hydrogen |
| 113 | (RS, R) | CF$_2$CHF$_2$ | 3-trifluorobenzylsulfonylmethyl | 2,4-diF-phenyl |
| 114 | (S, R) | CF$_2$CHF$_2$ | 3-trifluorobenzylsulfonylmethyl | 2,4-diF-phenyl |
| 115 | (S, R) | CF$_3$ | 2-(2-oxoindol-1-yl)ethylsulfonylmethyl | 4-F-phenyl |
| 116 | (S, R) | CF$_3$ | 2-(2,3-dioxoindol-1-yl)ethylsulfonylmethyl | 4-F-phenyl |
| 117 | (S, R) | CF$_3$ | 4-methylsulfonylbenzylsulfonylmethyl | 2,4-diF-phenyl |
| 118 | (S, R) | CF$_3$ | 3-methylsulfonylbenzylsulfonylmethyl | 2,4-diF-phenyl |
| 119 | (R, R) | CF$_3$ | 3-methylsulfonylbenzylsulfonylmethyl | 2,4-diF-phenyl |
| 120 | (R, R) | CF$_3$ | 2-cyanobenzylsulfonylmethyl | 2,4-diF-phenyl |
| 121 | (S, R) | CF$_3$ | 2-cyanobenzylsulfonylmethyl | 2,4-diF-phenyl |
| 122 | (S, R) | CF$_3$ | 2-methylsulfonylbenzylsulfonylmethyl | 2,4-diF-phenyl |
| 123 | (R, R) | CF$_3$ | 2-methylsulfonylbenzylsulfonylmethyl | 2,4-diF-phenyl |
| 124 | (R, R) | CF$_3$ | 4-methylsulfonylbenzylsulfonylmethyl | 2,4-diF-phenyl |
| 125 | (S, R) | CF$_3$ | 4-trifluoromethylpyridin-3-ylsulfonylmethyl | 2,4-diF-phenyl |
| 126 | (R, R) | CF$_3$ | 2-trifluoromethylbenzylsulfonylmethyl | 2,4-diF-phenyl |
| 127 | (S, R) | CF$_3$ | 2-trifluoromethylbenzylsulfonylmethyl | 2,4-diF-phenyl |
| 128 | (S, R) | CF$_3$ | phenylsulfonylmethyl | 4-F-phenyl |
| 129 | (S, R) | CF$_3$ | 2-methylsulfonylbenzylsulfonylmethyl | 4-F-phenyl |
| 130 | (S, R) | CF$_3$ | 4-methylsulfonylbenzylsulfonylmethyl | 4-F-phenyl |
| 131 | (S, R) | CF$_3$ | 3-methylsulfonylbenzylsulfonylmethyl | 4-F-phenyl |
| 132 | (S, R) | CF$_3$ | 2-(2-oxo-imidazolidin-1-yl)-ethanesulfonylmethyl | 4-F-phenyl |
| 133 | (S, R) | CF$_3$ | 2-(2-oxo-imidazolidin-1-yl)-ethanesulfonylmethyl | 2,4-diF-phenyl |
| 134 | (S, R) | CF$_3$ | 2-[4-(4-fluorophenyl)-2-trifluoromethyl-imidazol-1-yl]-ethanesulfonylmethyl | 2,4-diF-phenyl |
| 135 | (S, R) | CF$_3$ | 2-[4-(4-fluorophenyl)-2-trifluoromethyl-imidazol-1-yl]-ethanesulfonylmethyl | 4-F-phenyl |
| 136 | (S, R) | CF$_3$ | 2-[5-(4-fluorophenyl)-2-trifluoromethyl-imidazol-1-yl]-ethanesulfonylmethyl | 4-F-phenyl |
| 137 | (S, R) | CF$_3$ | 2-(2-trifluoromethylimidazol-1-yl)ethanesulfonylmethyl | 4-F-phenyl |
| 138 | (S, R) | CF$_3$ | 2-(2-trifluoromethylimidazol-1-yl)ethanesulfonylmethyl | 2,4-diF-phenyl |
| 139 | (S, R) | CF$_3$ | cyclopropylmethylsulfonylmethyl | tetrahydropyr |
| 140 | (S, R) | CF$_3$ | 2-(2-oxo-pyrrolidin-1-yl)-ethanesulfonylmethyl | 4-F-phenyl |
| 141 | (S, R) | CF$_3$ | 2-(4-oxo-5-aza-benzospiro[2.4]hept-6-en-5-yl)-ethanesulfonylmethyl | 4-F-phenyl |
| 142 | (S, R) | CF$_3$ | cyclopropylmethylsulfonylmethyl | 4-Cl-phenyl | and compounds of Formula (I) $R^1$, $R^2$, $R^3$, $R^4$ and $R^{4'}$ are as defined in Table II below are:

TABLE II (I)

| Cpd # | Stereochem at (*C, **C) | $R^1$ and $R^2$ | $R^{4'}$ | $R^3$ | $R^4$ |
|---|---|---|---|---|---|
| 143 | (S, R) | cyclopentylene | $CF_3$ | pyridine-3-ylmethanesulfonylmethyl | 4-Fphenyl |
| 144 | (S, R) | cyclobutylene | $CF_3$ | pyridine-3-ylmethanesulfonylmethyl | 4-Fphenyl |
| 145 | (S, R) | $CH_3$ and $CH_3$ | $CF_3$ | pyridine-3-ylmethanesulfonylmethyl | 4-Fphenyl |
| 146 | (S, R) | cyclobutylene | $CF_3$ | cyclopropylmethanesulfonylmethyl | 4-Fphenyl |
| 147 | (S, R) | $CH_3$ and $CH_3$ | $CF_3$ | 4-trifluoromethylpyridin-3-ylmethanesulfonylmethyl | 4-Fphenyl | and are named:

N-(1-cyanocyclopropyl)-3-(4-trifluoromethylpyridin-3-yl-methanesulfonyl)-2(R)-(2,2,2-trifluoro-1 (S)-4-fluorophenylethylamino)-propionamide;

N-(1-cyanocyclopropyl)-3-pyridin-3-ylmethanesulfonyl-2 (R)-(2,2,2-trifluoro-1(S)-4-fluorophenylethylamino)propionamide;

N-(1-cyanocyclopropyl)-3-pyridan-3-ylmethanesulfonyl-2 (R)-(2,2,2-trifluoro-1(S)-4-fluorophenylethylamino)propionamide;

N-(1-cyanocyclopropyl)-3-(2-trifluoromethylfuran-5-yl-methanesulfonyl)-2(R)-(2,2,2-trifluoro-1(S)-4-fluorophenylethylamino)-propionamide;

N-(1-cyanocyclopropyl)-3-pyrimidin-5-ylmethanesulfonyl-2(R)-(2,2,2-trifluoro-1(S)-4-fluorophenylethylamino)propionamide;

N-(1-cyanocyclopropyl)-3-(2-methylthiazol-4-ylmethanesulfonyl)-2(R)-(2,2,2-trifluoro-1(S)-4-fluorophenylethylamino)propionamide;

N-(1-cyanocyclopropyl)-3-pyridin-4-ylmethanesulfonyl-2 (R)-(2,2,2-trifluoro-1(S)-4-fluorophenylethylamino)propionamide;

N-(1-cyanocyclopropyl)-3-pyrimidin-4-ylmethanesulfonyl-2(R)-(2,2,2-trifluoro-1(S)-4-fluorophenylethylamino)propionamide;

N-(1-cyanocyclopropyl)-3-[2-(1-oxopyrrol-1-yl)ethanesulfonyl]-2(R)-(2,2,2-trifluoro-1(S)-4-fluorophenylethylamino)propionamide;

N-(1-cyanocyclopropyl)-3-pyridin-3-ylmethanesulfonyl-2 (R)-(2,2,2-trifluoro-1(R)-4-fluorophenylethylamino)propionamide;

N-(1-cyanocyclopropyl)-3-cyclopropylmethanesulfonyl-2 (R)-(2,2,2-trifluoro-1(S)-3-fluorophenylethylamino)propionamide;

N-(1-cyanocyclopropyl)-3-(3,3,3-trifluoropropane-1-sulfonyl)-2(R)-(2,2,2-trifluoro-1(S)-4-fluorophenylethylamino)propionamide;

N-(1-cyanocyclopropyl)-3-(2-trifluoromethylpyridin-5-yl-methanesulfonyl)-2(R)-(2,2,2-trifluoro-1(S)-4-fluorophenylethylamino)-propionamide;

N-(1-cyanocyclopropyl)-3-(4-[1.2.4]-triazol-1-ylphenyl-methanesulfonyl)-2(R)-(2,2,2-trifluoro-1(S)-4-fluorophenylethylamino)-propionamide;

N-(1-cyanocyclopropyl)-3-[2-(2-oxo-2,3-dihydrobenzimidazol-1-yl)ethanesulfonyl]-2(R)-(2,2,2-trifluoro-1(S)-4-fluorophenyl-ethylamino)propionamide;

N-(1-cyanocyclopropyl)-3-(5-oxo-pyrrolidin-2-ylmethanesulfonyl)-2(R)-(2,2,2-trifluoro-1(S)-4-fluorophenyl-ethylaminopropionamide;

N-(1-cyanocyclopropyl)-3-(2-fluoropyridin-3-ylmethanesulfonyl)-2(R)-(2,2,2-trifluoro-1(S)-4-fluorophenyl-ethylaminopropionamide;

N-(1-cyanocyclopropyl)-3-(3-methyloxetan-3-ylmethanesulfonyl)-2(R)-(2,2,2-trifluoro-1(S)-4-fluorophenylethylamino)propionamide;

N-(1-cyanocyclopropyl)-3-(2-phenylethanesulfonyl)-2(R)-(2,2,2-trifluoro-1(S)-4-fluorophenylethylamino)propionamide;

N-(1-cyanocyclopropyl)-3-(3,3,3-trifluoropropane-1-sulfonyl)-2(R)-(2,2,2-trifluoro-1(R)-4-fluorophenylethylamino)propionamide;

N-(1-cyanocyclopropyl)-3-(fluoropyridin-2-ylmethanesulfonyl)-2(R)-(2,2,2-trifluoro-1(S)-4-fluorophenylethylamino)propionamide;

N-(1-cyanocyclopropyl)-3-(fluoropyrazin-2-ylmethanesulfonyl)-2(R)-(2,2,2-trifluoro-1(S)-4-fluorophenylethylamino)propionamide;

N-(1-cyanocyclopropyl)-3-(difluoropyridin-2-ylmethanesulfonyl)-2(R)-(2,2,2-trifluoro-1(S)-4-fluorophenylethylamino)propionamide;

N-(1-cyanocyclopropyl)-3-(difluoropyridin-3-ylmethanesulfonyl)-2(R)-(2,2,2-trifluoro-1(S)-4-fluorophenylethylamino)propionamide;

N-(1-cyanocyclopropyl)-3-(quinolin-2-ylmethanesulfonyl)-2(R)-(2,2,2-trifluoro-1(S)-4-fluorophenylethylamino) propionamide;

N-(1-cyanocyclopropyl)-3-(benzo[1.2.5]thiadiazol-4-yl-methanesulfonyl)-2(R)-(2,2,2-trifluoro-1(S)-4-fluorophenyl-ethylamino)propionamide;

N-(1-cyanocyclopropyl)-3-(benzothiazol-2-ylmethanesulfonyl)-2(R)-(2,2,2-trifluoro-1(S)-4-fluorophenylethylamino)propionamide;

N-(1-cyanocyclopropyl)-3-(5-methylisoxazol-3-ylmethanesulfonyl)-2(R)-(2,2,2-trifluoro-1(S)-4-fluorophenyl-ethylamino)propionamide;

N-(1-cyanocyclopropyl)-3-(2-methylpropylsulfonyl)-2(R)-(2,2,2-trifluoro-1(S)-4-fluorophenylethylamino)propionamide;

N-(1-cyanocyclopropyl)-3-(cyclobutylmethanesulfonyl)-2(R)-(2,2,2-trifluoro-1(S)-4-fluorophenylethylamino)propionamide;

N-(1-cyanocyclopropyl)-3-(2,6-difluorophenylmethanesulfonyl)-2(R)-(2,2,2-trifluoro-1(S)-4-fluorophenylethylamino)propionamide;

N-(1-cyanocyclopropyl)-3-(2,4-difluorophenylmethanesulfonyl)-2(R)-(2,2,2-trifluoro-1(S)-4-fluorophenylethylamino)propionamide;

N-(1-cyanocyclopropyl)-3-(quinolin-3-ylmethanesulfonyl)-2(R)-(2,2,2-trifluoro-1(S)-4-fluorophenylethylamino)propionamide;

N-(1-cyanocyclopropyl)-3-(4,4,4-trifluorobutyl-1-sulfonyl)-2(R)-(2,2,2-trifluoro-1(S)-4-fluorophenylethylamino)propionamide;

N-(1-cyanocyclopropyl)-3-(2-trifluoromethylphenyl-methanesulfonyl)-2(R)-(2,2,2-trifluoro-1(S)-4-fluorophenylethylamino)-propionamide;

N-(1-cyanocyclopropyl)-3-(2-trifluoromethoxyphenyl-methanesulfonyl)-2(R)-(2,2,2-trifluoro-1(S)-4-fluorophenylethylamino)-propionamide;

N-(1-cyanocyclopropyl)-3-(cyclopropylmethanesulfonyl)-2(R)-(2,2,2-trifluoro-1(S)-3,5-difluorophenylethylamino)propionamide;

N-(1-cyanocyclopropyl)-3-(cyclopropylmethanesulfonyl)-2(R)-(2,2,2-trifluoro-1(S)-2,5-difluorophenylethylamino)propionamide;

N-(1-cyanocyclopropyl)-3-(2-pyridin-2-ylethanesulfonyl)-2(R)-(2,2,2-trifluoro-1(S)-4-fluorophenyl-ethylamino)propionamide;

N-(1-cyanocyclopropyl)-3-(2-pyridin-3-ylethanesulfonyl)-2(R)-(2,2,2-trifluoro-1(S)-4-fluorophenyl-ethylamino)propionamide;

N-(1-cyanocyclopropyl)-3-(quinolin-8-ylmethanesulfonyl)-2(R)-(2,2,2-trifluoro-1(S)-4-fluorophenyl-ethylamino)propionamide;

N-(1-cyanocyclopropyl)-3-(cyclopropylmethanesulfonyl)-2(R)-(2,2,2-trifluoro-1(S)-2,3-difluorophenylethylamino)propionamide;

N-(1-cyanocyclopropyl)-3-(cyclopropylmethanesulfonyl)-2(R)-(2,2,2-trifluoro-1(S)-2,4-difluorophenylethylamino)propionamide;

N-(1-cyanocyclopropyl)-3-(5-methyl-3-phenylisoxazol-4-ylmethanesulfonyl)-2(R)-(2,2,2-trifluoro-1(S)-4-fluorophenylethylamino)-propionamide;

N-(1-cyanocyclopropyl)-3-(4-methyl-2-phenyl-[1.2.3]triazol-5-ylmethanesulfonyl)-2(R)-(2,2,2-trifluoro-1(S)-4-fluorophenyl-ethylamino)-propionamide;

N-(1-cyanocyclopropyl)-3-(2-cyanophenylmethanesulfonyl)-2(R)-(2,2,2-trifluoro-1(S)-4-fluorophenyl-ethylamino)propionamide;

N-(1-cyanocyclopropyl)-3-(3-methoxycarbonylphenyl-methanesulfonyl)-2(R)-(2,2,2-trifluoro-1(S)-4-fluorophenylethylamino)-propionamide;

N-(1-cyanocyclopropyl)-3-(cyclopropylmethanesulfonyl)-2(R)-(2,2-difluoro-1(S)-4-fluorophenyl-ethylamino)propionamide;

N-(1-cyanocyclopropyl)-3-(cyclopropylmethanesulfonyl)-2(R)-(2,2,2-trifluoro-1 (RS)-2-chloropyridin-5-ylethylamino)propionamide;

N-(1-cyanocyclopropyl)-3-(pyridin-2-ylmethanesulfonyl)-2(R)-(2,2,3,3,3-pentafluoro-1(S)-4-fluorophenylpropylamino)propionamide;

N-(1-cyanocyclopropyl)-3-(1-oxopyridin-2-ylmethanesulfonyl)-2(R)-(2,2,3,3,3-pentafluoro-1(S)-4-fluorophenylpropylamino)propionamide;

N-(1-cyanocyclopropyl)-3-(pyridin-3-ylmethanesulfonyl)-2(R)-(2,2,3,3,3-pentafluoro-1(S)-4-fluorophenylpropylamino)propionamide;

N-(1-cyanocyclopropyl)-3-(1-oxopyridin-3-ylmethanesulfonyl)-2(R)-(2,2,3,3,3-pentafluoro-1(S)-4-fluorophenylpropylamino)-propionamide;

N-(1-cyanocyclopropyl)-3-(cyclopropylmethanesulfonyl)-2(R)-(2,2,3,3,3-pentafluoro-1(S)-4-fluorophenylpropylamino)propionamide;

N-(1-cyanocyclopropyl)-3-(quinoxalin-2-ylmethanesulfonyl)-2(R)-(2,2,2-trifluoro-1(S)-4-fluorophenylethylamino)propionamide;

N-(1-cyanocyclopropyl)-3-(tetrahydropyran-2RS-yl-methanesulfonyl)-2(R)-(2,2,2-trifluoro-1(S)-4-fluorophenylethylamino)-propionamide;

N-(1-cyanocyclopropyl)-3-(2,6-dichlorophenylmethanesulfonyl)-2(R)-(2,2,2-trifluoro-1(S)-4-fluorophenylethylamino)propionamide;

N-(1-cyanocyclopropyl)-3-(3-methoxycarbonylfuran-2RS-ylmethanesulfonyl)-2(R)-(2,2,2-trifluoro-1(S)-4-fluorophenylethylamino)-propionamide;

N-(1-cyanocyclopropyl)-3-(5-methylisoxazol-3-ylmethanesulfonyl)-2(R)-(2,2,3,3,3-pentafluoro-1(S)-4-fluorophenylpropylamino)-propionamide;

N-(1-cyanocyclopropyl)-3-(2,2-dimethylpropylsulfonyl)-2(R)-(2,2,2-trifluoro-1(S)-4-fluorophenylethylamino)propionamide;

N-(1-cyanocyclopropyl)-3-(pyridin-3-ylmethanesulfonyl)-2(R)-(2,2,3,3,3-pentafluoro-1(R)-4-fluorophenylpropylamino)propionamide;

N-(1-cyanocyclopropyl)-3-(ethanesulfonyl)-2(R)-(2,2,2-trifluoro-1(S)-4-fluorophenylethylamino)propionamide;

N-(1-cyanocyclopropyl)-3-(cyclopropylmethanesulfonyl)-2(R)-(2,2,2-trifluoro-1(R)-2,5-difluorophenylethylamino)propionamide;

N-(1-cyanocyclopropyl)-3-(cyclopropylmethanesulfonyl)-2(R)-(2,2,2-trifluoro-1(S)-2,6-difluorophenylethylamino)propionamide;

N-(1-cyanocyclopropyl)-3-(cyclopropylmethanesulfonyl)-2(R)-(2,2,2-trifluoro-1(R)-2,6-difluorophenylethylamino)propionamide;

N-(1-cyanocyclopropyl)-3-(cyclopropylmethanesulfonyl)-2(R)-(2,2,2-trifluoro-1(R)-2,3-difluorophenylethylamino)propionamide;

N-(1-cyanocyclopropyl)-3-(cyclopropylmethanesulfonyl)-2(R)-(2,2,2-trifluoro-1(R)-2,4-difluorophenylethylamino)propionamide;

N-(1-cyanocyclopropyl)-3-(methanesulfonyl)-2(R)-(2,2,2-trifluoro-1(S)-4-fluorophenylethylamino)propionamide;

N-(1-cyanocyclopropyl)-3-(propane-1-sulfonyl)-2(R)-(2,2,2-trifluoro-1(S)-4-fluorophenylethylamino)propionamide;

N-(1-cyanocyclopropyl)-3-(1H-indol-2-ylmethanesulfonyl)-2(R)-(2,2,2-trifluoro-1(S)-4-fluorophenylethylamino)propionamide;

N-(1-cyanocyclopropyl)-3-(cyclopropylmethanesulfonyl)-2(R)-(2,2,2-trifluoro-1(S)-2-fluorophenylethylamino)propionamide;

N-(1-cyanocyclopropyl)-3-(cyclopropylmethanesulfonyl)-2(R)-(2,2,2-trifluoro-1(R)-2-fluorophenylethylamino)propionamide;

N-(1-cyanocyclopropyl)-3-(pyridin-2-ylmethanesulfonyl)-2(R)-(2,2,2-trifluoro-1(S)-3,4-difluorophenylethylamino)propionamide;

N-(1-cyanocyclopropyl)-3 (pyridin-3-ylmethanesulfonyl)-2(R)-(2,2,2-trifluoro-1(S)-3,4-difluorophenylethylamino)propionamide;

N-(1-cyanocyclopropyl)-3-[2-(1H-indol-3-yl)ethanesulfonyl]-2(R)-(2,2,2-trifluoro-1(S)-4-fluorophenylethylamino)propionamide;
N-(1-cyanocyclopropyl)-3-(tetrahydropyran-4-ylmethanesulfonyl)-2(R)-(2,2,2-trifluoro-1(S)-4-fluorophenylethylamino)propionamide;
N-(1-cyanocyclopropyl)-3-(1-oxopyridin-2-ylmethanesulfonyl)-2(R)-(2,2,2-trifluoro-1(S)-2-fluorophenylethylamino)propionamide;
N-(1-cyanocyclopropyl)-3-(1-oxopyridin-2-ylmethanesulfonyl)-2(R)-(2,2,2-trifluoro-1(R)-2-fluorophenylethylamino)propionamide;
N-(1-cyanocyclopropyl)-3-(pyridin-2-ylmethanesulfonyl)-2(R)-(2,2,2-trifluoro-1(S)-2-fluorophenylethylamino)propionamide;
N-(1-cyanocyclopropyl)-3-(pyridin-2-yl(methanesulfonyl)-2(R)-(2,2,2-trifluoro-1(R)-2-fluorophenylethylamino)propionamide;
N-(1-cyanocyclopropyl)-3-(cyclopropylmethanesulfonyl)-2(R)-(2,2,2-trifluoro-1(S)-2,3,4-trifluorophenylethylamino)propionamide;
N-(1 cyanocyclopropyl)-3-(cyclopropylmethanesulfonyl)-2(R)-(2,2,2-trifluoro-1(R)-2,3,4-trifluorophenylethylaminopropionamide;
N-(1-cyanocyclopropyl)-3-(2,2,2-trifluoroethanesulfonyl)-2(R)-(2,2,2-trifluoro-1(S)-2-fluorophenylethylamino)propionamide;
N-(1-cyanocyclopropyl)-3-(benzisoxazol-3-ylmethanesulfonyl)-2(R)-(2,2,2-trifluoro-1(S)-2-fluorophenyl ethylamino)propionamide,
N-(1-cyano-cyclopropyl)-3-cyclopropylmethanesulfonyl-2(R)-[2,2,2-trifluoro-1(RS)-(3-hydroxy-6-methyl-pyridin-2-yl)-ethylamino]-propionamide;
N-(1-cyanocyclopropyl)-3-(2-tert-butyl-[1.3.4]-thiadiazol-5-ylmethanesulfonyl)-2(R)-(2,2,2-trifluoro-1(S)-4-fluorophenylethylamino)propionamide;
N-(1-cyanocyclopropyl)-3-(2,4,6-trifluorophenylmethanesulfonyl)-2(R)-(2,2,2-trifluoro-1(S)-4-fluorophenylethylamino)propionamide;
N-(1-cyanocyclopropyl)-3-(2-pyridin-2-ylethanesulfonyl)-2(R)-(2,2,3,3,3-pentafluoro-1(S)-4-fluorophenylpropylamino)propionamide;
N-(1-cyanocyclopropyl)-3-(1-ethyl-2,5-dioxopyrrolidin-3-ylmethanesulfonyl)-2(R)-(2,2,2-trifluoro-1(S)-4-fluorophenyl-ethylamino)propionamide;
N-(1-cyanocyclopropyl)-3-(benzisoxazol-3-ylmethanesulfonyl)-2(R)-(2,2,2-trifluoro-1(S)-4-fluorophenylethylamino)propionamide;
N-(1-cyano-cyclopropyl)-4-cyclopropylmethanesulfonyl-2(S)-[2,2,2-trifluoro-1(S)-(4-fluoro-phenyl)-ethylamino]-butyramide;
N-(1-cyano-cyclopropyl)-4-methanesulfonyl-2(S)-[2,2,2-trifluoro-1(S)-(4-fluoro-phenyl)-ethylamino]-butyramide;
4-benzenesulfonyl-N-(1-cyano-cyclopropyl)-2(S)-[2,2,2-trifluoro-1(S)-(4-fluoro-phenyl)-ethylamino]-butyramide;
N-(1-cyano-cyclopropyl)-2(S)-[2,2,2-trifluoro-1(S)-(4-fluoro-phenyl)-ethylamino]-4-(4-trifluoromethyl-benzenesulfonyl)-butyramide;
N-(1-cyano-cyclopropyl)-4-(4-methanesulfonyl-benzenesulfonyl)-2(S)-[2,2,2-trifluoro-1(S)-(4-fluoro-phenyl)-ethylamino]-butyramide;
3-(butane-1-sulfonyl)-N-(1-cyano-cyclopropyl)-2(R)-[2,2,2-trifluoro-1(S)-(4-fluoro-phenyl)-ethylamino]-propionamide;
N-(1-cyano-cyclopropyl)-3-(pentane-1-sulfonyl)-2(R)-[2,2,2-trifluoro-1(S)-(4-fluoro-phenyl)-ethylamino]-propionamide;
N-(1-cyano-cyclopropyl)-3-(hexane-1-sulfonyl)-2(R)-[2,2,2-trifluoro-1(S)-(4-fluoro-phenyl)-ethylamino]-propionamide;
N-(1-cyano-cyclopropyl)-3-(heptane-1-sulfonyl)-2(R)-[2,2,2-trifluoro-1(S)-(4-fluoro-phenyl)-ethylamino]-propionamide;
N-(1-cyano-cyclopropyl)-3-(3-phenyl-isoxazol-5-ylmethanesulfonyl)-2(R)-[2,2,2-trifluoro-1(S)-(4-fluoro-phenyl)-ethylamino]-propionamide;
N-(1-cyano-cyclopropyl)-3-(5-phenyl-oxazol-4-ylmethanesulfonyl)-2(R)-[2,2,2-trifluoro-1(S)-(4-fluoro-phenyl)-ethylamino]-propionamide;
N-(1-cyano-cyclopropyl)-3-([1,2,4]oxadiazol-3-ylmethanesulfonyl)-2(R)-[2,2,2-trifluoro-1(S)-(4-fluoro-phenyl)-ethylamino]-propionamide;
N-(1-cyano-cyclopropyl)-3-(5-phenyl-[1,2,4]oxadiazol-3-ylmethanesulfonyl)-2(R)-[2,2,2-trifluoro-1(S)-(4-fluoro-phenyl)-ethylamino]-propionamide;
N-(1-cyano-cyclopropyl)-3-(5-thiophen-2-yl-[1,2,4]oxadiazol-3-ylmethanesulfonyl)-2(R)-[2,2,2-trifluoro-1(S)-(4-fluoro-phenyl)-ethylamino]-propionamide;
N-(1-cyano-cyclopropyl)-3-(3-thiophen-2-yl-[1,2,4]oxadiazol-5-ylmethanesulfonyl)-2(R)-[2,2,2-trifluoro-1(S)-(4-fluoro-phenyl)-ethylamino]-propionamide;
N-(1-cyano-cyclopropyl)-3-(3,5-dimethyl-isoxazol-4-ylmethanesulfonyl)-2(R)-[2,2,2-trifluoro-1(S)-(4-fluoro-phenyl)-ethylamino]-propionamide;
N-(1-cyano-cyclopropyl)-3-(6-methyl-pyridin-2-ylmethanesulfonyl)-2(R)-[2,2,2-trifluoro-1(S)-(4-fluoro-phenyl)-ethylamino]-propionamide;
N-(1-cyano-cyclopropyl)-3-cyclopropylmethanesulfonyl-2(R)-[2,2,2-trifluoro-1(S)-(2,4,6-trifluoro-phenyl)-ethylamino]-propionamide;
N-(1-cyano-cyclopropyl)-3-cyclopropylmethanesulfonyl-2(R)-[2,2,2-trifluoro-1(R)-(2,4,6-trifluoro-phenyl)-ethylamino]-propionamide;
N-(1-cyano-cyclopropyl)-3-cyclopropylmethanesulfonyl-2(R)-(2,2,3,3-tetrafluoro-propylamino)-propionamide;
N-(1-cyano-cyclopropyl)-2(R)-[1-(2,4-difluoro-phenyl)-2,2,3,3,3-pentafluoro-propylamino]-3-(2-trifluoromethyl-phenylmethanesulfonyl)-propionamide;
N-(1-cyano-cyclopropyl)-2(R)-[1(S)-(2,4-difluoro-phenyl)-2,2,3,3,3-pentafluoro-propylamino]-3-(2-trifluoromethyl-phenylmethanesulfonyl)-propionamide;
N-(1-cyano-cyclopropyl)-3-[2-(2-oxo-2,3-dihydro-indol-1-yl)-ethanesulfonyl]-2(R)-[2,2,2-trifluoro-1(S)-(4-fluoro-phenyl)-ethylamino]-propionamide;
N-(1-cyano-cyclopropyl)-3-[2-(2,3-dioxo-2,3-dihydro-indol-1-yl)-ethanesulfonyl]-2(R)-[2,2,2-trifluoro-1(S)-(4-fluoro-phenyl)-ethylamino]-propionamide;
N-(1-cyano-cyclopropyl)-2(R)-[1(S)-(2,4-difluoro-phenyl)-2,2,2-trifluoro-ethylamino]-3-(4-methanesulfonyl-phenylmethanesulfonyl)-propionamide;
N-(1-cyano-cyclopropyl)-2(R)-[1(S)-(2,4-difluoro-phenyl)-2,2,2-trifluoro-ethylamino]-3-(3-methanesulfonyl-phenylmethanesulfonyl)-propionamide;
N-(1-cyano-cyclopropyl)-2(R)-[1(R)-(2,4-difluoro-phenyl)-2,2,2-trifluoro-ethylamino]-3-(3-methanesulfonyl-phenylmethanesulfonyl)-propionamide;
N-(1-cyano-cyclopropyl)-3-(2-cyano-phenylmethanesulfonyl)-2(R)-[1(R)-(2,4-difluoro-phenyl)-2,2,2-trifluoro-ethylamino]-propionamide;
N-(1-cyano-cyclopropyl)-3-(2-cyano-phenylmethanesulfonyl)-2(R)-[1(S)-(2,4-difluoro-phenyl)-2,2,2-trifluoro-ethylamino]-propionamide;

N-(1-cyano-cyclopropyl)-2(R)-[1(S)-(2,4-difluoro-phenyl)-2,2,2-trifluoro-ethylamino]-3-(2-methanesulfonyl-phenylmethanesulfonyl)-propionamide;

N-(1-cyano-cyclopropyl)-2(R)-[1(R)-(2,4-difluoro-phenyl)-2,2,2-trifluoro-ethylamino]-3-(2-methanesulfonyl-phenylmethanesulfonyl)-propionamide;

N-(1-cyano-cyclopropyl)-2(R)-[1(R)-(2,4-difluoro-phenyl)-2,2,2-trifluoro-ethylamino]-3-(4-methanesulfonyl-phenylmethanesulfonyl)-propionamide;

N-(1-cyano-cyclopropyl)-2(R)-[1(S)-(2,4-difluoro-phenyl)-2,2,2-trifluoro-ethylamino]-3-(4-trifluoromethyl-pyridin-3-ylmethanesulfonyl)-propionamide;

N-(1-cyano-cyclopropyl)-2(R)-[1(R)-(2,4-difluoro-phenyl)-2,2,2-trifluoro-ethylamino]-3-(2-trifluoromethyl-phenylmethanesulfonyl)-propionamide;

N-(1-cyano-cyclopropyl)-2(R)-[1(S)-(2,4-difluoro-phenyl)-2,2,2-trifluoro-ethylamino]-3-(2-trifluoromethyl-phenylmethanesulfonyl)-propionamide;

3-benzenesulfonyl-N-(1-cyano-cyclopropyl)-2(R)-[2,2,2-trifluoro-1(S)-(4-fluoro-phenyl)-ethylamino]-propionamide;

N-(1-cyano-cyclopropyl)-3-(2-methanesulfonyl-phenylmethanesulfonyl)-2(R)-[2,2,2-trifluoro-1(S)-(4-fluoro-phenyl)-ethylamino]-propionamide;

N-(1-cyano-cyclopropyl)-3-(4-methanesulfonyl-phenylmethanesulfonyl)-2(R)-[2,2,2-trifluoro-1(S)-(4-fluoro-phenyl)-ethylamino]-propionamide;

N-(1-cyano-cyclopropyl)-3-(3-methanesulfonyl-phenylmethanesulfonyl)-2(R)-[2,2,2-trifluoro-1(R)-(4-fluoro-phenyl)-ethylamino]-propionamide;

N-(1-cyano-cyclopropyl)-3-[2-(2-oxo-imidazolidin-1-yl)-ethanesulfonyl]-2(R)-[2,2,2-trifluoro-1(S)-(4-fluoro-phenyl)-ethylamino]-propionamide;

N-(1-cyano-cyclopropyl)-2(R)-[1(S)-(2,4-difluoro-phenyl)-2,2,2-trifluoro-ethylamino]-3-[2-(2-oxo-imidazolidin-1-yl)-ethanesulfonyl]-propionamide;

N-(1-cyano-cyclopropyl)-2(R)-[1(S)-(2,4-difluoro-phenyl)-2,2,2-trifluoro-ethylamino]-3-{2-[4-(4-fluoro-phenyl)-2-trifluoromethyl-imidazol-1-yl]-ethanesulfonyl}-propionamide;

N-(1-cyano-cyclopropyl)-3-{2-[4-(4-fluoro-phenyl)-2-trifluoromethyl-imidazol-1-yl]-ethanesulfonyl}-2(R)-[2,2,2-trifluoro-1(S)-(4-fluoro-phenyl)-ethylamino]-propionamide;

N-(1-cyano-cyclopropyl)-3-{2-[5-(4-fluoro-phenyl)-2-trifluoromethyl-imidazol-1-yl]-ethanesulfonyl}-2(R)-[2,2,2-trifluoro-1(S)-(4-fluoro-phenyl)-ethylamino]-propionamide;

N-(1-cyano-cyclopropyl)-2(R)-[2,2,2-trifluoro-1(S)-(4-fluoro-phenyl)-ethylamino]-3-[2-(2-trifluoromethyl-benzoimidazol-1-yl)-ethanesulfonyl]-propionamide;

N-(1-cyano-cyclopropyl)-2(R)-1(S)-(2,4-difluoro-phenyl)-[2,2,2-trifluoro-ethylamino]-3-[2-(2-trifluoromethyl-benzoimidazol-t-yl)-ethanesulfonyl]-propionamide;

N-(1-cyano-cyclopropyl)-3-cyclopropylmethanesulfonyl-2(R)-[2,2,2-trifluoro-1-(tetrahydro-pyran-4-yl)-ethylamino]-propionamide;

N-(1-cyano-cyclopropyl)-3-[2-(2-oxo-pyrrolidin-1-yl)-ethanesulfonyl]-2(R)-[2,2,2-trifluoro-1(S)-(4-fluoro-phenyl)-ethylamino]-propionamide;

N-(1-cyano-cyclopropyl)-3-[2-(2-oxo-pyrrolidin-1-yl)-ethanesulfonyl]-2(R)-[2,2,2-trifluoro-1(S)-(4-fluoro-phenyl)-ethylamino]-propionamide;

2(R)-[1(S)-(4-chloro-phenyl)-2,2,2-trifluoro-ethylamino]-N-(1-cyano-cyclopropyl)-3-cyclopropylmethanesulfonyl-propionamide;

N-(1-cyano-cyclopentyl)-3-(pyridin-3-ylmethanesulfonyl)-2(R)-[2,2,2-trifluoro-1(S)-(4-fluoro-phenyl)-ethylamino]-propionamide;

N-(1-cyano-cyclobutyl)-3-(pyridin-3-ylmethanesulfonyl)-2(R)-[2,2,2-trifluoro-1(S)-(4-fluoro-phenyl)-ethylamino]-propionamide;

N-(cyano-dimethyl-methyl)-3-(pyridin-3-ylmethanesulfonyl)-2(R)-[2,2,2-trifluoro-1(S)-(4-fluoro-phenyl)-ethylamino]-propionamide;

N-(1-cyano-cyclobutyl)-3-cyclopropylmethanesulfonyl-2(R)-[2,2,2-trifluoro-1(S)-(4-fluoro-phenyl)-ethylamino]-propionamide; and N-(cyano-dimethyl-methyl)-2(R)-[2,2,2-trifluoro-1(S)-(4-fluoro-phenyl)-ethylamino]-3-(4-trifluoromethyl-pyridin-3-ylmethanesulfonyl)-propionamide.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "*Protective Groups in Organic Chemistry*" John Wiley and Sons, 1999.

Compounds of Formula (I) where $R^1$, $R^2$, $R^3$, $R^4$ and $R^{4'}$ are as defined in the Summary of the Invention can be prepared by proceeding as in Reaction Scheme 1 below.

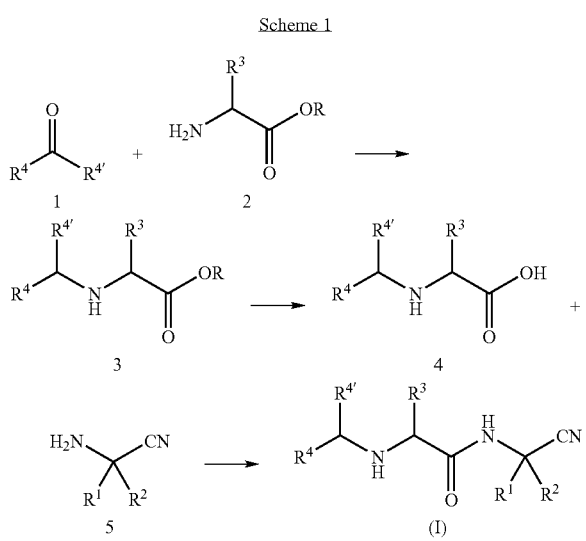

Reaction of a ketone of formula 1 where $R^4$ and $R^{4'}$ are as defined in the Summary of the Invention with an α-amino ester of formula 2 where R is a carboxy protecting group, preferably an alkyl group, preferably methyl, and $R^3$ is as defined in the Summary of the Invention under reductive amination reaction conditions provide a compound of formula 3. The reaction is carried out in the presence of a suitable dehydrating agent such as $TiCl_4$, and the like, in the presence of a base such as diisopropylethylamine, pyridine, and the like and in a suitable organic solvent such as methylene chloride to give an imine. The imine is reduced with a suitable reducing agent such as sodium borohydride, sodium cyanoborohydride, and the like in a suitable organic solvent such as methanol, ethanol, and the like.

Compounds of formula 1 such as 2,2,2-trifluoromethylacetophenone and 2,2,2,4'-tetrafluoroacetophenone commercially available. Others can be prepared by methods well known in the art. α-Amino esters of formula 2 can be prepared by methods well known in the art.

Hydrolysis of the ester group in compound 3 provides a compound of formula 4. The hydrolysis conditions depend on the nature of the protecting group. For example, when R is alkyl the hydrolysis is carried out under aqueous basic hydrolysis reaction conditions to give the corresponding acid of formula 4. The reaction is typically carried out with cesium carbonate, lithium hydroxide, and the like in an aqueous alcohol such as methanol, ethanol, and the like.

Compound 4 is then reacted with an α-aminoacetonitrile of formula 5 to give a compound of Formula (I). The reaction is typically carried out in the presence of a suitable coupling agent e.g., benzotriazole-1-yloxytrispyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC), or 1,3-dicyclohexyl-carbodiimide (DCC), optionally in the presence of 1-hydroxybenzotriazole (HOBT), and a base such as N,N-diisopropylethyl amine, triethylamine, N-methylmorpholine, and the like. The reaction is typically carried out at 20 to 30° C., preferably at about 25° C., and requires 2 to 24 h to complete. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like.

Alternatively, the above coupling step can be carried out by first converting 4 into an active acid derivative such as succinimide ester and then reacting it with an amine of formula 5. The reaction typically requires 2 to 3 h to complete. The conditions utilized in this reaction depend on the nature of the active acid derivative. For example, if it is an acid chloride derivative of 4, the reaction is carried out in the presence of a suitable base (e.g. triethylamine, diisopropylethylamine, pyridine, and the like). Suitable reaction solvents are polar organic solvents such as acetonitrile, N,N-dimethylformamide, dichloromethane, or any suitable mixtures thereof.

It will be apparent to a person skilled in the art, that compounds of Formula (I) can also be prepared by first condensing 5 with the N-protected amino acid of formula 2 where R is hydrogen followed by removal of the amino protecting group and reacting the free amino compound with a compound of formula 1 as described in Scheme 1 above. Suitable amino acid protecting groups and reaction conditions for putting them on and removing them can be found in Greene, T. W.; and Wuts, P. G. M.; *Protecting Groups in Organic Synthesis*; John Wiley & Sons, Inc. 1999.

Alternatively, a compound of Formula (I) where $R^1$, $R^2$, $R^3$, $R^4$ and $R^{4'}$ are as defined in the Summary of the Invention can be prepared as illustrated and described in Scheme 2 below.

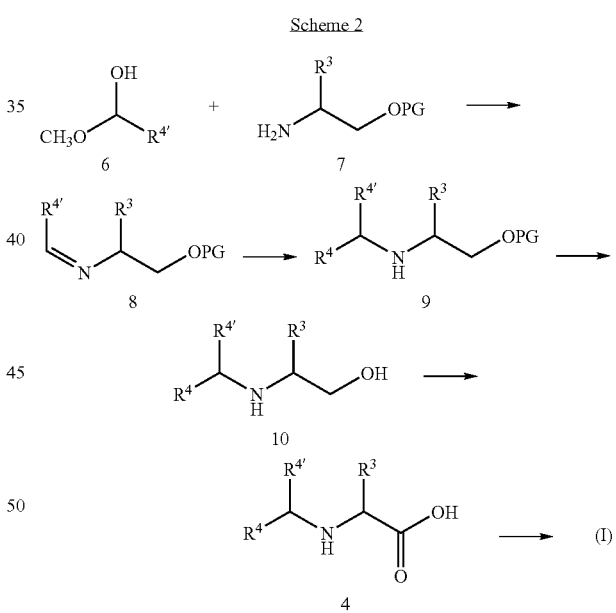

Reaction of a compound of formula 7 where $R^3$ is as defined in the Summary of the Invention and PG is a suitable oxygen protecting group with a hemiacetal of formula 6 provides an imine compound of formula 8. Treatment of 8 with an organolithium compound of formula $R^4Li$ where $R^4$ is as defined in the Summary of the Invention provides compound 9. Removal of the oxygen protecting group, followed by oxidation of the resulting alcohol 10 provides a compound of formula 4 which is then converted to a compound of Formula (I) as described in Scheme 1 above. Suitable oxygen protecting groups and reaction conditions for putting them on and removing them can be found in Greene, T. W.; and Wuts, P. G. M.; *Protecting Groups in Organic Synthesis*; John Wiley & Sons, Inc. 1999.

Alternatively, a compound of Formula (I) where $R^1$, $R^2$, $R^3$, $R^4$, and $R^{4'}$ are as defined in the Summary of the Invention and can be prepared as illustrated and described in Scheme 3 below.

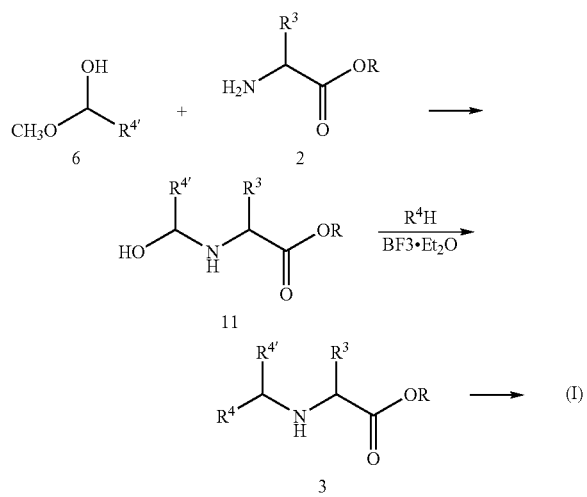

Reaction of a compound of formula 2 where R is alkyl and $R^3$ is as defined in the Summary of the Invention with a hemiacetal compound of formula 6 provides a 2-(1-hydroxy-2,2,2-trifluoroethylamino)acetate compound of formula 11. The reaction is carried out in the presence of a catalytic amount of an acid such as p-toluenesulfonic acid and in an aromatic hydrocarbon solvent such as toluene, benzene, and the like.

Treatment of 1 with a compound of formula $R^4H$ where $R^4$ is as defined in the Summary of the Invention under Friedel-Crafts reaction conditions provides a compound of formula 3 which is then converted to a compound of Formula (I) as described above.

Alternatively, the compound of Formula (I) where $R^1$, $R^2$, $R^3$, and $R^4$ are as defined in the Summary of the Invention and $R^{4'}$ is trifluoromethyl can be prepared as illustrated and described in Scheme 4 below.

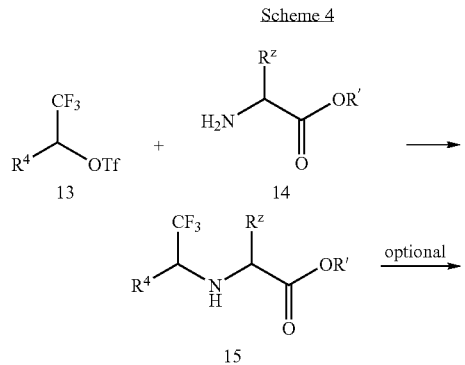

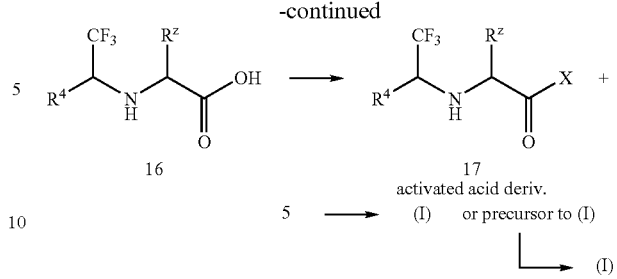

Reaction of a compound of formula 13 where $R^4$ is as defined in Summary of the Invention with a compound of formula 14 where R' is hydrogen or a carboxy protecting group and $R^z$ is $R^3$ or a precursor group (e.g., -alkylene-S-trityl or -alkylene-S-alkylene-heteroaryl) to $R^3$ group provides a compound of formula 15. The reaction is carried out in a suitable organic solvent, including but not limited to, diethyl ether, tetrahydrofuran, acetonitrile, benzene, toluene, xylene, and the like, or mixtures thereof and optionally in the presence of an organic or inorganic base. Preferably, the organic base is triethylamine, pyridine, N-methylmorpholine, collidine, diisopropylethylamine, and the like. Preferably, the inorganic base is cesium carbonate, sodium carbonate, sodium bicarbonate, and the like. The reaction is optionally carried out in the presence of a drying agent such as molecular sieves. Preferably, the reaction is carried out at room temperature.

Compounds of formula 13 can be prepared by methods well known in the art. For example, a compound of formula 13 where $R^4$ is phenyl or 4-fluorophenyl can be readily prepared from commercially available 2,2,2-trifluoroacetophenone or 2,2,2,4'-tetrafluoroacetophenone respectively, by reducing the keto group to an alcoholic group by suitable reducing agent such as sodium borohydride, lithium aluminum hydride, and the like. The solvent used depends on the type of reducing agent. For example, when sodium borohydride is used the reaction is carried out in an alcoholic organic solvent such as methanol, ethanol, and the like. When lithium aluminum hydride is used the reaction is carried out in an ethereal solvent such as tetrahydrofuran, and the like. Reaction of 2,2,2-trifluoro-1-phenylethanol or 2,2,2-trifluoro-1-(4-fluorophenyl)ethanol with triflic anhydride or trifluoromethanesulfonyl chloride provides the desired compound. Optically enriched compound of formula 15 can be obtained by reduction of the corresponding halogenated acetophenone with a suitable reducing agent such as catecholborane or $BH_3$-DMS complex in the presence of a suitable catalyst such as (S) or (R)-CBS oxazaborolidine catalyst or (S) or (R)-α,α-diphenyl-2-pyrrolidine-methanol in the presence of BBN to provide chiral alcohol which is then converted to compound 13 as described above. Compounds of formula 14 can be prepared by methods well known in the art.

Removal of the carboxy protecting group from a compound of formula 15 where R' is a protecting group provides a compound of formula 16. The conditions used to remove the carboxy protecting group depend on the nature of the carboxy protecting group. For example, if R' is alkyl, it is removed under basic hydrolysis reaction conditions utilizing aqueous base such as aqueous lithium hydroxide, sodium hydroxide, and the like in an alcoholic solvent such as methanol, ethanol, and the like. Additionally, if the $R^z$ group in compound 14 is a precursor group to $R^3$ it can be converted to $R^3$ or to another precursor group to $R^3$ (e.g., converting -alkylene-S-trityl to -alkylene-S-alkylene-heteroaryl, and the like) prior to proceeding further.

Compound 15 (where R' is hydrogen) or 16 is then converted to an activated acid derivative 17 (X is a leaving group) and which upon reaction with an aminoacetonitrile compound of formula 5 provides a compound of Formula (I) when $R^z$ is $R^3$ or a precursor compound to (I) when $R^z$ is a precursor group to $R^3$. The activated acid derivative can be prepared and then reacted with compound 5 in a stepwise manner or the acid derivative can be generated in situ in the presence of compound 5. For example, if the activated acid is acid halide it is first prepared by reacting 16 with a halogenating agent such as thionyl chloride, oxalyl, chloride and the like and then reacted with compound 5. Alternatively, the activated acid derivative is generated in situ by reacting compound 16 and 5 in the presence of a suitable coupling agent e.g., benzotriazole-1-yloxytrispyrrolidinophosphonium hexafluorophosphate (PyBOP®), O-benzotriazol-1-yl-N,N',N'-tetramethyluronium hexafluorophosphate (HBTU), O-(7-azabenzotriazol-1-yl) 1,1,3,3-tetramethyl-uronium hexafluorophosphate (HATU), 1-(3-dimethylaminopropyl)-3-ethylcarbodiimide hydrochloride (EDC), 1,3-dicyclohexyl-carbodiimide (DCC), an the like, optionally in the presence of 1-hydroxybenzotriazole (HOBT), and in the presence of a base such as N,N-diisopropylethylamine, triethylamine, N-methylmorpholine, and the like. Suitable reaction solvents are inert organic solvents such as halogenated organic solvents (e.g., methylene chloride, chloroform, and the like), acetonitrile, N,N-dimethylformamide, ethereal solvents such as tetrahydrofuran, dioxane, and the like. Alternatively, the activated acid can be reacted with $CR^1R^2(NH_2)CONH_2$ where $R^1$ and $R^2$ are as described in the Summary of the Invention, followed by conversion of the —$CONH_2$ group to the cyano group by methods well known in the art. If $R^z$ is a precursor group to $R^3$, it is converted to $R^3$ group to provide a compound of Formula (I) e.g, conversion of -alkylene-5-alkylene-heteroaryl to -alkylene-$SO_2$-alkylene-heteroaryl under oxidation reaction conditions.

A compound of Formula (I) can be converted to other compounds of Formula (I). For example:

A compound of Formula (I) containing a hydroxy group may be prepared by de-alkylation/benzylation of an alkoxy/benzyloxy substituent; those containing an acid group, by hydrolysis of an ester group; and those containing a cyano, by displacement of a bromine atom on the corresponding compounds of Formula (I). A compound of Formula (I) containing a halo group such as chloro can be converted to a corresponding compound of Formula (I) containing an methylthio by treating it with sodium thiomethoxide. The methylthio group can be oxidized to methylsulfonyl using a suitable oxidizing agent such as OXONE®. A compound of Formula (I) containing a cyano group can be converted to a corresponding carboxy containing compound by hydrolysis of the cyano group. The carboxy group, in turn, can be converted to an ester group.

A compound of Formula (I) can be prepared as a pharmaceutically acceptable acid addition salt by reacting the free base form of the compound with a pharmaceutically acceptable inorganic or organic acid. Alternatively, a pharmaceutically acceptable base addition salt of a compound of Formula (I) can be prepared by reacting the free acid form of the compound with a pharmaceutically acceptable inorganic or organic base. Inorganic and organic acids and bases suitable for the preparation of the pharmaceutically acceptable salts of compounds of Formula (I) are set forth in the definitions section of this Application. Alternatively, the salt forms of the compounds of Formula (I) can be prepared using salts of the starting materials or intermediates.

The free acid or free base forms of the compounds of Formula (I) can be prepared from the corresponding base addition salt or acid addition salt form. For example, a compound of Formula (I) in an acid addition salt form can be converted to the corresponding free base by treating with a suitable base (e.g., ammonium hydroxide solution, sodium hydroxide, and the like). A compound of Formula (I) in a base addition salt form can be converted to the corresponding free acid by treating with a suitable acid (e.g., hydrochloric acid, etc).

The N-oxides of compounds of Formula (I) can be prepared by methods known to those of ordinary skill in the art. For example, N-oxides can be prepared by treating an unoxidized form of the compound of Formula (I) with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds of Formula (I) can be prepared from the N-oxide of an appropriate starting material.

Compounds of Formula (I) in unoxidized form can be prepared from N-oxides of compounds of Formula (I) by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds of Formula (I) can be prepared by methods known to those of ordinary skill in the art (e.g., for further details see Saulnier et al. (1994), *Bioorganic and Medicinal Chemistry Letters*, Vol. 4, p. 1985). For example, appropriate prodrugs can be prepared by reacting a non-derivatized compound of Formula (I) with a suitable carbamylating agent (e.g., 1,1-acyloxyalkylcarbonochloridate, para-nitrophenyl carbonate, or the like).

Protected derivatives of the compounds of Formula (I) can be made by means known to those of ordinary skill in the art. A detailed description of the techniques applicable to the creation of protecting groups and their removal can be found in T. W. Greene, *Protecting Groups in Organic Synthesis, 3rd* edition, John Wiley & Sons, Inc. 1999.

Compounds of the present invention may be conveniently prepared or formed during the process of the invention, as solvates (e.g. hydrates). Hydrates of compounds of the present invention may be conveniently prepared by recrystalisation from an aqueous/organic solvent mixture, using organic solvents such as dioxin, tetrahydrofuran or methanol.

Compounds of Formula (I) can be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diasteromeric derivatives of compounds of Formula (I), dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, *Enantiomers, Racemates and Resolutions*, John Wiley & Sons, Inc. (1981).

Preparation of Biological Agents

In practicing this invention several processes for the generation or purification of biological agents are used. Methods for preparing the biologics are well known in the art as discussed below.

Monoclonal antibodies are prepared using standard techniques, well known in the art, such as by the method of Kohler and Milstein, *Nature* 1975, 256:495, or a modification thereof, such as described by Buck et al. 1982, *In Vitro* 18:377. Typically, a mouse or rat is immunized with the MenB PS derivative conjugated to a protein carrier, boosted and the spleen (and optionally several large lymph nodes) removed and dissociated into single cells. If desired, the spleen cells may be screened (after removal of non-specifically adherent cells) by applying a cell suspension to a plate or well coated with the antigen. B-cells, expressing membrane-bound immunoglobulin specific for the antigen, will bind to the plate, and will not be rinsed away with the rest of the suspension. Resulting B-cells, or all dissociated spleen cells, are then induced to fuse with myeloma cells to form hybridomas. Representative murine myeloma lines for use in the hybridizations include those available from the American Type Culture Collection (ATCC).

Chimeric antibodies composed of human and non-human amino acid sequences may be formed from the mouse monoclonal antibody molecules to reduce their immunogenicity in humans (Winter et al. *Nature* 1991 349:293; Lobuglio et al. *Proc. Nat. Acad. Sci. USA* 1989 86:4220; Shaw et al. *J. Immunol.* 1987 138:4534; and Brown et al. *Cancer Res.* 1987 47:3577; Riechmann et al. *Nature* 1988 332:323; Verhoeyen et al. *Science* 1988 239:1534; and Jones et al. *Nature* 1986 321:522; EP Publication No. 519,596, published Dec. 23, 1992; and U.K. Patent Publication No. GB 2,276,169, published Sep. 21, 1994).

Antibody molecule fragments, e.g., F(ab').sub.2, FV, and sFv molecules, that are capable of exhibiting immunological binding properties of the parent monoclonal antibody molecule can be produced using known techniques. Inbar et al. *Proc. Nat. Acad. Sci. USA* 1972 69:2659; Hochman et al. *Biochem.* 1976 15:2706; Ehrlich et al. *Biochem.* 1980 19:4091; Huston et al. *Proc. Nat. Acad. Sci. USA* 1988 85(16):5879; and U.S. Pat. Nos. 5,091,513 and 5,132,405, and U.S. Pat. No. 4,946,778.

In the alternative, a phage-display system can be used to expand the monoclonal antibody molecule populations in vitro. Saiki, et al. *Nature* 1986 324:163; Scharf et al. *Science* 1986 233:1076; U.S. Pat. Nos. 4,683,195 and 4,683,202; Yang et al. *J. Mol. Biol.* 1995 254:392; Barbas, III et al. *Methods: Comp. Meth Enzymol.* 1995 8:94; Barbas, III et al. *Proc. Natl. Acad. Sci. USA* 1991 88:7978.

The coding sequences for the heavy and light chain portions of the Fab molecules selected from the phage display library can be isolated or synthesized, and cloned into any suitable vector or replicon for expression. Any suitable expression system can be used, including, for example, bacterial, yeast, insect, amphibian and mammalian systems. Expression systems in bacteria include those described in Chang et al. *Nature* 1978 275:615, Goeddel et al. *Nature* 1979 281:544, Goeddel et al. *Nucleic Acids Res.* 1980 8:4057, European Application No. EP 36,776, U.S. Pat. No. 4,551,433, deBoer et al. *Proc. Natl. Acad. Sci. USA* 1983 80:21-25, and Siebenlist et al. *Cell* 1980 20:269.

Expression systems in yeast include those described in Hinnen et al. *Proc. Natl. Acad. Sci. USA* 1978 75:1929, Ito et al. *J. Bacteriol.* 1983 153:163, Kurtz et al. *Mol. Cell. Biol.* 1986 6:142, Kunze et al. *J. Basic Microbiol.* 1985 25:141, Gleeson et al. *J. Gen. Microbiol.* 1986 132:3459, Roggenkamp et al. *Mol. Gen. Genet.* 1986 202:302, Das et al. *J. Bacteriol.* 1984 158:1165, De Louvencourt et al. *J. Bacteriol.* 1983 154:737, Van den Berg et al. *Bio/Technology* 1990 8:135, Kunze et al. *J. Basic Microbiol.* 1985 25:141, Cregg et al. *Mol. Cell. Biol.* 1985 5:3376, U.S. Pat. Nos. 4,837,148 and 4,929,555, Beach et al. *Nature* 1981 300:706, Davidow et al. *Curr. Genet.* 1985 10:380, Gaillardin et al. *Curr. Genet.* 1985 10:49, Ballance et al. *Biochem. Biophys. Res. Commun.* 1983 112:284-289, Tilburn et al. *Gene* 1983 26:205-221, Yelton et al. *Proc. Natl. Acad. Sci. USA* 1984 81:1470-1474, Kelly et al. *EMBO J.* 1985 4:475-479; European Application No. EP 244,234, and International Publication No. WO 91/00357.

Expression of heterologous genes in insects can be accomplished as described in U.S. Pat. No. 4,745,051, European Application Nos. EP 127,839 and EP 155,476, Vlak et al. *J. Gen. Virol.* 1988 69:765-776, Miller et al. *Ann. Rev. Microbiol.* 1988 42:177, Carbonell et al. *Gene* 1988 73:409, Maeda et al. *Nature* 1985 315:592-594, Lebacq-Verheyden et al. *Mol. Cell. Biol.* 1988 8:3129, Smith et al. *Proc. Natl. Acad. Sci. USA* 1985 82:8404, Miyajima et al. *Gene* 1987 58:273, and Martin et al. *DNA* 1988 7:99. Numerous baculoviral strains and variants and corresponding permissive insect host cells from hosts are described in Luckow et al. *Bio/Technology* 1988 6:47-55, Miller et al. *GENETIC ENGINEERING*, Setlow, J. K. et al. eds., Vol. 8, Plenum Publishing, pp. 1986 277-279, and Maeda et al. *Nature* 1985 315:592-594.

Mammalian expression can be accomplished as described in Dijkema et al. *EMBO J.* 1985 4:761, Gorman et al. *Proc. Natl. Acad. Sci. USA* 1982 79:6777, Boshart et al. *Cell* 1985 41:521, and U.S. Pat. No. 4,399,216. Other features of mammalian expression can be facilitated as described in Ham et al. *Meth. Enz.* 1979 58:44, Barnes et al. *Anal. Biochem.* 1980 102:255, U.S. Pat. Nos. 4,767,704, 4,657,866, 4,927,762, 4,560,655 and Reissued U.S. Pat. No. RE 30,985, and in International Publication Nos. WO 90/103430, WO 87/00195.

The production of recombinant adenoviral vectors are described in U.S. Pat. No. 6,485,958.

Botulinum toxin type A can be obtained by establishing and growing cultures of *Clostridium botulinum* in a fermenter and then harvesting and purifying the fermented mixture in accordance with known procedures.

Any of the above-described protein production methods can be used to provide the biologic that would benefit from the present invention.

Pharmacology and Utility

The compounds of the invention are selective inhibitors of cysteine proteases such as cathepsin S, K, B, and/or F, and in particular cathepsin S, and accordingly are useful for treating diseases in which cysteine protease activity contributes to the pathology and/or symptomatology of the disease. For example, the compounds of the invention are useful in treating autoimmune disorders, including, but not limited to, juvenile onset diabetes, psoriasis, multiple sclerosis, pemphigus vulgaris, Graves' disease, myasthenia gravis, systemic lupus erythemotasus, rheumatoid arthritis and Hashimoto's thyroiditis, allergic disorders, including, but not limited to, asthma, allogeneic immune responses, including, but not limited to, organ transplants or tissue grafts and endometriosis.

Cathepsin S is also implicated in disorders involving excessive elastolysis, such as chronic obstructive pulmonary disease (e.g., emphysema), bronchiolitis, excessive airway elastolysis in asthma and bronchitis, pneumonities and cardiovascular disease such as plaque rupture and atheroma. Cathepsin S is implicated in fibril formation and, therefore, inhibitors of cathepsins S are of use in treatment of systemic amyloidosis.

The cysteine protease inhibitory activities of the compounds of Formula (I) can be determined by methods known to those of ordinary skill in the art. Suitable in vitro assays for measuring protease activity and the inhibition thereof by test compounds are known. Typically, the assay measures protease-induced hydrolysis of a peptide-based substrate. Details of assays for measuring protease inhibitory activity are set forth in Biological Examples 1-5, infra.

Administration and Pharmaceutical Compositions

In general, compounds of Formula (I) will be administered in therapeutically effective amounts via any of the usual and acceptable modes known in the art, either singly or in combination with one or more therapeutic agents. A therapeutically effective amount may vary widely depending on the severity of the disease, the age and relative health of the subject, the potency of the compound used and other factors. For example, therapeutically effective amounts of a compound of Formula (I) may range from about 10 micrograms per kilogram body weight (μg/kg) per day to about 100 milligram per kilogram body weight (mg/kg) per day, typically from about 100 μg/kg/day to about 10 mg/kg/day. Therefore, a therapeutically effective amount for an 80 kg human patient may range from about 1 mg/day to about 8 g/day, typically from about 1 mg/day to about 800 mg/day. In general, one of ordinary skill in the art, acting in reliance upon personal knowledge and the disclosure of this Application, will be able to ascertain a therapeutically effective amount of a compound of Formula (I) for treating a given disease.

The compounds of Formula (I) can be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula (I) in combination with at least one pharmaceutically acceptable excipient. Acceptable excipients are non-toxic, aid administration, and do not adversely affect the therapeutic benefit of the active ingredient. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, and the like). Preferred liquid carriers, particularly for injectable solutions, include water, saline, aqueous dextrose and glycols.

The amount of a compound of Formula (I) in the composition may vary widely depending upon the type of formulation, size of a unit dosage, kind of excipients and other factors known to those of skill in the art of pharmaceutical sciences. In general, a composition of a compound of Formula (I) for treating a given disease will comprise from 0.01% w to 10% w, preferably 0.3% w to 1% w, of active ingredient with the remainder being the excipient or excipients. Preferably the pharmaceutical composition is administered in a single unit dosage form for continuous treatment or in a single unit dosage form ad libitum when relief of symptoms is specifically required. Representative pharmaceutical formulations containing a compound of Formula (I) are described in Example 1 below.

EXAMPLES

The present invention is further exemplified, but not limited by, the following examples that illustrate the preparation of compounds of Formula (I) (Examples) and intermediates (References) according to the invention.

Reference A

Synthesis of trifluoromethanesulfonic acid 2,2,2-trifluoro-1-(4-fluorophenyl)ethyl ester

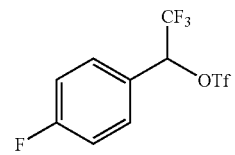

Step 1

To a stirred solution of 2,2,2,4'-tetrafluoroacetophenone (10 g, 52.1 mmol) in methanol (50 mL) was added NaBH$_4$ (0.98 g, 26.5 mmol) at 0° C. After stirring at 25° C. for 2 h, the reaction mixture was quenched by adding 1N HCl (100 mL) and then extracted with ethyl ether. The ether extract was washed with brine, dried with MgSO$_4$, and concentrated to give 2,2,2-trifluoro-1-(4-fluorophenyl)ethanol (11.32 g) which was used in next step without further purification.

Step 2

NaH (640 mg, 16 mmol, 60% in mineral oil) was washed twice with hexane (20 mL) and then suspended in dried diethyl ether (20 mL). A solution of 2,2,2-trifluoro-1-(4-fluoro-phenyl)ethanol (1.94 g, 10 mmol) in diethyl ether (10 mL) was added at 0° C. After stirring for 2 h at room temperature, a solution of trifluoromethanesulfonyl chloride (1.68 g, 10 mmol) in diethyl ether (10 mL) was added. After 2 h, the reaction mixture was quenched by adding a solution of sat NaHCO$_3$ and the product was extracted with diethyl ether. The extracts were washed with brine and dried, and the solvent was removed to yield trifluoromethanesulfonic acid 2,2,2-trifluoro-1-(4-fluorophenyl)ethyl ester (3.3 g).

Reference B

Synthesis of 2,2,2-trifluoro-1(R)-(4-fluorophenyl)ethanol

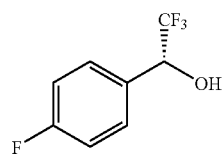

To a −78° C. toluene (25 mL)/dichloromethane (25 mL) solution of 2,2,2,4'-tetrafluoroacetophenone (2.5 g, 13.01 mmol) and 1M S-methyl CBS oxazaborolidine catalyst (1.3 mL, 1.3 mmol) was added freshly distilled catecholborane (1.66 mL, 15.62 mmol). The reaction mixture was maintained at −78° C. for 16 h at which time 4N HCl (5 mL in dioxane) was added and the reaction mixture was allowed to warm to room temperature. The reaction mixture was diluted with ethyl acetate and washed with a saturated brine solution. The organic layer was dried over magnesium sulfate, filtered and concentrated to provide a solid. The solid was suspended in hexanes and filtered off. The hexanes filtrate containing the desired product was concentrated and the residue subjected to flash chromatography (hexanes:ethylacetate 1:10) to provide the title compound as a colorless oil (2.2 g, 87% yield). The ratio of enantiomers was determined to be 95:5 by chiral HPLC (Chiralcel OD column, 95 hexanes:5 isopropanol mobile phase. Ret. time of the major product was 6.757 min. Ret. Time for the minor isomer was 8.274 min.).

2,2,2-Trifluoro-1(S)-(4-fluorophenyl)ethanol can be prepared by using R-methyl CBS oxazaborolidine.

Reference C

Synthesis of 1-aminocyclopropanecarbonitrile hydrochloride

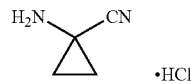

Step 1

A mixture of benzophenone imine (25 g, 0.138 mol, Aldrich) and aminoacetonitrile hydrochloride (25 g, 0.270 mol, Lancaster) in dichloromethane (1000 mL) was stirred in a 2 L Erlenmeyer flask under nitrogen at room temperature for 5 days. The reaction mixture was filtered to remove the precipitated ammonium chloride and the filtrate was evaporated to dryness in vacuo. The resulting residue was dissolved in ether (400 mL) washed with water (200 mL) and brine. After drying over magnesium sulfate the solution was evaporated to give (benzhydrylideneamino)-acetonitrile (47.89 g).

Step 2

A solution of sodium hydroxide (91 g, 2.275 mol) in water (91 mL) in a 2 L flask was cooled on ice under nitrogen and then treated with benzyl triethyl ammonium chloride (2.0 g, 0.0088 mol, Aldrich) and (benzhydrylideneamino)acetonitrile (47.89 g) in toluene (100 mL).

1,2-Dibromoethane (23 mL, 122.4 mmol, Aldrich) was then added dropwise over 25 min, to the reaction mixture with mechanical stirring and cooling to maintain the internal temperature near +10° C. The reaction mixture was then stirred vigorously for 24 h at room temperature and then poured into ice water and extracted with toluene. The combined extracts were washed with brine and then treated with MgSO$_4$ and Norite. After filtering, toluene was removed by rotary evaporation to give an oil (67 g). The residue was dissolved in boiling hexane (400 mL), treated with Norite and filtered hot and allowed to cool. A dark oil separated which was removed by pipette (~2 mL). Scratching induced crystallization in the remaining solution which was cooled on ice for 2 h. Light yellow crystals were collected by filtration and washed with cold hexane to give 1-(benzhydrylideneamino)cyclopropanecarbonitrile (30.56 g).

Step 3

A mixture of 1-(benzhydrylideneamino)cyclopropanecarbonitrile (30.56 g, 0.124 mol) in concentrated HCl (12 mL) in water (100 mL) and ether (100 mL) was stirred at room temperature for 15 h. The ether layer was discarded and the aqueous layer was washed with ether. The aqueous layer was then freeze dried to give the title compound as a tan powder (13.51 g). This compound is also commercially available.

Reference D

Synthesis of 2(R)-[2,2,2-trifluoro-1(S)-(4-fluorophenyl)ethylamino]-3-tritylsulfanyl-propionic acid

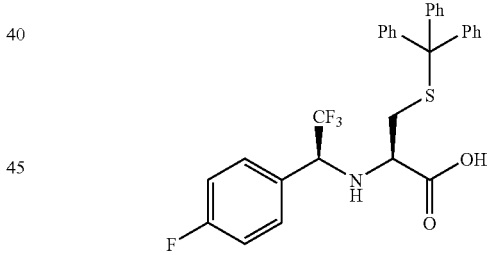

To a slurry of S-trityl-L-cysteine (4.86 g, 13.37 mmol) in dichloromethane (97 mL, 20 mL/g AA) at room temperature was added diisopropylethylamine (9.32 mL, 53.48 mmol) followed by a solution of trifluoromethanesulfonic acid 2,2,2-trifluoro-1 (RS)-phenylethyl ester (5.32 g, 16.04 mmol) (major enantiomer (S), 90 ee) in dichloromethane (15 mL) via syringe all at once. After 19 h, the reaction mixture was concentrated on the rotovap to give an oil. Diethyl ether was added and the solution was washed with 1N HCl and brine. The organic layer was dried over MgSO$_4$, filtered, and concentrated. Flash chromatography of the residue with 2 hexanes/1 ethyl acetate/0.25% acetic acid as the eluent provided 2(R)-[2,2,2-trifluoro-1(S)-(4-fluorophenyl)ethylamino]-3-tritylsulfanyl-propionic acid (6 g) (major diastereomer (R,S), 90 de) as an oil/foam.

Reference E

Synthesis of 2(R)-amino-3-cyclopropylmethylsulfanylpropan-1-ol

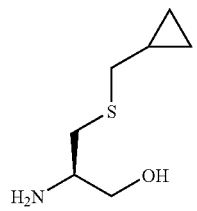

Step 1

An ice water bath cooled solution of L-cysteine in 1N sodium hydroxide (740 mL) and dioxane (740 mL) was treated with bromomethylcyclopropane (50 g, 370 mmol). The reaction mixture was allowed to warm to room temperature and stirred for 16 h. Dioxane was removed under reduced pressure and the resulting aqueous solution was adjusted to pH 6 with 6N HCl and placed in a refrigerator for 20 h. The product was collected by vacuum filtration, washed with hexanes and lyophilized to give 2(R)-amino-3-cyclopropylmethylsulfanylpropionic acid (57.28 g) as a white solid.

Step 2

To an ice water cooled solution of lithium aluminum hydride (200 mL of 1.0 M) was added solid 2(R)-amino-3-cyclopropylmethylsulfanylpropionic acid. The addition was done by tapping in portions through a funnel in such a manner as to control hydrogen gas evolution. The ice bath was removed, and the reaction mixture was heated at reflux for 16 h. The reaction mixture was removed from heat and cooled in an ice water bath. Diethyl ether (110 mL) was added, followed by dropwise addition of water (5 mL), 15% aqueous sodium hydroxide (5 mL), and water (15 mL). After stirring in the ice water bath for 1.5 h, the reaction mixture was filtered. The filtrate was dried over anhydrous sodium sulfate, and concentrated to give 2(R)-amino-3-cyclopropylmethylsulfanyl-propan-1-ol (14.9 g).

Example 1

Synthesis of N-(1-cyanocyclopropyl)-3-pyridin-3-ylmethanesulfonyl-2(R)-(2,2,2-trifluoro-1(S)-4-fluorophenylethylamino)propanamide; (compound 2)

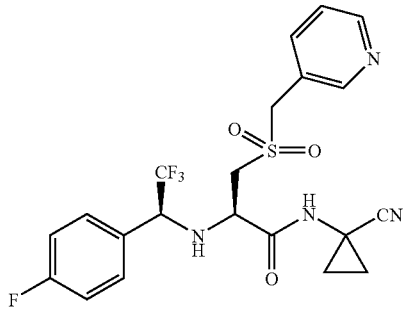

Step 1

To a solution of 2(R)-[2,2,2-trifluoro-1(S)-(4-fluorophenyl)ethylamino]-3-trityl-sulfanylpropionic acid (539 mg, 1 mmol, 90% de), prepared as described above, in $CH_2Cl_2$ was added trifluoroacetic acid (0.4 mL, 4 mmol) and triethylsilane (0.4 mL, 2 mmol) at 0° C. under nitrogen atmosphere. The reaction mixture was warmed up to room temperature and stirred for 2 h. The solvent was removed under reduced pressure and the residue was dissolved in 1N NaOH (12 mL). The aqueous layer was washed with hexane and to the basic solution was added dioxane (12 mL), $P(CH_2CH_2COOH)_3 \cdot HCl$ (28 mg, 0.1 mmol) and 3-chloromethyl-pyridine (196 mg, 1.2 mmol) and the reaction mixture was stirred at room temperature 2 h. The dioxane was removed under educed pressure and residue was acidified with 6N HCl to pH 5. The product was extracted with ethyl acetate and after drying the organic extracts with $MgSO_4$, the solvent was removed to give 2(R)-[2,2,2-trifluoro-1(S)-(4-fluorophenyl)ethyl-amino]-3-(pyridin-3-ylmethylsulfanyl)propionic acid which was used in the next step without further purification.

Step 2

2(R)-[2,2,2-trifluoro-1(S)-(4-fluorophenyl)ethylamino]-3-(pyridin-3-ylmethylsulfanyl)-propionic acid was dissolved in DMF (5 mL) and 1-aminocyclopropanecarbonitrile (142 mg, 1.2 mmol), HATU (456 mg, 1.2 mmol) and NMM (0.44 mL, 4 mmol) were added. After stirring for 2 h at rt, saturated $NH_4Cl$ and ethyl acetate were added and stirring was continued for 20 min. The aqueous layer was extracted with ethyl acetate. The combined organic layers were dried with $MgSO_4$ and the solvent was removed under the reduced pressure to give N-(1-cyanocyclopropyl)-2(R)-[2,2,2-trifluoro-1(S)-(4-fluorophenyl)ethylamino]-3-(pyridin-3-ylmethylsulfanyl) propionamide as an oil. The crude was used in the next step without further purification.

Step 3

N-(1-cyanocyclopropyl)-2(R)-[2,2,2-trifluoro-1(S)-(4-fluorophenyl)ethylamino]-3-(pyridin-3-ylmethylsulfanyl) propionamide was dissolved in MeOH (3 mL) and OXONE® (460 mg, 1.5 mmol) in $H_2O$ (3 mL) was added. After stirring at rt for 2 h, the solvent was removed and the residue was extracted with ethyl acetate. The organic layer was dried with $MgSO_4$ and the solvent was removed under reduced pressure. The title compound was purified by Prep-HPLC.

Example 2

Synthesis of N-(1-cyanocyclopropyl)-3-(difluoropyridin-2-ylmethanesulfonyl)-2(R)-[2,2,2-trifluoro-1(S)-(4-fluorophenyl)ethylamino]propionamide (compound 23)

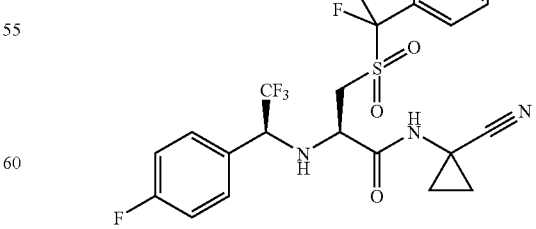

Step 1

To a solution of (Boc-Cys-OH)$_2$ (20 g, 45.4 mmol) and $P(CH_2CH_2COOH)_3 \cdot HCl$ (15.61 g, 54.47 mmol) in DMF (162 mL) was added 5N KOH (109 mL) slowly over 20 min. After stirring overnight, 2-picolylchloride hydrochloride (22.34 g, 136.2 mmol) was added in one portion and the reaction mixture was stirred at room temperature for 2.5 h. The pH of the solution was adjusted to 3 with 10N HCl and the product was extracted with methylene chloride. The combined organic extract was washed with sat. NaHCO$_3$, dried over MgSO$_4$, filtered and concentrated to give 2(R)-N-tert-butoxycarbonylamino-3-(pyridin-2-ylmethylsulfanyl)propionic acid which was crystallized from methylene chloride and hexane mixture to give pure product (13.70 g) as a white solid.

Step 2

2(R)-N-tert-Butoxycarbonylamino-3-(pyridin-2-ylmethylsulfanyl)propionic acid (3.12 g, 10 mmol) was dissolved in mixture of methanol (10 mL) and benzene (10 mL). Trimethylsilyl-diazomethane (10 mL, 2.0M solution in hexane, 20 mM) was added slowly. After 1 h, the solvent was removed to give methyl 2(R)-N-tert-butoxycarbonylamino-3-(pyridin-2-ylmethyl-sulfanyl)-propionate as a yellow oil.

Step 3

Methyl 2(R)-N-tert-butoxycarbonylamino-3-(pyridin-2-ylmethylsulfanyl)-propionate was dissolved in dioxane and 3 equiv. of 4M HCl in dioxane was added. After stirring at room temperature for 3 h, the solvent was removed under reduced pressure to give methyl 2(R)-amino-3-pyridin-2-ylmethylsulfanyl)propionate hydrochloride as a hygroscopic solid.

Step 4

To a mixture of methyl 2(R)-amino-3-(pyridin-2-ylmethylsulfanyl)propionate hydrochloride (1.31 g, 5 mmol), 2,2,2-trifluoro-1-(4-fluorophenyl)ethanone (0.875 g), DIPEA (2.39 g, 18.5 mmol), in dichloromethane (20 mL) was added titanium tetrachloride (4.65 mmol) dropwise over 5 min. After stirring for 3 h at ambient temperature, additional titanium tetrachloride (0.3 mmol) was added. After an additional hour of stirring, NaCNBH$_4$ (0.973 g, 15.5 mmol) was added in methanol (10 mL). After 1 h, the reaction mixture was diluted with ethyl acetate (200 mL) and poured onto magnesium sulfate. After filtration and concentration, the residue was purified by flash chromatography to afford methyl 3-(pyridin-2-yl-methylsulfanyl)-2(R)-[2,2,2-trifluoro-1(RS)-(4-fluorophenyl)ethylamino]-propionate (640 mg, 1.59 mmol).

Step 5

To a solution of methyl 3-pyridin-2-ylmethylsulfanyl-2(R)-[2,2,2-trifluoro-1(RS)-(4-fluorophenyl)ethylamino]propionate (0.64 g, 1.59 mmol) in methanol (9 mL) was added 1N sodium hydroxide (4.77 mL). The resulting solution was stirred for 2 h at ambient temperature and then methanol was removed in vacuo. The residue was portioned between water and ethyl acetate. The aqueous layer was extracted twice more with ethyl acetate and the combined organic layers were dried over magnesium sulfate. Removal of the solvents provided 3-(pyridin-2-ylmethylsulfanyl)-2(R)-[2,2,2-trifluoro-1(RS)-(4-fluorophenyl)ethylamino]propionic acid (0.410 g, 1.06 mmol) as a white solid which was a mixture of diastereomers.

3-(Pyridin-2-ylmethylsulfanyl)-2(R)-[2,2,2-trifluoro-1(RS)-(4-fluorophenyl)ethylamino]-propionic acid was converted to of N-(1-cyanocyclopropyl)-3-(pyridin-2-ylmethylsulfanyl)-2(R)-[2,2,2-trifluoro-1(RS)-(4-fluorophenyl) ethylamino]propionamide by proceeding as described in Example 1, Step 2 above. N-(1-Cyanocyclopropyl)-3-pyridin-2-ylmethanesulfanyl-2(R)-(2,2,2-trifluoro-1(S)-4-fluorophenylethylamino)propionamide (95 mg) was obtained from the diasteriomeric mixture by flash chromatography and was converted to N-(1-cyano-cyclopropyl)-3-pyridin-2-yl-methanesulfonyl-2(R)-(2,2,2-trifluoro-1(S)-4-fluorophenyl-ethyl-amino)propionamide compound (50 mg) by proceeding as described in Example 1, Step 3 above.

Step 6

To N-(1-cyanocyclopropyl)-3-pyridin-2-ylmethanesulfonyl-2(R)-(2,2,2-trifluoro-1(S)-4-fluorophenylethylamino) propionamide (0.200 g, 0.412 mmol) in dichloromethane (5 mL) was added DIPEA (0.058 g, 4.53 mmol) and the slight suspension cooled in an ice-water bath. Boc-anhydride (0.099 mg, 0.453 mmol) was added in one portion and the resulting opaque solution was allowed to warm to ambient temperature overnight. The reaction was diluted to 100 mL with EtOAc and the organic phase extracted once with 10 mL 0.1 N HCl, sodium bicarbonate, and brine and dried over MgSO$_4$. Removal of solvent afforded [1(R)-(1-cyanocyclopropyl-carbamoyl)-2-pyridin-2-ylmethanesulfonyl)ethyl]-[2,2,2-trifluoro-1(S)-(4-fluorophenyl)-ethyl]carbamic acid tert-butyl ester (0.200 g) as a white solid, which was used without further purification.

Step 7

To a 0.5M solution of potassium bis(trimethylsilyl)amide (1.02 mmol) in toluene, cooled to –78° C., was added [1(R)-(1-cyanocyclopropylcarbamoyl)-2-(pyridin-2-ylmethane-sulfonyl)-ethyl]-[2,2,2-trifluoro-1(S)-(4-fluorophenyl)ethyl] carbamic acid tert-butyl ester (0.2 g, 0.34 mmol) in THF (2 mL) and the brown solution was stirred for 40 min at –78° C. MnBr$_2$ was added as a solid, in one portion, resulting in a brown suspension. After stirring for 30 min, (PhSO$_2$)$_2$NF (0.304 g, 0.964 mmol) was added as a solid and the reaction mixture was stirred at –78° C. for 30 min, then allowed to warm to ambient temperature overnight. After partitioning between 0.5 N HCl and EtOAc the organic phase was extracted with bicarbonate, brine, and dried over MgSO$_4$. The crude residue was purified via flash chromatography with EtOAc/hexanes (0 to 40% EtOAc gradient) affording the title compound. MS: 519.2, (M–1) 543.1 (M+23). Also, 1N-(1-cyanocyclopropyl)-3-(fluoropyridin-2-ylmethanesulfonyl)-2(R)-[2,2,2-trifluoro-1(S)-(4-fluorophenyl)ethylamino]propionamide was isolated as a diastereomeric mixture.

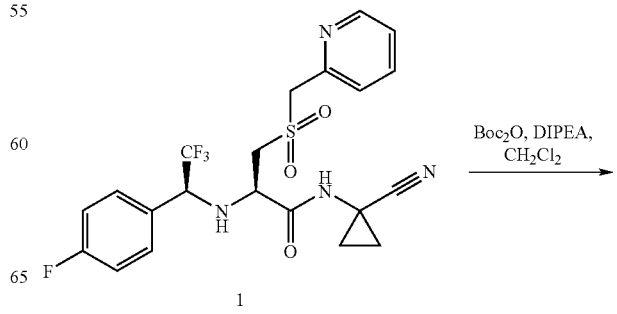

1

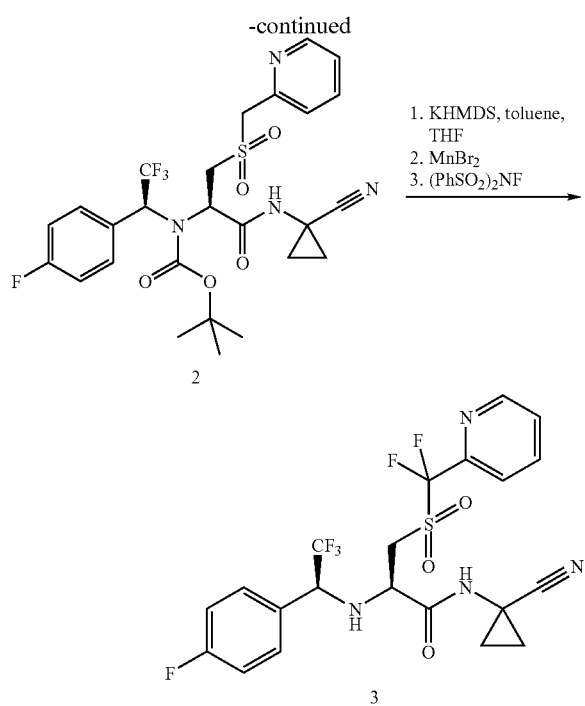

Example 3

Synthesis of N-(1-cyanocyclopropyl)-3-(cyclopropylmethanesulfonyl)-2(R)-(2,2-difluoro-1(S)-4-fluorophenylethylamino)propionamide; (compound 48)

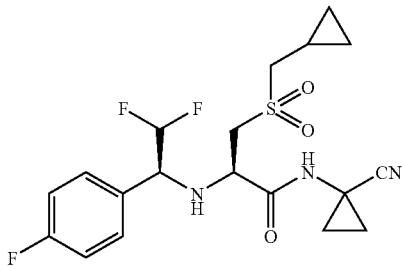

Step 1

A solution of 2(R)-amino-3-cyclopropylmethylsulfanyl-propan-1ol (4.9 g, 30.4 mmol), difluoroacetaldehyde ethyl hemiacetal (4.6 g, 36.5 mmol), and PPTS (415 mg) in toluene (100 mL) was heated at reflux with Dean Stark trapping of water for 4 h. After cooling to ambient temperature, the solution was filtered through a pad of silica gel and concentrated to an oil. The oil was further purified via silica gel chromatography with 1:1 (v/v) hexanes:diethyl ether as the elution solvent. Concentration of the appropriate fractions yielded a diastereomeric mixture of 4-cyclopropylmethylsulfanylmethyl-2-difluoromethyloxazolidine (4.2 g) as a clear oil.

Part A:

A solution of 4-cyclopropylmethylsulfanylmethyl-2-difluoromethyloxazolidine (2.08 g, 9.3 mmol) in anhydrous THF (25 mL) was cooled in an ice/water bath and treated with chlorotrimethylsilane (1.2 g, 1.4 mL) and lithium bis(trimethylsilyl)amide (11.2 mL of a 1.0 M solution in tetrahydrofuran). The reaction mixture was allowed to stir under ice bath cooling for 30 min and then slowly heated to 60° C. for 1 h to ensure complete equilibration to the E imine isomer. The reaction mixture containing (2-cyclopropylmethylsulfanyl-1-trimethylsilanyloxy-methylethyl)-(2,2-difluoroethylidene)amine was allowed to cool to room temperature.

Part B:

A solution of 4-fluorobromobenzene (4.9 g, 27.9 mmol) in anhydrous tetrahydrofuran (55 mL) was cooled to −78° C., treated with 17-butyllithium (11.15 mL of 2.5 M solution in hexanes) and allowed to stir for 15 min. The solution from Part A was transferred by syringe to this reaction mixture at −78° C. over 10 min. Stirring at −78° C. for 2 h was followed by addition of aq 2.5 N HCl (10 mL), then the reaction mixture was allowed to warm to room temperature and stirred at room temperature for 30 min. Potassium hydroxide (9 mL of 25% solution in water) was added and the reaction mixture was extract 2 times with 100 mL portions of diethyl ether. The combined organic layers were dried over $MgSO_4$, concentrated, and chromatographed using 20% ethyl acetate:80% hexanes (v/v) as the elution solvent. Concentration of the appropriate fractions yielded 3-cycloproplymethylsulfanyl-2(R)-[2,2-difluoro-1(S)-(4-fluorophenyl)-ethylamino]propan-1-ol (1.45 g) as a clear oil.

Step 3

A stock solution of $H_5IO_6/CrO_3$ was prepared as described in Tet. Lett. 1998 39(30) pp. 5323-5326. This was done by dissolving $H_5IO_6$ (11.4 g, 50 mmol) and $CrO_3$ (56 mg, 2.4 mol %) in anhydrous acetonitrile (115 mL) and stirred overnight. The next morning 855 μL of water was added to the stock solution and stirred for an additional 10 min. $H_5IO_6/CrO_3$ (53 mL) of the stock solution was chilled to 0° with stirring, and a solution of 3-cycloproplymethylsulfanyl-2(R)-[2,2-difluoro-1(S)-(4-fluorophenyl)ethylamino]propan-1-ol (1.45 g) in acetonitrile (25 mL) was added dropwise so as to maintain the reaction temperature at 0° C. After 4 h, isopropanol (50 mL) was added. The reaction mixture was allowed to warm to room temperature and then was concentrated. The resulting solids were partitioned between ethyl acetate and saturated aqueous $KH_2PO_4$. The aqueous layer was dried over anhydrous $MgSO_4$. Removal of solvent gave 3-cyclopropylmethylsulfonyl-2(R)-[2,2,-difluoro-1(S)-(4-fluoro-phenyl)ethylamino]-propionic acid (0.95 g).

Step 4

To a solution of 3-cyclopropylmethylsulfonyl-2(R)-[2,2,-difluoro-1(S)-(4-fluorophenyl)-ethylamino]propionic acid (0.95 g), 1-aminocyclopropanecarbonitrile HCl salt (400 mg) in DMF (5 mL) at room temperature was added HATU (1.28 g), followed by diisopropylethylamine (1.68 g/2.26 mL). After being stirred at room temperature for 4 hours, the reaction mixture was concentrated under reduced pressure and then partitioned between ethyl acetate and brine. The combined organic extracts were dried over anhydrous $MgSO_4$ and concentrated under reduced pressure, and the residue was purified by recrystallization from 2-propanol to yield N-(1-cyano-cyclopropyl)-3-cyclopropylmethanesulfonyl-2-[2,2-difluoro-1-(4-fluorophenyl)ethylamino]-propionamide as colorless crystals (250 mg).

$^1$H NMR sample acquired in $d_6$-dimethylsulfoxide is referenced to residual $CD_3SOCD_2H$ at 2.49 ppm. $^1$H NMR (400 MHz): δ 8.97 (s, 1H), 7.4-7.35 (m, 2H), 7.21-7.16 (m, 2H), 6.09 (dt, 1H), 3.98 (m, 1H), 3.53 (m, 1H), 3.40 (m, 1H), 3.26-3.20 (m, 2H), 3.17-3.11 (m, 2H), 1.38 (m, 1H), 1.08 (m, 1H), 0.99 (m, 1H), 0.80 (m, 1H), 0.6 (m, 2H), 0.38 (m, 2H)

13C NMR Sample acquired in d6-dimethylsulfoxide is referenced to residual 13CD3SOCD3 at 39.5 ppm. 13C NMR (125 MHz): δ 172.16, 163.04, 161.09, 132.12, 130.66, 130.59, 120.37, 118.24, 116.31, 115.28, 115.11, 114.37, 62.11, 61.94, 61.76, 58.58, 55.12, 54.38, 19.53, 15.49, 15.45, 3.95, 3.82, 3.78. Exact Mass for $C_{19}H_{22}F_3N_3O_3S$=429.1. Electrospray HPLC/MS M+H=430.1, M-H=428.2

Example 4

Synthesis of N-(1-cyanocyclopropyl)-3-(4-trifluoromethylpyridin-3-ylmethanesulfonyl)-2(R)-(2,2,2-trifluoro-1 (S)-4-fluorophenylethylamino)-propionamide (compound 1)

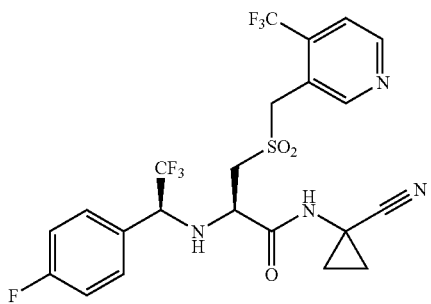

Step 1

4-Trifluoromethylnicotinic acid (2 g, 10.4 mmol) was dissolved in THF and BH3-THF 1.0M complex (50 mL, 50 mmol) was added at room temperature under N2. The reaction mixture was stirred at room temperature overnight. 6N HCl was added slowly to quench the reaction. Solvent was removed under reduced pressure and the aqueous layer was adjusted to pH 5 and extracted with ethyl acetate. The combined organic layers were dried with MgSO4, filtered and concentrated under the reduced pressure. The crude (4-trifluoromethylpyridin-3-yl)methanol was dissolved in CH2Cl2 and SOCl2 (2.2 mL, 30 mmol) was added at room temperature. The reaction mixture was stirred at room temperature overnight. The solvent was removed under the reduced pressure and the crude 3-chloromethyl-4-trifluoromethylpyridine was used without further purification.

Step 2

Catecholborane (19.4 mL, 182 mmol) in dichloromethane 15 mL) was added to a dichloromethane solution of S-methyl CBS oxazaborolidine (13 mL, 13 mmol) and 2,2,2,4'-tetrafluoroacetopheone (18.2 mL, 130.13 mmol) dropwise at −78° C. in 30 min and stirred at −78° C. overnight. The reaction mixture was quenched by addition of 4N HCl in dioxane (13 mL) at −78° C., warmed up to room temperature and the solvent was removed under reduced pressure. 10% NaHSO3 solution (200 mL) was added and the aqueous layer was extracted with hexane. The organic layer was washed with water and dried with MgSO4. The solvent was removed under reduced pressure to give 2,2,2-trifluoro-1-(4-fluorophenyl)ethanol (20 g) as colorless oil (90% d.e.).

Step 3

NaH (11.87 g, 296.7 mmol) was added to Et2O (700 mL) at 0° C. under N2 and a solution of 2,2,2-trifluoro-1-(4-fluorophenyl)ethanol (44.3 g, 228.2 mmol) in ether was added at 0° C. under N2. The reaction mixture was stirred 10 min at 0° C. then 1 h at room temperature. Trifluoromethanesulfonyl chloride (50 g, 296.7 mmol) in Et2O was added at 0° C. under N2 and the reaction mixture was stirred 10 min at 0° C. and then 3 h at room temperature. The solvent was removed under the reduced pressure and H2O (100 mL) was added slowly. The aqueous layer was extracted by hexane and the combined organic layer was dried with MgSO4. The solvent was removed under the reduced pressure to give trifluoromethanesulfonic acid 2,2,2-trifluoro-1-(4-fluorophenyl) ethyl ester (70 g, 90% d.e) as colorless oil.

Step 4

2-Amino-3-tritylsulfanylpropionic acid (78 g, 214.6 mmol) was dissolved in CH2Cl2, DIPEA (112 mL, 643.8 mmol) was added and the reaction mixture was stirred for 10 min at room temperature. Trifluoromethanesulfonic acid 2,2,2-trifluoro-1-(4-fluorophenyl)ethyl ester (70 g, 214.6 mmol) in CH2Cl2 was added and the reaction mixture was stirred at room temperature overnight. Solvent was removed under reduced pressure, the residue was dissolved in Et2O and the solution was washed with 1N HCl, brine, and dried with MgSO4. Solvent was removed to give a mixture of 2(R)-[2,2,2-trifluoro-1(S)-(4-fluorophenyl)ethylamino]-3-tritylsulfanyl-propionic acid and 2(R)-[2,2,2-trifluoro-1(R)-(4-fluorophenyl)ethylamino]-3-tritylsulfanyl-propionic acid (90 g, 90% de) as yellow solid.

Step 5

A mixture of 2(R)-[2,2,2-trifluoro-1(S)-(4-fluorophenyl) ethylamino]-3-tritylsulfanyl-propionic acid and 2(R)-[2,2,2-trifluoro-1(R)-(4-fluorophenyl)ethylamino]-3-tritylsulfanyl-propionic acid (5.4 g, 10 mmol) was dissolved in CH2Cl2, TFA (3.1 mL, 40 mmol) and Et3SiH (3.2 mL, 20 mmol) were added at 0° C. under N2. The reaction mixture was warmed up to room temperature and stirred for 2 h. Solvent was removed under reduced pressure and the residue was dissolved in 120 mL of 1N NaOH. The aqueous layer was washed with hexane and used in the next step without further purification. To the aqueous solution was added dioxane (120 mL), 3-chloromethyl-4-trifluoromethylpyridine (1.95 g, 10 mmol), and tris (2-carboxyethyl)phosphine hydrochloride (280 mg, 1 mmol). The reaction mixture was stirred at room temperature overnight. Dioxane was removed under the reduced pressure. The aqueous solution was adjusted to pH 3 and was extracted with ethyl acetate. The combined organic layer was dried with MgSO4 and removed under the reduced pressure. The crude product 2(R)-[2,2,2-trifluoro-1(S)-(4-fluorophenyl)ethylamino]-3-(4-trifluoromethylpyridin-3-ylmethylsulfanyl)-propionic acid containing minor amounts of other diasteromer was used in the next step without further purification.

Step 6

2(R)-[2,2,2-Trifluoro-1(S)-(4-fluorophenyl)ethylamino]-3-(4-trifluoromethylpyridin-3-ylmethylsulfanyl)-propionic acid, 1-aminocyclopropanecarbonitrile hydrochloride (1.18 g, 10 mmol), HATU (4.56 g, 12 mmol), and NMM (4.4 mL, 40 mmol) were added to DMF and the reaction mixture stirred at room temperature for 2 h. Sat. NH4Cl (10 mL) and ethyl acetate (10 mL) were added and stirring was continued for 20 min at room temperature. The aqueous layer was extracted with ethyl acetate. The combined organic layer was washed with brine and dried over MgSO4. Solvent was removed under reduced pressure and crude product N-(1-cyanocyclopropyl)-2(R)-[2,2,2-trifluoro-1(S)-(4-fluoro-phenyl)-ethylamino]-3-(4-trifluoromethyl-pyridin-3-ylmethylsulfanyl) propionamide was used in the next step without further purification.

Step 7

N-(1-cyanocyclopropyl)-2(R)-[2,2,2-trifluoro-1(S)-(4-fluorophenyl)ethylamino]-3-(4-trifluoromethyl-pyridin-3-ylmethylsulfanyl)-propionamide was dissolved in CH$_3$OH (10 mL) and an aqueous solution of Oxone® (3 g in 10 mL H$_2$O, 10 mmol) was added. The reaction mixture was stirred at room temperature 3 h. Solvent was removed under the reduced pressure. The aqueous layer was extracted with ethyl acetate. The organic layer was washed with brine and dried with MgSO$_4$. The solvent was removed under the reduced pressure and the crude product was purified by prep-HPLC to isolate the title compound from the diastereomeric mixture.

$^1$H-NMR (DMSO-d$_6$): δ 0.83 (m, 1H), 1.07 (m, 1H), 1.39 (m, 2H), 3.74 (m, 2H), 3.83 (b, 1H), 4.43 (m, 1H), 4.98 (q, 2H), 7.27 (t, 2H), 7.49 (t, 2H), 7.87 (d, 1H), 8.86 (s, 1H), 8.89 (d, 1H), 9.18 (s, 1H). LC-MS: 553 (M+1), 551, (M−1), 575 (M+23).

The following compounds were prepared by the procedure described in Example 4 above using appropriated starting materials.

N-(1-cyanocyclopropyl)-3-pyridin-3-ylmethanesulfonyl-2(R)-(2,2,2-trifluoro-1(S)-4-fluorophenylethylamino)propionamide. (compound 2), LC-MS: 485 (M+1), 507 (M+23), 483 (M−1).

N-(1-cyanocyclopropyl)-3-(pyridazin-3-ylmethanesulfonyl)-2-(R)-[2,2,2-trifluoro-1(S)-(4-fluorophenyl)ethylamino]propionamide. (compound 3), MS (486.2 M+1, 483.9 M−1).

N-(1-cyanocyclopropyl)-3-(2-trifluoromethylfuran-5-ylmethanesulfonyl)-2(R)-(2,2,2-trifluoro-1(S)-4-fluorophenylethylamino)-propionamide, Compound 4, $^1$H-NMR: (CDCl$_3$): 7.47 (1H, s, NH), 7.33-7.29 (2H, m), 7.24 (1H, s), 7.07-7.02 (2H, m), 6.79-6.77 (1H, m), 6.60-6.55 (1H, d), 4.59-4.4 (2H, ab,), 4.25-4.23 (1H, m), 3.64-3.55 (1H, m), 3.53-3.48 (1H, dd), 3.27-3.21 (1H, dd), 3-2.9 (1H, m), 1.5-1.4 (2H, m), 1.13-1.07 (2H, m).

LC-MS: 540.2 (M−1), 542.3 (M+1), 564.1 (M+Na).

N-(1-cyanocyclopropyl)-3-(2-methylthiazol-4-yl-methanesulfonyl)-2(R)-(2,2,2-trifluoro-1(S)-4-fluorophenylethylamino)propionamide, Compound 6, $^1$H-NMR: (CDCl$_3$): 7.41 (1H, s, NH), 7.31-7.27 (2H, m), 7.06-7.01 (2H, m), 4.6-4.3 (2H, dd), 4.3-4.23 (1H, m), 3.7-3.64 (1H, m), 3.63-3.55 (1H, dd), 3.38-3.3 (1H, aa), 3.2-3.1 (1H, m), 2.65 (3H, s), 1.55-1.45 (2H, m), 1.23-1.1 (2H, m). LC-MS: 503 (M−1), 504.8 (M+1), 526.9 (M+Na).

N-(1-cyanocyclopropyl)-3-pyridin-4-ylmethanesulfonyl-2(R)-(2,2,2-trifluoro-1(S)-4-fluorophenylethylamino)propionamide. (compound 7), LC-MS: 485 (M+1), 483 (M−1).

N-(1-cyanocyclopropyl)-3-(pyrimidin-4-ylmethanesulfonyl)-2-(R)-[2,2,2-trifluoro-1(S)-(4-fluorophenyl)ethylamino]propionamide. (compound 8), MS (486.2 M+1, 484.0 M−1).

N-(1-cyanocyclopropyl)-3-[2-(1-oxopyrrol-1-yl)ethanesulfonyl]-2(R)-(2,2,2-trifluoro-1(S)-4-fluorophenylethylamino)propionamide. (compound 9), LC-MS: 501.3 (M−1), 503.0 (M+1), 525.2 (M+Na).

N-(1-cyanocyclopropyl)-3-pyridin-3-ylmethanesulfonyl-2(R)-(2,2,2-trifluoro-1(R)-4-fluorophenylethylamino)propionamide. (compound 10), LC-MS: 485 (M+1), 507 (M+23), 483 (M−1).

N-(1-cyano-cyclopropyl)-3-cyclopropylmethanesulfonyl-2(R)-[2,2,2-trifluoro-1(S)-(3-fluorophenyl)ethylamino]propionamide (compound 11) was prepared by replacing 2,2,2,4'-tetrafluoroacetophenone with commercial 2,2,2,3'-tetrafluoroacetophenone and following the procedures of Reference B, Reference A, step 2, and Example 4 above, by replacing trifluoromethanesulfonic acid 2,2,2-trifluoro-1-(4-fluorophenyl)ethyl ester with trifluoromethanesulfonic acid 2,2,2-trifluoro-1-(3-fluorophenyl)-ethyl ester and 3-chloromethyl-4-trifluoromethylpyridine with cyclopropylmethylbromide. MW=447.45; MS (+1)=448.0; MS (−1)-446.2; MS (+Na)=470.0.

N-(1-cyanocyclopropyl)-3-(3,3,3-trifluoropropane-1-sulfonyl)-2(R)-(2,2,2-trifluoro-1(S)-4-fluorophenylethylamino)propionamide. (compound 12), LC-MS: 490 (M+1), 512 (M+23), 488 (M−1).

N-(1-cyanocyclopropyl)-3-(4-1H-[1.2.4]triazol-1-ylphenylmethanesulfonyl)-2-(R)-[(2,2,2-trifluoro-1(S)-(4-fluorophenyl)ethylamino]propionamide. (compound 14), MS (551.2 M+1, 549.4 M−1).

N-(1-cyanocyclopropyl)-3-[2-(2-oxo-2,3-dihydrobenzimidazol-1-yl)ethanesulfonyl]-2(R)-(2,2,2-trifluoro-1(S)-4-fluorophenyl-ethylamino)propionamide. (compound 15), LC-MS: 554 (M+1), 576 (M+23), 552 (M−1).

N-(1-cyanocyclopropyl)-3-(5-oxo-pyrrolidin-2-yl-methanesulfonyl)-2-(R)-(2,2,2-trifluoro-1(S)-4-fluorophenyl-ethylaminopropionamide. (compound 16), LC-MS: 491 (M+1), 513 (M+23), 489 (M−1).

N-(1-cyanocyclopropyl)-3-(2-fluoropyridin-3-ylmethanesulfonyl)-2(R)-(2,2,2-trifluoro-1(S)-4-fluorophenyl-ethylaminopropionamide. (compound 17), LC-MS: 503 (M+1), 525 (M+23), 501 (M−1).

N-(1-cyanocyclopropyl)-3-(quinolin-2-ylmethanesulfonyl)-2-(R)-[2,2,2-trifluoro-1(S)-(4-fluorophenyl)ethylamino]propionamide. (compound 25), MS (535.2 M+1, 533.2 M−1).

N-(1-cyanocyclopropyl)-3-(2,6-difluorophenylmethanesulfonyl)-2-(R)-[2,2,2-trifluoro-1(S)-(4-fluorophenyl)ethylamino]propionamide. (compound 31), MS (520.2 M+1, 518.1 M−1).

N-(1-cyanocyclopropyl)-3-(2,4-difluorophenylmethanesulfonyl)-2-(R)-[2,2,2-trifluoro-1(S)-(4-fluorophenyl)ethylamino]propionamide. (compound 32), MS (520.6 M+1, 518.2 M−1).

N-(1-cyanocyclopropyl)-3-(quinolin-3-ylmethanesulfonyl)-2-(R)-[2,2,2-trifluoro-1(S)-(4-fluorophenyl)ethylamino]propionamide. (compound 33), MS (535.1 M+1, 533.3 M−1).

N-(1-cyanocyclopropyl)-3-(4,4,4-trifluorobutane-1-sulfonyl)-2-(R)-[2,2,2-trifluoro-1(S)-(4-fluorophenyl)ethylamino]propionamide. (compound 34) MW=503.44; MS (+1)=504.1; MS (−1)=502.1; MS (+Na)=526.2. Prepared as described above but replacing 3-chloromethyl-4-trifluoromethylpyridine with commercial 4,4,4-trifluoro-1-bromobutane.

N-(1-cyanocyclopropyl)-3-(2-pyridin-2-ylethanesulfonyl)-2(R)-(2,2,2-trifluoro-1(S)-4-fluorophenyl-ethylamino)propionamide. (compound 39), LC-MS: 499 (M+1), 521 (M+23), 497 (M−1).

N-(1-cyanocyclopropyl)-3-(2-pyridin-3-ylethanesulfonyl)-2(R)-(2,2,2-trifluoro-1(S)-4-fluorophenyl-ethylamino)propionamide. (compound 41), LC-MS: 499 (M+1), 521 (M+23), 497 (M−1).

N-(1-cyanocyclopropyl)-3-(cyclopropylmethanesulfonyl)-2(R)-(2,2,2-trifluoro-1(RS)-2-chloropyridin-5-ylethylamino)propionamide. (compound 49), LC-MS: 463.2 (M−1), 465.2 (M+1), 487.2 (M+Na).

N-(1-cyanocyclopropyl)-3-(quinoxalin-2-ylmethanesulfonyl)-2-(R)-[2,2,2-trifluoro-1(S)-(4-fluorophenyl)ethylamino]propionamide. (compound 55), MS (536.2 M+1, 534.4 M−1).

N-(1-cyanocyclopropyl)-3-(ethanesulfonyl)-2(R)-(2,2,2-trifluoro-1(S)-4-fluorophenylethyl-amino)propionamide. (compound 62), LC/MS data: M+=421.9; M−420.1.

N-(1-cyanocyclopropyl)-3-(methanesulfonyl)-2(R)-(2,2,2-trifluoro-1(S)-4-fluorophenyl-ethylamino)propionamide. (compound 68), LC/MS data: M+=408.1; M−406.2.

N-(1-cyanocyclopropyl)-3-propane-1-sulfonyl)-2(R)-(2,2,2-trifluoro-1(S)-4-fluorophenylethyl-amino)propionamide (compound 69), LC/MS data M+435.8; M−=434.3.

N-(1-cyanocyclopropyl)-3-(1H-indol-2-ylmethanesulfonyl)-2(R)-(2,2,2-trifluoro-1(S)-4-fluorophenylethylamino)propionamide; (compound 70), LC-MS: 523 (M+1), 545 (M+23), 521 (M−1).

N-(1-cyanocyclopropyl)-3-(pyridin-2-ylmethanesulfonyl)-2(R)-(2,2,2-trifluoro-1(S)-3,4-difluorophenylethylamino)propionamide; (compound 73), LC-MS: 503 (M+1), 525 (M+23), 501 (M−1).

N-(1-cyanocyclopropyl)-3-(pyridin-3-ylmethanesulfonyl)-2(R)-(2,2,2-trifluoro-1(S)-3,4-difluorophenylethylamino)propionamide; (compound 74), LC-MS: 503 (M+1), 525 (M+23), 501 (M−1).

N-(1-cyanocyclopropyl)-3-[2-(1H-indol-3-yl)ethanesulfonyl]-2-(R)-[2,2,2-trifluoro-1(S)-(4-fluorophenyl)ethylamino]propionamide, (compound 75), MS (537.4 M+1, 535.2 M−1).

The heteroarylmethyl halide was either commercially available or prepared as follows:

Synthesis of 5-chloromethylpyrimidine

5-Methylpyrimidine (3.0 g, 31.9 mmol), N-chlorosuccinamide (5.23 g, 39.2 mmol), and benzoyl peroxide (0.077 g, 0.319 mmol) were combined in carbon tetrachloride (100 mL). The suspension was heated for 7 h at reflux. The reaction was cooled, filtered, concentrated and finally purified via flash chromatography with ethyl acetate/hexanes as eluent.

N-(1-cyanocyclopropyl)-3-(tetrahydro-pyran-4-yl-methanesulfonyl)-2(R)-[2,2,2-trifluoro-1(S)-(4-fluoro-phenyl)-ethylamino]-propionamide. (compound 76), MW=491.51 MS (+1)=492.3; MS (−1)=490.1; MS (+Na)=514.3.

Prepared as described above by replacing 3-chloromethyl-4-trifluoromethylpyridine with 4-iodomethyltetrahydropyran prepared as described below.

A solution of (tetrahydropyran-4-yl)methanol (0.5 g), triethylamine (1.2 mL) and dichloromethane (15 mL) was cooled to −40° C. and treated with methanesulfonylchloride (333 uL). The reaction mixture was allowed to stir at −40° C. to −20° C. for 2. It was then diluted with 25 mL dichloromethane, washed with water, dried over anhydrous magnesium sulfate, filtered and concentrated. Acetone (40 mL) and sodium iodide (1.3 g) were added and the reaction mixture was heated at reflux for 16 h. The reaction mixture was diluted with dichloromethane and filtered. The filtrate was concentrated to provide 4-iodomethyltetrahydro-pyran which was used without further purification.

N-(1-cyanocyclopropyl)-3-cyclopropylmethanesulfonyl-2(R)-[2,2,2-trifluoro-1-(3-hydroxy-6-methyl-pyridin-2-yl)-ethylamino]-propionamide. (compound 85)

MW=460.48; MS (+1)=461.1, MS (−1)=459.0, MS (+Na)=483.1 was prepared by replacing trifluoromethanesulfonic acid 2,2,2-trifluoro-1-(RS)-phenylethyl ester with trifluoro-methanesulfonic acid 2,2,2-trifluoro-1-(3-hydroxy-6-methyl-pyridin-2-yl)-ethyl ester prepared as described below.

6-Methyl-2-(2,2,2-trifluoro-1-hydroxy-ethyl)-pyridin-3-ol was prepared by a modification of a procedure detailed in *J. Heterocyclic Chem.*, 38, 25 (2001), p 25 by replacing traditional heating with microwave heating as follows.

Step 1

A mixture of commercially available 6-methylpyridin-3-ol (500 mg), trifluoroacetaldehyde methylhemiacetal (715 mg) and potassium carbonate (69 mg) was heated in a microwave reactor at 180° C. for 3 min. The reaction mixture was partitioned between ethyl acetate and water. The aqueous layer was extracted with ethyl acetate. The combined organics were dried over anhydrous sodium sulfate, filtered, and concentrated. The crude product was purified by silica gel chromatography using 1:1 hexane:ethyl acetate and recrystallized from ethyl acetate and hexane to give 627 mg of 6-methyl-2-(2,2,2-trifluoro-1-hydroxyethyl)pyridin-3-ol.

Step 2

6-Methyl-2-(2,2,2-trifluoro-1-hydroxyethyl)pyridin-3-ol was converted to trifluoromethanesulfonic acid 2,2,2-trifluoro-1-(3-hydroxy-6-methyl-pyridin-2-yl)-ethyl ester by the method described in step 2 of reference A.

N-(1-cyanocyclopropyl)-3-(2-tert-butyl-[1.3.4]-thiadiazol-5-ylmethanesulfonyl)-2(R)-(2,2,2-trifluoro-1(S)-4-fluorophenylethylamino)propionamide (compound 86), LC-MS: 546.1 (M−1), 548.1 (M+1), 569.8 (M+Na).

N-(1-cyanocyclopropyl)-3-(2,4,6-trifluorophenyl-methanesulfonyl)-2-(R)-[2,2,2-trifluoro-1(S)-(4-fluorophenyl)ethylamino]propionamide. (compound 87), MS (538.2 M+1, 536.1 M−1).

Example 5

Synthesis of N-(1-cyanocyclopropyl)-2(R)-[2,2,2-trifluoro-1(S)-(2,4-difluoro-phenyl)ethylamino]-3-(cyclopropylmethylsulfonyl)propionamide (compound 43)

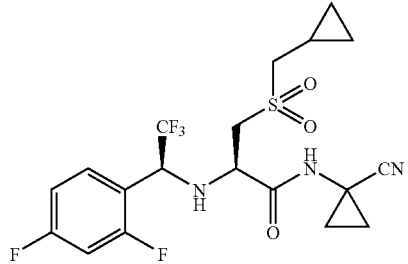

Step 1

2,4-Difluorobenzaldehyde (1.1 mL, 10.0 mmol) and (trifluoromethyl)trimethylsilane (1.77 mL, 12.0 mmol) were dissolved in THF (25 mL) and then cooled to 0° C. To this, 1M TBAF in THF (76 μL, 76 μmol) was added and the reaction mixture was allowed to warm to room temperature. After 3.25 h, 2.5M HCl (25 mL) was added. The reaction was stirred for 1 h and then extracted with ether. The organic layer was washed with brine and dried with Na$_2$SO$_4$. The solvent was removed under the reduced pressure to give 2,2,2-trifluoro-1-(2,4-difluoro-phenyl)ethanol (2.5 g) as a racemic mixture.

Step 2

2,2,2-Trifluoro-1-(2,4-difluorophenyl)ethanol (1.36 g, 6.4 mmol) was dissolved in dichloromethane (25 mL) and diisopropylethylamine (DIPEA, 5 mL, 28.8 mmol) was added. The resulting solution was cooled to −78° C. and trifluoromethanesulfonic anhydride (1.81 g, 6.4 mmol) was added. After 1 h, the reaction was warmed to −15° C. stirring was continued for 2 h. S-trityl-L-cysteine (2.33 g, 6.4 mmol) was then added and the reaction mixture was stirred overnight. After an aqueous work-up, the organic layer was dried with MgSO$_4$ then filtered through silica using a combination of ethyl acetate and acetic acid to give a diastereomeric mixture of 2(R)-[1-(2,4-difluorophenyl)-2,2,2-trifluoroethylamino]-3-tritylsulfanylpropionic acid (2.47 g).

Step 3

2(R)-[1-(2,4-Difluorophenyl)-2,2,2-trifluoroethylamino]-3-tritylsulfanylpropionic acid (2.47 g, 4.4 mmol) was dissolved in a 30% TFA/30% Et$_3$SiH/40% CH$_2$Cl$_2$ v/v/v solution (5 mL). After stirring for 1 h, toluene was added and all solvents were removed under reduced pressure. A basic aqueous work-up was done using 2.7 M NaOH. To the aqueous layer, P(CH$_2$CH$_2$COOH)$_3$ hydrochloride (126 mg, 0.44 mmol) and cyclopropylmethyl bromide (427 μL, 4.4 mmol) were added. After stirring overnight, an acidic aqueous work-up was done. The organic layer was washed with brine and dried with MgSO$_4$. The solvent was removed to get a diastereomeric mixture of 3-cyclopropylmethylsulfanyl-2(R)-[1-(2,4-difluorophenyl)-2,2,2-trifluoroethylamino]propionic acid (1.25 g).

Step 4

3-Cyclopropylmethylsulfanyl-2(R)-[1-(2,4-difluorophenyl)-2,2,2-trifluoroethylamino]-propionic acid (1.25 g, 3.4 mmol), HATU (1.29 g, 3.4 mmol), DIPEA (1.48 mL, 8.5 mmol) and 1-amino-cyclopropanecarbonitrile hydrochloride (403 mg, 3.4 mmol) was dissolved in NMP (20 mL). After stirring overnight, Oxone™ (3.14 g, 5.1 mmol) dissolved in water (7.9 mL) was added. After 1 h, more Oxone™ (3.14 g, 5.1 mmol) was added and the reaction mixture was stirred overnight. The product was precipitated from solution by the addition of water. The precipitate was purified by C18 RP-HPLC using an 0.1 mM HCl and acetonitrile system to give a diastereomeric mixture of N-(1-cyanocyclopropyl)-2(R)-[2,2,2-trifluoro-1(R)-(2,4-difluoro-phenyl)ethylamino]-3-(cyclopropylmethylsulfonyl)propionamide and N-(1-cyanocyclopropyl)-2(R)-[2,2,2-trifluoro-1(S)-(2,4-difluorophenyl)ethylamino]-3-(cyclopropylmethylsulfonyl)-propionamide (~250 mg).

Approximately 50 mg of the diastereomeric mixture was then purified on a Chiralcel OD-H (2 cm×25 cm) HPLC column using a mixture of IPA and hexanes and the diasteriomeric mixture was separated.

N-(1-cyanocyclopropyl)-3-(cyclopropylmethanesulfonyl)-2(R)-(2,2,2-trifluoro-1(S)-2,4-difluorophenylethylamino)propionamide. LC-MS: 466 (M+1), 464 (M−1), 488 (M+23). $^1$H-NMR (CDCl$_3$): 7.50 (s, 1H), 7.43 (q, 1H), 6.99 (m, 1H), 6.90 (m, 1H), 4.65 (q, 1H), 3.71 (dd, J=5.56, 4.95 Hz, 1H), 3.59 (dd, J=14.55, 6.05 Hz, 1H), 3.35 (dd, J=14.56, 4.50 Hz, 1H), 3.03 (d, 2H), 1.18 (m, 4H), 0.77 (m, 2H), 0.45 (m, 2H).

Following the procedure described in Example 5 above, the following compounds were prepared using the appropriated fluorinated benzaldehyde starting materials.

N-(1-cyanocyclopropyl)-3-(cyclopropylmethanesulfonyl)-2(R)-(2,2,2-trifluoro-1(S)-3,5-difluorophenylethylamino)propionamide, (compound 37). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(S)-2,5-difluorophenylethylamino)propionamide, (compound 38). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(S)-2,3-difluorophenylethylamino)propionamide, (compound 42). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(R)-2,5-difluorophenylethylamino)propionamide, (compound 63). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(S)-2,6-difluorophenylethylamino)propionamide, (compound 64). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(R)-2,6-difluorophenylethylamino)propionamide, (compound 65). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(R)-2,3-difluorophenylethylamino)propionamide, (compound 66). LC-MS: 466 (M+H), 488 (M+Na), 464 (M−H), 444 (M−HF).

N-(1-cyanocyclopropyl)-3-(cyclopropylmethanesulfonyl)-2(R)-(2,2,2-trifluoro-1(R)-2,4-difluorophenylethylamino)propionamide (compound 67). LC-MS: 466 (M+1), 464 (M−1), 488 (M+23). $^1$H-NMR (CDCl$_3$): 7.83 (s, 1H), 7.52 (q, 1H), 7.00 (m, 1H), 6.90 (m, 1H), 4.42 (m, 1H), 3.68 (m, 1H), 3.42 (m, 1H), 3.28 (m, 1H), 2.89 (d, 2H), 1.28 (m, 4H), 0.75 (m, 2H), 0.41 (m, 2H).

N-(1-cyanocyclopropyl)-3-(cyclopropylmethanesulfonyl)-2(R)-(2,2,2-trifluoro-1(S)-2-fluorophenylethylamino)propionamide, (compound 71). LC-MS: 448 (M+H), 470 (M+Na), 446 (M−H), 426 (M−HF).

N-(1-cyanocyclopropyl)-3-(cyclopropylmethanesulfonyl)-2(R)-(2,2,2-trifluoro-1(R)-2-fluorophenylethylamino)propionamide, (compound 72). LC-MS: 448 (M+H), 470 (M+Na), 446 (M−H), 426 (M−HF).

N-(1-cyanocyclopropyl)-3-(1-oxopyridin-2-ylmethanesulfonyl)-2(R)-(2,2,2-trifluoro-1(S)-2-fluorophenylethylamino)propionamide, (compound 77). LC-MS: 501 (M+H), 523 (M+Na), 499 (M−H), 479 (M−HF). This compound was isolated as by-product in the preparation of that gave the corresponding pyridine derivative.

N-(1-cyanocyclopropyl)-3-(1-oxopyridin-2-ylmethanesulfonyl)-2(R)-(2,2,2-trifluoro-1(R)-2-fluorophenylethylamino)propionamide, (compound 78). LC-MS: 501 (M+H), 523 (M+Na), 499 (M−H), 479 (M−HF). This compound was isolated as by-product in the preparation of that gave the corresponding pyridine derivative.

N-(1-cyanocyclopropyl)-3-(pyridin-2-ylmethanesulfonyl)-2(R)-(2,2,2-trifluoro-1(S)-2-fluorophenylethylamino)propionamide, (compound 79). LC-MS: 485 (M+H), 507 (M+Na), 483 (M−H), 463 (M−HF).

N-(1-cyanocyclopropyl)-3-(pyridin-2-ylmethanesulfonyl)-2(R)-(2,2,2-trifluoro-1(R)-2-fluorophenylethylamino)propionamide, (compound 80). LC-MS: 485 (M+H), 507 (M+Na), 483 (M−H), 463 (M−HF).

N-(1-cyanocyclopropyl)-3-(cyclopropylmethanesulfonyl)-2(R)-(2,2,2-trifluoro-1(S)-2,3,4-trifluorophenylethylamino)propionamide, (compound 81). LC-MS: 484 (M+H), 506 (M+Na), 482 (M−H), 462 (M−HF).

N-(1-cyanocyclopropyl)-3-(cyclopropylmethanesulfonyl)-2(R)-(2,2,2-trifluoro-1(R)-2,3,4-trifluorophenylethylamino)propionamide, (compound 82). LC-MS: 484 (M+H), 506 (M+Na), 482 (M−H), 462 (M−HF).

Example 6

Synthesis of N-(1-cyanocyclopropyl)-1-3-(cyclopropylmethanesulfonyl)2(R)-[2,2,3,3,3-pentafluoro-1 (S)-(4-fluorophenyl)propylamino]propionamide (compound 54)

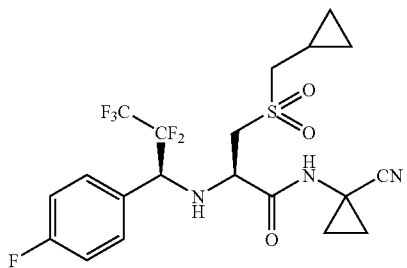

Step 1

To a solution of 1-bromo-4-fluorobenzene (16.5 mL, 0.15 mol) in anhydrous THF (200 mL) at −78° C., 2,2,3,3,3-pentafluoropropionic acid ethyl ether (14.4 g, 75 mmol) was slowly added. After stirring for 4 h at −78° C., ethyl ether (200 mL) and sat. sol. of NH$_4$Cl (100 mL) were added. The resulting mixture was placed in a sep. funnel, shaken and the organic phase separated. After washing with brine, the solution was dried over magnesium sulfate. The solution was concentrated in a rotary vapor and the residue was purified by distillation to give 2,2,3,3,3-pentafluoro-1-(4-fluorophenyl)propan-1-one.

Step 2

To a solution of 2,2,3,3,3-pentafluoro-1-(4-fluorophenyl)propan-1-one (13.0 g, 53 mmol) in a mixture 1:1 of dichloromethane and toluene (160 mL) at room temperature, 1M solution of S-methyl-CBS-oxazaborolidine in toluene (5.3 mL, 5.3 mmol) was added at room temperature. The reaction mixture was cooled at −78° C. and catecholborane (7.62 g, 63 mmol) was added. After stirring for 7 h at −78° C., a 4 M solution of HCl in dioxane (18 mL) was added. After allowing the reaction mixture to warm to room temperature, water (5 mL) was added, stirred for 5 min and 10% solution of sodium metabisulfite (25 mL) was added. The heterogeneous mixture was stirred for 15 min and the solid was separated by filtration. The solution was concentrated on rotovap to reduce the amount of dichloromethane and then the residue was diluted with hexanes (100 mL). The resulting solution was washed with a 10% solution of sodium metabisulfite (100 mL) and brine (100 mL). After drying over magnesium sulfate, the solution was concentrated and the crude was purified on a silica gel column, using dichloromethane as eluent to give (R)-2,2,3,3,3-pentafluoro-1-(4-fluorophenyl)propan-1-ol as an oil (12.01 g).

Step 3

A 60% suspension of NaH in oil (2.35 g, 58.8 mmol) was washed several times with hexanes and after suspending it in anhydrous ethyl ether (100 mL), (R)-2,2,3,3,3-pentafluoro-1-(4-fluoro-phenyl)propan-1-ol (12.0 g, 49 mmol) in ether (20 mL) was added slowly at room temperature. After stirring for 15 min, the reaction mixture was cooled at 0° C. and trifluoromethylsulfonyl chloride (12.38 g, 73.7 mmol) was added. The reaction mixture was stirred for 1:30 h at 0° C., then concentrated under reduced pressure and the residue was diluted with hexane (100 mL). The reaction mixture was washed with sat. sol. NaHCO$_3$, brine and dried over magnesium sulfate. After removing the solvent on rotovapor, trifluoro-methanesulfonic acid (R)-2,2,3,3,3-pentafluoro-1-(4-fluorophenyl)propyl ester was obtained as a colorless oil (16.0 g).

Step 4

To a suspension of L-trityl-cysteine (15.45 g, 42 mmol) and diisopropyl ethyl amine (29.3 mL, 168 mmol) in dichloromethane (350 mL), a solution of trifluoromethanesulfonic acid (R)-2,2,3,3,3-pentafluoro-1-(4-fluorophenyl)-propyl ester (16.0 g, 42 mmol) in dichloromethane (20 mL) was added at room temperature. The reaction mixture was stirred for 20 h and then concentrated. The residue was dissolved in ethyl acetate (300 mL). The organic phase was washed with cold 1N HCl (100 mL), brine and dried over magnesium sulfate. After solvent evaporation, the crude was purified by flash chromatography, using a mixture 1:2 of EA/hexanes to give 2(R)-[2,2,3,3,3-pentafluoro-1-(S)-(4-fluorophenyl)propylamino]-3-tritylsulfanyl-propionic acid as an oil (6.93 g).

Step 5

To a solution of 2(R)-[2,2,3,3,3-pentafluoro-1-(S)-(4-fluorophenyl)propylamino]-3-tritylsulfanylpropionic acid (6.92 g, 12 mmol) in dichloromethane (10 mL), triethylsilane (3.73 mL, 23.4 mmol) and TFA (3.61 mL, 46.9 mmol) were added at room temperature. The reaction mixture was stirred for 4 h. The solvent and volatiles were evaporated on rotovap, benzene was added to the residue and the mixture was evaporated again to ensure complete removal of excess TFA. The residue was dissolved in 1 N NaOH (50 mL) and extracted with hexanes. To the resulting solution, P(CH$_2$CH$_2$CO$_2$H)$_3$.HCl (0.343 g, 1.2 mmol) was added, and a 0.2 M stock solution of 2(R)-[2,2,3,3,3-pentafluoro-1-(S)-(4-fluorophenyl)propylamino]-3-mercaptopropionic acid was obtained.

Step 6

To a 0.2 M stock solution of 2(R)-[2,2,3,3,3-pentafluoro-1-(S)-(4-fluorophenyl)propyl-amino]-3-3-mercaptopropionic acid in NaOH (10 mL, 2 mmol), cyclopropylmethylbromide (0.270 g, 2 mmol) was added. After stirring the reaction mixture for 5 h at room temperature, 1 M HCl solution was added until pH 2-3. The reaction mixture was extracted with ethyl acetate and the combined organic extracts were washed with brine and dried over sodium sulfate and concentrated to give 3-cyclopropylmethanesulfanyl-2(R)-[2,2,3,3,3-pentafluoro-1-(s)-(4-fluoro-phenyl)propylamino]-propionic acid as a foam (0.678 g).

Step 7

To a solution of 3-cyclopropylmethanesulfanyl-2(R)-[2,2,3,3,3-pentafluoro-1-(S)-(4-fluoro-phenyl)propylamino]-propionic acid (0.670 g, 1.67 mmol) in DMF (3 mL), 1-amino-cyclopropanecarbonitrile hydrogen chloride salt (0.236 g, 3 mmol), HATU (0.760 g, 2 mmol) and diisopropyl ethyl amine (0.87 mL, 5 mmol) were added. After stirring for 4 h, the reaction mixture was diluted with ethyl acetate (20 mL) and then washed with a sat. solution of NaHCO$_3$ (10 mL), water (10 mL) and brine (10 mL). The crude solution was dried over sodium sulfate. After evaporation of the solvent, the crude oil was purified by flash chromatography, using a mixture 1:1 of EA/Hexanes to give N-(1-cyanocyclopropyl)-3-(cyclopropylmethanesulfanyl)-2(R)-(3,3,3,2,2-pentafluoro-1(S)-4-fluorophenylpropylamino)propionamide as a light yellow solid (0.558 g).

Step 8

To a solution of N-(1-cyanocyclopropyl)-3-(cyclopropylmethanesulfanyl)-2(R)-(3,3,3,2,2-pentafluoro-1(S)-4-fluorophenylpropylamino)propionamide (0.540 g, 1.16 mmol) in N-methylpyrrolidinone (4 mL), a solution of OXONE (1.06 g, 1.74 mmol) in water (3.8 mL) was added at room temperature. The heterogeneous mixture was stirred overnight at room temperature. After cooling at 0° C., water (20 mL) was added and mixture was stirred for 15 min. The solid was separated by filtration and washed with fresh water. The crude solid was purified by flash chromatography using a mixture of EA/H as eluent to give title compound as a white solid (0.1 05 g, 19%). $^1$H NMR (DMSO-$d_6$): δ 8.94 (1H, s), 7.44 (2H, dd), 7.22 (2H, t), 4.53 (1H, m), 3.68 (1H, q), 3.66 (1H, m), 3.30 (2H, m), 3.12 (2H, m), 1.30 (2H, m), 1.00 (1H, m), 0.90 (1H, m), 0.58 (2H, m), 0.47 (1H, m), 0.30 (2H, m). LC/MS, M+1: 498.4, M−1: 496.3.

Example 7

Synthesis of N-(1-cyanocyclopropyl)-3-(pyridin-2-ylmethanesulfonyl)-2(R)-[2,2,3,3,3-pentafluoro-1 (S)-(4-fluorophenyl)propylamino]propionamide (compound 50)

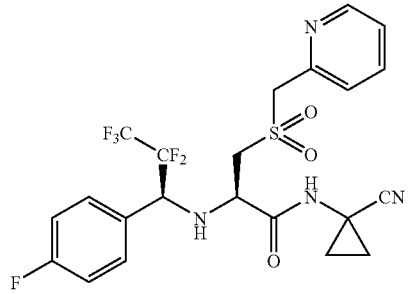

Step 1

To a 0.2 M stock solution of 3-mercapto-2(R)-[2,2,3,3,3-pentafluoro-1-(S)-(4-fluorophenyl)propylamino]-propionic acid in NaOH (10 mL, 2 mmol), 2-chloromethylpyridine (0.328 g, 2 mmol) and 1 N solution of NaOH (1 mL) were added. After stirring the reaction mixture for 5 h at room temperature, 1 M HCl solution was added until pH 5-6. The mixture was extracted with ethyl acetate and the combined organic extracts were washed with brine and dried over sodium sulfate and concentrated to give N-(1-cyanocyclopropyl)-3-pyridin-2-ylmethanesulfanyl)-2(R)-[3,3,3,2,2-pentafluoro-1(S)-(4-fluorophenyl)propylamino]-propionamide as a foam (0.692 g) which was converted to the title compound as described in Example 6 above.

$^1$H NMR (DMSO-$d_6$): δ 8.97 (1H, s), 8.60 (1H, m), 7.88 (1H, m), 7.47 (4H, m), 7.24 (2H, t), 4.74 (2H, s), 4.58 (1H, m), 3.73 (2H, m), 3.44 (2H, m), 1.33 (2H, m), 0.93 (1H, m), 0.53 (1H, m). LC/MS, M+1: 535.3; M−1: 533.4 and compound 51 (15%) as a by-product. LC/MS, M+1: 551.3, M−1: 549.4.

Proceeding as described in Example 7 above but substituting 2-chloromethylpyridine with 3-chloromethylpyridine provided N-(1-cyanocyclopropyl)-3-(pyridin-3-ylmethanesulfonyl)-2(R)-(3,3,3,2,2-pentafluoro-1(S)-4-fluorophenyl-propylamino)-propionamide (compound 52), $^1$H NMR (DMSO-$d_6$): δ 9.00 (1H, s), 8.61 (1H, m), 8.57 (1H, m), 7.80 (1H, m), 7.48 (3H, m), 7.24 (2H, t), 4.64 (2H, dd), 4.58 (1H, m), 3.82 (1H, t), 3.70 (1H, m), 3.42 (1H, m), 3.30 (1H, m), 1.20 (2H, m), 0.90 (1H, m), 0.50 (1H, m). LC/MS, M+1: 535.3, M−1: 533.2. Compound 53 was obtained as a by-product (5%). LC/MS, M+1: 551.3, M−1: 549.3; and N-(1-cyanocyclopropyl)-3-(1-oxopyridin-3-yl-methanesulfonyl)-2(R)-(3,3,3,2,2-pentafluoro-1(S)-4-fluorophenylpropylamino)-propionamide (compound 53)

Proceeding as described in Example 7 above but substituting 2-chloromethyl-pyridine with 5-methylisoxazol-3-ylm-ethyl chloride provide N-(1-cyanocyclopropyl)-3-(5-methylisoxazol-3-ylmethanesulfonyl)-2(R)-(3,3,3,2,2-pentafluoro-1(S)-4-fluorophenylpropylamino)-propionamide (compound 59), $^1$HNMR (DMSO-$d_6$): 8.97 (1H, s), 7.46 (2H, dd), 7.24 (2H, dd), 6.32 (1H, s), 4.74 (2H, d), 4.55 (1H, m), 3.70 (2H, m), 3.44 (2H, m), 2.45 (3H, s), 1.33 (2H, m), 0.92 (1H, m), 0.52 (1H, m). LC\MS: M−1: 536.9, M+1: 539.2

Proceeding as described in Example 7 N-(1-cyanocyclopropyl)-3-(2-pyridin-2-ylethanesulfonyl)-2(R)-(2,2,3,3,3-pentafluoro-1(S)-4-fluorophenylethylamino)propionamide was prepared (compound 88), $^1$HNMR (DMSO-$d_6$): 8.97 (1H, s), 8.75 (1H, d), 8.28 (1H, m), 7.82 (1H, d), 7.72 (1H, m), 7.46 (2H, dd), 7.24 (2H, dd), 4.74 (1H, m), 4.00-3.30 (7H, bm), 1.33 (2H, m), 0.92 (1H, m), 0.52 (1H, m). LC\MS: M−1: 547.5, M+1: 549.3

Example 8

Synthesis of N-(1-cyanocyclopropyl)-3-(2-trifluoromethylphenylmethanesulfonyl)-2(R)-(2,2,2-trifluoro-1(S)-4-fluorophenylethylamino)-propionamide (compound 35)

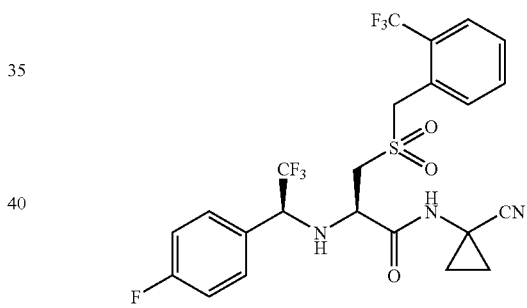

2-(Trifluoromethyl)benzyl bromide (0.50 mmol) was dissolved in dioxane (3 mL) and a 0.16 M stock solution of 3-mercapto-2(R)-[2,2,2-trifluoro-1(S)-(4-fluorophenyl) ethylamino]-propionic acid (4.7 mL, 0.75 mmol) in 1.0 M aqueous sodium hydroxide/0.032 M tris(2-carboxyethyl) phosphine hydrochloride was added. After stirring overnight, the reaction mixture was concentrated to half the volume and then diluted with water and washed with heptane. Ethyl acetate (5 mL) was added and the two phase mixture was placed in an ice/water bath and the pH was adjusted to 3 with 3.0 M hydrochloric acid. The aqueous phase was extracted with EtOAc and the combined organic extracts were washed with brine, dried over MgSO$_4$, and concentrated. The residue was dissolved in DMF (2 mL) and 1-aminocyclopropanecarbonitrile hydrochloride (64 mg, 0.54 mmol), DIPEA (260 µL, 1.5 mmol), HATU (191 mg, 0.50 mmol) were added and the reaction mixture was stirred overnight. After concentrating the residue was dissolved in EtOAc and washed with 1.0 M KHSO$_4$, saturated NaHCO$_3$, and brine and dried over anhydrous MgSO$_4$. Solvent was removed and the residue was dissolved in acetonitrile (3 mL) and a 0.50 M aqueous solution of Oxone™ (1.5 mL, 0.75 mmol) was added. After stirring overnight, the reaction mixture was diluted with water and extracted with EtOAc. The combined organic extracts were washed with brine, dried over anhydrous MgSO$_4$ and concentrated. The residue was purified by flash chromatography on silica gel to give the title compound (55 mg) as a white solid mixture of diastereomers in 80% de (1S,2R)>(1R,2R). (compound 35), LC-MS: 552 (M+1), 551 (M−1), 574 (M+23), $^1$H-NMR (DMSO): 0.80 (m, 1H), 1.05 (m, 1H), 1.38 (m, 2H), 3.38 (m, 1H), 3.68 (m, 2H), 3.80 (m, 1H), 4.40 (m, 1H), 4.88 (q, 2H), 7.25 (t, 2H), 7.47 (dd, 2H), 7.65 (m, 2H), 7.75 (m, 1H), 7.82 (d, 1H), 9.10 (s, 1H).

Following the procedure described above the following compounds were prepared.

N-(1-cyanocyclopropyl)-3-(2-methylpropylsulfonyl)-2(R)-(2,2,2-trifluoro-1(S)-4-fluorophenylethylamino)propionamide (compound 29), LC-MS: 450 (M+1), 448 (M−1), 472 (M+23).

N-(1-cyanocyclopropyl)-3-(2-trifluoromethoxyphenylmethanesulfonyl)-2(R)-(2,2,2-trifluoro-1(S)-4-fluorophenylethylamino)-propionamide (compound 36), LC-MS: 568 (M+1), 566 (M−1), 590 (M+23).

N-(1-cyanocyclopropyl)-3-(tetrahydropyran-2RS-ylmethanesulfonyl)-2(R)-(2,2,2-trifluoro-1(S)-4-fluorophenylethylamino)-propionamide (compound 56),

LC-MS: 492 (M+1), 490 (M−1), 514 (M+23).

N-(1-cyanocyclopropyl)-3-(2,6-dichlorophenylmethanesulfonyl)-2(R)-(2,2,2-trifluoro-1(S)-4-fluorophenylethylamino)propionamide (compound 57), LC-MS: 552:554:556 ratio 9:6:1 (M+1); 550, 552, 554 ratio 9:6:1 (M−1); 574, 576, 578 ratio 9:6:1 (M+23).

N-(1-cyanocyclopropyl)-3-(1-ethyl-2,5-dioxopyrrolidin-3-ylmethanesulfonyl)-2(R)-(2,2,2-trifluoro-1(S)-4-fluorophenyl-ethylamino)propionamide (compound 89)

LC-MS: 553 (M+1), 551 (M−1), 575 (M+23).

Example 9

Synthesis of N-(1-cyanocyclopropyl)-3-(5-methylisoxazol-3-ylmethanesulfonyl)-2(R)-(2,2,2-trifluoro-1(S)-4-fluorophenyl-ethylamino)propionamide (compound 28)

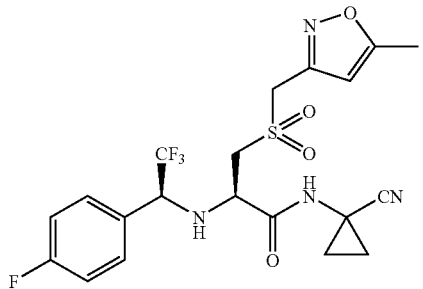

3-(Bromomethyl)-5-methylisoxazole (0.5 mmol) was dissolved in acetonitrile (1.5 mL) and a 0.50 M stock solution of 3-mercapto-2(R)-[2,2,2-trifluoro-1(S)-(4-fluorophenyl) ethyl-amino]propionic acid (1.5 mL, 0.75 mmol) in 2.0 M aqueous sodium hydroxide was added. After 2 h, water (2 mL) and acetonitrile (2 mL) were added and the two phase mixture was washed with heptane. The heptane extract was discarded and the aqueous phase was placed in an ice/water bath and the pH was adjusted to 3 with 1.0 M aqueous KHSO$_4$. The organic phase was separated and the aqueous phase was extracted with EtOAc. The combined organic extracts were washed with brine, dried over anhydrous MgSO$_4$, and concentrated. The residue was dissolved in acetonitrile (3 mL) and 1-aminocyclopropanecarbonitrile hydrochloride (88 mg, 0.74 mmol), DIPEA (390 μL, 2.2 mmol) and HATU (287 mg, 0.75 mmol) were added. After 2 h, the reaction mixture was diluted with and a 0.50 M aqueous solution of Oxone™ (3.0 mL, 1.5 mmol) was added. After stirring the reaction mixture at 50° for 2 h, water (5 mL) was added and the reaction mixture was concentrated to remove acetonitrile. The aqueous layer was extracted with EtOAc, and the combined organic extracts were washed with 1.0 M aqueous KHSO$_4$, 1:1 water:saturated NaHCO$_3$, and brine, and dried over anhydrous MgSO$_4$. After concentration, the residue through a plug of silica gel using EtOAc eluent and collected all material with R$_f$>0.5. After concentration the residue was purified by flash chromatography to give title compound (63 mg) as a white solid mixture of diastereomers, 85% de, (1'S,2R)>(1'R,2R). LC-MS: 489 (M+1), 487 (M−1), 511 (M+23). $^1$H-NMR (DMSO): 0.74 (m, 1H), 1.01 (m, 1H), 1.36 (m, 2H), 2.44 (s, 3H), 3.36 (m, 1H), 3.68 (m, 2H), 3.75 (m, 1H), 4.41 (m, 1H), 4.77 (q, 2H), 6.33 (s, 1H), 7.25 (t, 2H), 7.47 (dd, 2H), 9.04 (s, 1H).

Following the procedure described above, the following compounds were prepared:

N-(1-cyanocyclopropyl)-3-(benzo[1.2.5]thiadiazol-4-ylmethanesulfonyl)-2(R)-(2,2,2-trifluoro-1(S)-4-fluorophenyl-ethylamino)propionamide (compound 26), LC-MS: 542 (M+1), 540 (M−1), 564 (M+23).

N-(1-cyanocyclopropyl)-3-(benzothiazol-2-ylmethanesulfonyl)-2(R)-(2,2,2-trifluoro-1(S)-4-fluorophenylethylamino)propionamide (compound 27), LC-MS: 541 (M+1), 539 (M−1), 563 (M+23).

N-(1-cyanocyclopropyl)-3-(cyclobutylmethanesulfonyl)-2(R)-(2,2,2-trifluoro-1(S)-4-fluorophenylethylamino)propionamide (compound 30), LC-MS: 462 (M+1), 460 (M−1), 484 (M+23).

N-(1-cyanocyclopropyl)-3-(quinolin-8-ylmethanesulfonyl)-2(R)-(2,2,2-trifluoro-1(S)-4-fluorophenyl-ethylamino) propionamide (compound 41), LC-MS: 535 (M+1), 533 (M−1), 557 (M+23).

N-(1-cyanocyclopropyl)-3-(5-methyl-3-phenylisoxazol-4-ylmethanesulfonyl)-2(R)-(2,2,2-trifluoro-1(S)-4-fluorophenylethylamino)-propionamide (compound 44),

LC-MS: 565 (M+1), 563 (M−1), 587 (M+23).

N-(1-cyanocyclopropyl)-3-(4-methyl-2-phenyl-[1.2.3] triazol-5-ylmethanesulfonyl)-2(R)-(2,2,2-trifluoro-1(S)-4-fluorophenyl-ethylamino)-propionamide (compound 45), LC-MS: 565 (M+1), 563 (M−1), 487 (M+23).

N-(1-cyanocyclopropyl)-3-(2-cyanophenylmethanesulfonyl)-2(R)-(2,2,2-trifluoro-1(S)-4-fluorophenyl-ethylamino) propionamide (compound 46), LC-MS: 509 (M+1), 507 (M−1), 531 (M+23).

N-(1-cyanocyclopropyl)-3-(3-methoxycarbonylphenylmethanesulfonyl)-2(R)-(2,2,2-trifluoro-1(S)-4-fluorophenylethylamino)-propionamide (compound 47),

LC-MS: 542 (M+1), 540 (M−1), 4564 (M+23).

N-(1-cyanocyclopropyl)-3-(3-methoxycarbonylfuran-2RS-ylmethanesulfonyl)-2(R)-(2,2,2-trifluoro-1(S)-4-fluorophenylethylamino)-propionamide (compound 58),

LC-MS: 532 (M+1), 530 (M−1), 554 (M+23).

Example 10

Synthesis of N-(1-cyanocyclopropyl)-2(S)-[2,2,2-trifluoro-1(RS)-(4-fluorophenyl)ethylamino]-4-pyridin-2-ylsulfonyl)butyramide

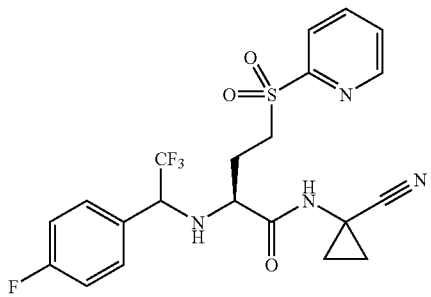

Step 1

3(S)-Aminodihydrofuran-2-one (12.4 g, 68.2 mmol) was added in dioxane (136 mL) and 1N NaOH (136 mL) was added to give a clear solution. The reaction mixture was cooled in ice-water bath and Boc-anhydride (16.35 g, 74.9 mmol) was added in portions. The reaction mixture was warmed to ambient temp. overnight and after concentrating it to approx. 150 mL, ethyl acetate (150 mL) was added. After acidifying the reaction mixture to pH 4 with concentrated aqueous $KHSO_4$, the organic layer was separated and concentrated to give (2-oxotetrahydro-furan-3(R)-yl)-carbamic acid tert-butyl ester as a white solid which was used without further purification.

Step 2

Clean sodium metal (0.205 g, 8.95 mmol) was added, in portions, to anhydrous methanol (20 mL) in a thick walled tube. The suspension was stirred under anhydrous nitrogen until all the metal had dissolved, then pyridine-2-thiol (1.0 g, 8.95 mmol) was added. After stirring for 20 min, (2-oxotetrahydro-furan-3(R)-yl)-carbamic acid tert-butyl ester (1.8 g, 8.95 mmol) was added as a solid and the tube was capped and heated to 100° C. for 16 h. The reaction mixture was concentrated, then purified via flash chromatography (MeOH, $CH_2Cl_2$ as eluent) to give 2(S)-tert-butoxycarbonylamino-4-(pyridin-2-ylsulfanyl)butyric acid (0.75 g) as a clear oil.

Step 3

To 2(S)-tert-butoxycarbonylamino-4-(pyridin-2-ylsulfanyl)butyric acid (0.75 g, 2.40 mmol) in methanol (16 mL) and toluene (50 mL) was added a 2.0M solution of (trimethylsilyl)diazomethane (3.12 mmol) dropwise. After 3 h, the reaction mixture was concentrated to give methyl 2(S)-tert-butoxycarbonylamino-4-(pyridin-2-ylsulfanyl)butyrate as an oily residue which was used without further purification.

Step 4

To methyl 2(S)-tert-butoxycarbonylamino-4-(pyridin-2-ylsulfanyl)butyrate (0.75 g, 2.4 mmol) in THF (5 mL) was added methanesulfonic acid (6.9 g, 7.2 mmol) in one portion. The solution was stirred for 16 h and the crude reaction mixture was concentrated to give methyl 2(S)-amino-4-(pyridin-2-ylsulfanyl)butyrate as the mesylate salt which was used directly in the next step.

Step 5

Methyl 2(S)-amino-4-(pyridin-2-ylsulfanyl)butyrate (0.610 g, 2.33 mmol), 2,2,2,4'-tetrafluoroacetophenone (0.393 g, 2.05 mmol), and DIPEA (1.24 g, 9.63 mmol) were combined in $CH_2Cl_2$ (10 mL). $TiCl_4$ (1.90 mmol in $CH_2Cl_2$) was added dropwise over a 5 min period. The resulting dark solution was stirred for 3 h at which time sodium cyanoborohydride (6.35 mmol) in methanol (5 mL) was added in one portion, and the brown solution stirred for an additional 45 min. The reaction mixture was diluted with ethyl acetate, poured onto a bed of $MgSO_4$ and filtered. Concentration and purification by flash chromatography (50% ethyl acetate/hexanes) afforded 4-(pyridin-2-ylsulfanyl)-2(S)-[2,2,2-trifluoro-1-(4-fluorophenyl)ethylamino]-butyric acid methyl ester as a mixture of diastereomers.

Step 6

4-(Pyridin-2-ylsulfanyl)-2(S)-[2,2,2-trifluoro-1-(4-fluorophenyl)ethylamino]butyric acid methyl ester was dissolved in methanol (2 mL) and 1N NaOH (1.2 mL) was added. After stirring for 2 h, methanol was removed and the aqueous layer was acidified to pH 5. After extracting with ethyl acetate the organic layer was dried and concentrated to give 4-(pyridin-2-ylsulfanyl)-2(S)-[2,2,2-trifluoro-1-(4-fluorophenyl)ethylamino]butyric acid as an oil which was then converted to the title compound as described above. MS (485.5 M+1)

BIOLOGICAL EXAMPLES

Example 1

Cathepsin B Assay

Solutions of test compounds in varying concentrations were prepared in 10 µL of dimethyl sulfoxide (DMSO) and then diluted into assay buffer (40 µL, comprising: N,N-bis(2-hydroxyethyl)-2-aminoethanesulfonic acid (BES), 50 mM (pH 6); polyoxyethylenesorbitan monolaurate, 0.05%; and dithiothreitol (DTT), 2.5 mM). Human cathepsin B (0.025 pMoles in 25 µL of assay buffer) was added to the dilutions. The assay solutions were mixed for 5-10 seconds on a shaker plate, covered and incubated for 30 min at room temperature. Z-FR-AMC (20 nMoles in 25 µL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin B inhibitory activity.

Example 2

Cathepsin K Assay

Solutions of test compounds in varying concentrations were prepared in 10 µL of dimethyl sulfoxide (DMSO) and then diluted into assay buffer (40 µL, comprising: MES, 50 mM (pH 5.5); EDTA, 2.5 mM; and DTT, 2.5 mM). Human cathepsin K (0.0906 pMoles in 25 µL of assay buffer) was added to the dilutions. The assay solutions were mixed for 5-10 seconds on a shaker plate, covered and incubated for 30 min at room temperature. Z-Phe-Arg-AMC (4 nMoles in 25 µL of assay buffer) was added to the assay solutions and hydrolysis was followed spectrophotometrically at (λ 460 nm) for 5 min. Apparent inhibition constants ($K_i$) were calculated from the enzyme progress curves using standard mathematical models.

Compounds of the invention were tested by the above-described assay and observed to exhibit cathepsin K inhibitory activity.

Example 3

Cathepsin L Assay

Solutions of test compounds in varying concentrations were prepared in 10 mL of dimethyl sulfoxide (DMSO) and then diluted into assay buffer (40 µL, comprising: MES, 50 mM (pH 5.5); EDTA, 2.5 mM; and DTT, 2.5 mM). Human cathepsin L (0.05 pMoles in 25 µL of assay buffer) was added to the dilutions. The assay solutions were mixed for 5-10 seconds on a shaker plate, covered and incubated for 30 min at room temperature. Z-Phe-Arg-AMC (1 nMoles in 25 µL of assay buffer) was added to the assay solutions and hydrolysis was followed spectrophotometrically at ($\lambda$ 460 nm) for 5 min. Apparent inhibition constants ($K_i$) were calculated from the enzyme progress curves using standard mathematical models.

Compounds of the invention were tested by the above-described assay and observed to exhibit cathepsin L inhibitory activity.

Example 4

Cathepsin S Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM); β-mercaptoethanol, 2.5 mM; and BSA, 0.00%. Human cathepsin S (0.05 pMoles in 25 µL of assay buffer) was added to the dilutions. The assay solutions were mixed for 5-10 seconds on a shaker plate, covered and incubated for 30 min at room temperature. Z-Val-Val-Arg-AMC (4 nMoles in 25 µL of assay buffer containing 10% DMSO) was added to the assay solutions and hydrolysis was followed spectrophotometrically (at $\lambda$ 460 nm) for 5 min. Apparent inhibition constants ($K_i$) were calculated from the enzyme progress curves using standard mathematical models.

Compounds of the invention were tested by the above-described assay and observed to exhibit cathepsin S inhibitory activity of < or =100 nm.

Example 5

Cathepsin F Assay

Solutions of test compounds in varying concentrations were prepared in 10 µL of dimethyl sulfoxide (DMSO) and then diluted into assay buffer (40 µL, comprising: MES, 50 mM (pH 6.5); EDTA, 2.5 mM; and NaCl, 100 mM); DTT, 2.5 mM; and BSA, 0.01%. Human cathepsin F (0.1 pMoles in 25 µL of assay buffer) was added to the dilutions. The assay solutions were mixed for 5-10 seconds on a shaker plate, covered and incubated for 30 min at room temperature. Z-Phe-Arg-AMC (2 nmoles in 25 µL of assay buffer containing 10% DMSO) was added to the assay solutions and hydrolysis was followed spectrophotometrically (at $\lambda$ 460 nm) for 5 min. Apparent inhibition constants ($K_i$) were calculated from the enzyme progress curves using standard mathematical models.

Compounds of the invention were tested by the above-described assay and observed to exhibit cathepsin F inhibitory activity.

FORMULATION EXAMPLES

Example 1

Representative Pharmaceutical Formulations Containing a Compound of Formula (I)

| ORAL FORMULATION | |
|---|---|
| Compound of Formula (I) | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of Formula (I) | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of Formula (I) | 1% |
| Microcrystalline Cellulose | 73% |
| Stearic Acid | 25% |
| Colloidal Silica | 1% |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

I claim:

1. A compound of Formula (I):

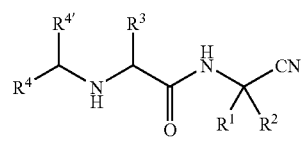

(I)

$R^1$ is hydrogen, alkyl, or haloalkyl;
$R^2$ is hydrogen, alkyl, or haloalkyl; or
$R^1$ and $R^2$ taken together with the carbon atom to which $R^1$ and $R^2$ are attached form cycloalkylene optionally substituted with one to four fluoro, piperidin-4-yl wherein the nitrogen atom of the piperidinyl ring is substituted with alkyl, haloalkyl, or cycloalkyl, tetrahydropyran-4-yl, tetrahydrothiopyran-4-yl, 1,1-dioxohexahydrothiopyran-4-yl, or —CH$_2$—O—CH$_2$—;

$R^3$ is -alkylene-SO$_2$-alkyl, -alkylene-SO$_2$-haloalkyl, -alkylene-SO$_2$-cycloalkyl, -alkylene-SO$_2$-cycloalkylalkyl, -alkylene-SO$_2$-aryl, -alkylene-SO$_2$-aralkyl, -alkylene-SO$_2$-heterocycloalkyl, -alkylene-SO$_2$-heterocycloalkylalkyl, -alkylene-SO$_2$-heteroaryl, -alkylene-SO$_2$-heteroaralkyl, -alkylene-SO$_2$-haloalkylene-aryl or -alkylene-SO$_2$-haloalkylene-heteroaryl wherein the aromatic or alicyclic ring in $R^3$ is optionally substituted with one, two, or three $R^a$ independently selected from alkyl, alkylsulfonyl, haloalkyl, alkoxy, hydroxy, hydroxyalkyl, haloalkoxy, halo, nitro, cyano, carboxy, alkoxycarbonyl, aryl, heteroaryl, cycloalkyl, amino, alkylamino, dialkylamino, aminocarbonyl, or acyl and further wherein the aromatic ring in $R^a$ is optionally substituted with one, two, or three $R^b$ independently selected from alkyl, alkoxy, alkylsulfonyl, hydroxy, or halo;

$R^4$ is hydrogen, alkyl, haloalkyl, aryl, heteroaryl, or heterocycloalkyl attached via a carbon ring atom wherein the aromatic or alicyclic ring in $R^4$ is optionally substituted by one, two, or three $R^f$ independently selected from alkyl, halo, hydroxy, alkoxy, alkylcarbonyl, alkylsulfonyl, alkylsulfonylamino, aminocarbonyl, haloalkyl, haloalkoxy, carboxy, or alkoxycarbonyl;

$R^{4'}$ is difluoromethyl, trifluoromethyl, 1,1,2,2,2-pentafluoroethyl, chlorodifluoromethyl, 1,1-dichloro-2,2,2-trifluoroethyl, 1,1,2,2-tetrafluoroethyl, trichloromethyl, dichlorofluoromethyl, 1,1,2,2,3,3,3-heptafluoropropyl, or 1,1,2,2,3,3-hexafluoropropyl, or a pharmaceutically acceptable salt thereof provided that:

(a) when $R^1$ and $R^2$ taken together with the carbon atom to which $R^1$ and $R^2$ are attached form cyclopropylene, $R^3$ is phenylmethanesulfonylmethyl, cyclopropylmethanesulfonylmethyl, pyridin-2-ylmethanesulfonylmethyl, 2-difluoromethoxyphenylmethanesulfonylmethyl, or 2-trifluoromethylpyridin-6-methanesulfonylmethyl, $R^4$ is phenyl, 4-hydroxyphenyl, 3-bromophenyl, 4-fluorophenyl, 3-chloro-4-hydroxyphenyl, 3,4-difluorophenyl, or 3,4,5-trifluorophenyl, then $R^{4'}$ is not trifluoromethyl or difluoromethyl;

(b) when $R^1$ and $R^2$ taken together with the carbon atom to which $R^1$ and $R^2$ are attached form cyclopropylene, $R^3$ is phenylmethanesulfonylmethyl, difluoromethoxyphenylmethanesulfonylmethyl, or cyclopropylmethanesulfonylmethyl, $R^4$ is furan-2-yl, indol-3-yl, thiophen-2-yl, 1-methylpyrrol-2-yl, pyridin-2-yl, thiophen-3-yl or 1-oxo-1-methylpyrrol-2-yl, then $R^{4'}$ is not difluoromethyl or trifluoromethyl;

(c) when $R^1$ and $R^2$ taken together with the carbon atom to which $R^1$ and $R^2$ are attached form 1,1-dioxohexahydrothiopyran-4-yl, $R^3$ is phenylmethanesulfonylmethyl, 4-fluorophenylmethanesulfonylmethyl, or difluoromethoxyphenylmethanesulfonylmethyl, then $R^{4'}$ is not trifluoromethyl; and (d) when $R^1$ and $R^2$ taken together with the carbon atom to which $R^1$ and $R^2$ are attached form tetrahydropyran-4-yl or tetrahydrothiopyran-4-yl, $R^3$ is cyclopropylmethanesulfonylmethyl or difluoromethoxyphenylmethanesulfonylmethyl, $R^4$ is 4-fluorophenyl, then $R^{4'}$ is not trifluoromethyl.

2. The compound of claim 1 wherein $R^3$ is -alkylene-SO$_2$-haloalkylene-heteroaryl.

3. The compound of claim 1 wherein:

$R^1$ and $R^2$ are cyclopropylene;

$R^3$ is 4-CF$_3$-pyridin-3-ylmethanesulfonylmethyl, pyridin-3-ylmethanesulfonylmethyl, pyridazin-3-ylmethanesulfonylmethyl, 2-CF$_3$-furan-5-ylmethanesulfonylmethyl, pyrimidin-5-ylmethanesulfonylmethyl, 2-CH$_3$-thiazol-4-ylmethanesulfonylmethyl, pyridin-4-ylmethane-sulfonylmethyl, pyrimidin-4-ylmethanesulfonylmethyl, 2-(1-oxopyrrol-1-yl)ethanesulfonyl-methyl, cyclopropylmethanesulfonylmethyl, 3,3,3-trifluoropropane-1-sulfonylmethyl, 2-CF$_3$-pyridin-5-ylmethanesulfonylmethyl, 4-[1.2.4]-triazol-1-ylphenylmethanesulfonylmethyl, 2-(2-oxo-2,3-dihydrobenzimidazol-1-yl)-ethanesulfonylmethyl, 5-oxopyrrolidin-2-ylmethane-sulfonylmethyl, 2-F-pyridin-3-ylmethanesulfonylmethyl, 3-CH$_3$-oxetan-3-ylmethanesulfonyl-methyl, 2-phenylethanesulfonylmethyl, fluoro-pyridin-2-ylmethanesulfonylmethyl, fluoro-pyrazin-2-ylmethanesulfonylmethyl, difluoro-pyridin-2-ylmethanesulfonylmethyl, difluoro-pyridin-3-ylmethanesulfonylmethyl, quinolin-2-ylmethanesulfonylmethyl, benzo[1.2.5]thiadiazol-4-ylmethanesulfonylmethyl, benzothiazol-2-ylmethanesulfonylmethyl, 5-methylisoxazol-3-ylmethanesulfonylmethyl, 2-methylpropylsulfonylmethyl, 2,6-difluorophenylmethanesulfonylmethyl, 2,4-difluorophenylmethane-sulfonylmethyl, quinolin-3-ylmethanesulfonylmethyl, 4,4,4-trifluorobutyl-1-sulfonylmethyl, 2-CF$_3$-phenylmethanesulfonylmethyl, 2-CF$_3$O-phenylmethanesulfonylmethyl, 2-pyridin-2-ylethanesulfonylmethyl, 2-pyridin-3-ylethanesulfonylmethyl, quinolin-8-ylmethane-sulfonylmethyl, 5-methyl-3-phenylisoxazol-4-ylmethanesulfonylmethyl, 4-methyl-2-phenyl-[1.2.3]triazol-5-ylmethanesulfonylmethyl, 2-cyanophenylmethanesulfonylmethyl, 3-methoxycarbonylphenylmethanesulfonylmethyl, pyridin-2-ylmethanesulfonylmethyl, 1-oxopyridin-2-ylmethanesulfonylmethyl, 1-oxopyridin-3-ylmethanesulfonylmethyl, quinoxalin-2-ylmethanesulfonylmethyl, tetrahydropyran-2RS-ylmethanesulfonylmethyl, 2,6-dichloro-phenylmethanesulfonylmethyl, 3-methoxycarbonyl-furan-2-yl-methanesulfonylmethyl, 5-methylisoxazol-3-ylmethanesulfonylmethyl, 2,2-dimethylpropylsulfonylmethyl, ethanesulfonylmethyl, methanesulfonylmethyl, propane-1-sulfonylmethyl, 1H-indol-2-ylmethanesulfonylmethyl, 2-(1H-indol-3-yl)ethanesulfonylmethyl, 2,2,2-trifluoroethanesulfonylmethyl, benzisoxazol-3-ylmethanesulfonylmethyl, 2-tert-butyl-[1.3.4]thiadiazol-5-ylmethanesulfonylmethyl, 2,4,6-trifluorophenylmethanesulfonylmethyl, 2-pyridin-2-ylethanesulfonylmethyl, 1-ethyl-2,5-dioxopyrrolidin-3-ylmethanesulfonylmethyl or benzisoxazol-3-ylmethanesulfonylmethyl]; and $R^4$ is 4-fluorophenyl, 2,3-difluorophenyl, 2,4-difluorophenyl, 2,5-difluorophenyl, or 3,5-difluorophenyl.

4. The compound of claim 1 wherein:

$R^{4'}$ is difluoromethyl, trifluoromethyl, 1,1,2,2,2-pentafluoroethyl, chlorodifluoromethyl, 1,1-dichloro-2,2,2-trifluoroethyl, 1,1,2,2-tetrafluoroethyl, trichloromethyl, dichlorofluoromethyl, 1,1,2,2,3,3,3-heptafluoropropyl, or 1,1,2,2,3,3-hexafluoropropyl; and $R^4$ is hydrogen.

5. The compound of claim 1 wherein:

$R^{4'}$ is difluoromethyl, trifluoromethyl, 1,1,2,2,2-pentafluoroethyl, chlorodifluoromethyl, 1,1-dichloro-2,2,2-trifluoroethyl, 1,1,2,2-tetrafluoroethyl, trichloromethyl, dichlorofluoromethyl, 1,1,2,2,3,3,3-heptafluoropropyl, or 1,1,2,2,3,3-hexafluoropropyl; and $R^4$ is alkyl.

6. The compound of claim 1 wherein:

$R^{4'}$ is difluoromethyl, trifluoromethyl, 1,1,2,2,2-pentafluoroethyl, chlorodifluoromethyl, 1,1-dichloro-2,2,2-trifluoroethyl, 1,1,2,2-tetrafluoroethyl, trichloromethyl, dichlorofluoromethyl, 1,1,2,2,3,3,3-heptafluoropropyl, or 1,1,2,2,3,3-hexafluoropropyl; and $R^4$ is haloalky.

7. The compound of claim 1 wherein $R^3$ is 3,5-dimethylisoxazol-4-ylmethanesulfonylmethyl; 2-$CF_3$-methylphenylmethane-sulfonylmethyl, 3-$CF_3$pyridin-2-ylmethanesulfonylmethyl, 2-F-furan-5-ylmethanesulfonyl-methyl, 2-methylthiazol-4-ylmethanesulfonylmethyl, tetrahydropyran-4-ylmethane-sulfonylmethyl, 1,1-dioxo-1$\lambda^6$-hexahydrothiopyran-4-ylmethanesulfonylmethyl, 1-ethylpiperidin-4-ylmethanesulfonylmethyl, 2-oxo-tetrahydropyrimidin-4-ylmethane-sulfonylmethyl, 1-ethyl-2-oxopiperidin-4-ylmethanesulfonylmethyl, 1-acetylpiperidin-4-ylmethanesulfonylmethyl, 1-ethoxycarbonylpiperidin-4-ylmethanesulfonylmethyl, 1-methylsulfonylpiperidin-4-ylmethanesulfonylmethyl, 1-cyclopropylpiperidin-4-ylmethane-sulfonylmethyl, 1-acetylazetidin-3-ylmethanesulfonylmethyl, 1-ethoxycarbonylazetidin-3-ylmethanesulfonylmethyl, 1-methylsulfonylazetidin-3-ylmethanesulfonylmethyl, 1-ethylazetidin-3-ylmethanesulfonylmethyl, 1-cyclopropylazetidin-3-ylmethanesulfonylmethyl furan-2-ylmethanesulfonylmethyl, difluoro-(4-fluorophenyl) methanesulfonylmethyl, difluoro-(pyrazin-2-yl) methanesulfonylmethyl, difluoro-(2-difluoromethoxyphenyl)-methanesulfonylmethyl, 1-acetylpiperidin-4-ylsulfonylmethyl, 1-ethoxycarbonylpiperidin-4-ylsulfonylmethyl, 1-cyclopropylpiperidin-4-ylsulfonylmethyl, 2-(pyridin-2-yl)ethanesulfonyl-methyl, 2-(pyridin-3-yl)ethanesulfonylmethyl, 2-(pyridin-4-yl) ethanesulfonylmethyl, 3-(pyridin-2-yl) propanesulfonylmethyl, 2,6-difluorophenylmethanesulfonyl, [1.3.5]triazin-2-ylmethanesulfonylmethyl, [1.3.4]thiadiazol-2-ylmethanesulfonylmethyl, oxazol-5-ylmethanesulfonylmethyl, thiazol-5-ylmethanesulfonylmethyl, 4-fluorophenylmethanesulfonylmethyl, 4-aminocarbonylphenylmethanesulfonylmethyl, 4-piperazin-4-ylphenylmethanesulfonylmethyl, 5-fluoroindol-3-ylmethanesulfonylmethyl, 4,6-difluoroindol-3-ylmethanesulfonylmethyl, 1-methylindol-3-ylmethanesulfonylmethyl, 4-fluoroindol-3-ylmethanesulfonylmethyl, 2-(5-fluoroindol-3-yl)ethanesulfonylmethyl, 2-(4,6-difluoroindol-3-yl)ethanesulfonylmethyl, 2-(1-methylindol-3-yl)ethanesulfonylmethyl, 2-(4-fluoroindol-3-yl)ethanesulfonylmethyl, 2-quinolin-3-ylethanesulfonylmethyl, 2-quinolin-2-ylethanesulfonylmethyl, isoquinolin-3-ylmethanesulfonylmethyl, 2-(isoquinolin-3-yl)ethanesulfonylmethyl, 2,4-difluoropyridin-3-ylmethane-sulfonylmethyl, 3,4-difluoropyridin-4-ylmethanesulfonylmethyl, 2-(2,4-difluoropyridin-3-yl)ethanesulfonylmethyl, 2-(3,4-difluoropyridin-4-yl)ethanesulfonylmethyl, fluoro-(2,4-difluoropyridin-3-yl)methanesulfonylmethyl, fluoro-(3,4-difluoropyridin-4-yl) methane-sulfonylmethyl, 2,4-di$CF_3$pyridin-3-ylmethanesulfonylmethyl, 3,4-di$CF_3$pyridin-4-ylmethane-sulfonylmethyl, 2-(2,4-di$CF_3$pyridin-3-yl) ethanesulfonylmethyl, 2-(3,4-di$CF_3$pyridin-4-yl) ethanesulfonylmethyl, fluoro-(2,4-di$CF_3$pyridin-3-yl) methanesulfonylmethyl, fluoro-(3,4-di$CF_3$pyridin-4-yl) methanesulfonylmethyl, 4-F-pyridin-3-ylmethanesulfonylmethyl, 3-F-pyridin-5-ylmethanesulfonylmethyl, 2-F-pyridin-5-ylmethanesulfonylmethyl, 2-F-pyridin-3-ylmethanesulfonylmethyl, 5-F-pyridin-2-ylmethanesulfonylmethyl, 4-F-pyridin-2-ylmethanesulfonylmethyl, 4-F-1-oxopyridin-3-ylmethanesulfonylmethyl, 3-F-1-oxopyridin-5-ylmethanesulfonylmethyl, 2-F-1-oxopyridin-5-ylmethanesulfonylmethyl, 2-F-1-oxopyridin-3-ylmethanesulfonylmethyl, 5-F-1-oxopyridin-2-ylmethanesulfonylmethyl, 4-F-1-oxopyridin-2-ylmethanesulfonylmethyl, 4-$CF_3$-pyridin-2-ylmethanesulfonylmethyl, 3-$CF_3$-pyridin-5-ylmethane-sulfonylmethyl, 3-F-pyridin-2-ylmethanesulfonylmethyl, 2-$CF_3$-pyridin-3-ylmethane-sulfonylmethyl, 4-$CF_3$-1-oxopyridin-2-ylmethanesulfonylmethyl, 3-$CF_3$-1-oxopyridin-5-ylmethanesulfonylmethyl, 3-F-1-oxopyridin-2-ylmethanesulfonylmethyl, 2-$CF_3$-1-oxopyridin-3-ylmethanesulfonylmethyl, 5-$CF_3$-1-oxopyridin-2-ylmethanesulfonylmethyl, 2-$CH_3$-pyridin-6-ylmethanesulfonylmethyl, 3-$CH_3$-pyridin-2-ylmethanesulfonylmethyl, 4-$CH_3$-pyridin-3-ylmethanesulfonylmethyl, 3-$CH_3$-pyridin-4-ylmethanesulfonylmethyl, 2-(2-$CH_3$-pyridin-6-yl) ethanesulfonylmethyl, 2-(3-$CF_3$-pyridin-2-yl) ethanesulfonylmethyl, 2-(4-$CF_3$-pyridin-3-yl)ethanesulfonylmethyl, 2-(3-$CF_3$-pyridin-4-yl)ethanesulfonylmethyl, 2-$C_2H_5$-pyridin-6-ylmethanesulfonylmethyl, 3-$C_2H_5$-pyridin-2-ylmethanesulfonylmethyl, 4-$C_2H_5$-pyridin-3-ylmethanesulfonylmethyl, 3-$C_2H_5$-pyridin-4-ylmethanesulfonylmethyl, 2-(2-$C_2H_5$-pyridin-6-yl)ethanesulfonylmethyl, 2-(3-$C_2H_5$-pyridin-2-yl)ethanesulfonylmethyl, 2-(4-$C_2H_5$-pyridin-3-yl)ethanesulfonylmethyl, 2-(3-$C_2H_5$-pyridin-4-yl) ethanesulfonylmethyl, 2-(2-$CH_3$-pyridin-3-yl)ethanesulfonylmethyl, 2-$CF_3$-pyridin-3-ylmethanesulfonylmethyl, 2-(3-$CF_3$-pyridin-4-yl)ethanesulfonylmethyl, 3-$CF_3$-pyridin-4-ylmethanesulfonylmethyl, cinnolin-3-ylmethanesulfonylmethyl, 2-(cinnolin-3-yl)ethanesulfonylmethyl, phthalazin-1-ylmethanesulfonylmethyl, 2-(phthalazin-1-yl)ethanesulfonylmethyl, 2-(quinoxalin-2-yl)ethanesulfonylmethyl, quinazolin-2-ylmethanesulfonylmethyl, 2-(quinazolin-2-yl)ethanesulfonylmethyl, [1,8]naphthyridin-2-ylmethanesulfonylmethyl, 2-([1,8]naphthyridin-2-yl) ethanesulfonylmethyl, [1,8]naphthyridin-3-ylmethanesulfonylmethyl, 2-([1,8]naphthyridin-3-yl) ethanesulfonylmethyl, 3-Cl-pyridin-2-ylmethanesulfonylmethyl, 4-Cl-pyridin-3-ylmethanesulfonylmethyl, 3-Cl-pyridin-4-ylmethane-sulfonylmethyl, 3-F-pyridin-2-ylmethanesulfonylmethyl, 4-F-pyridin-3-ylmethanesulfonyl-methyl, 3-F-pyridin-4-ylmethanesulfonylmethyl, isoquinolin-4-ylmethanesulfonylmethyl, 6-phenylpyridin-2-ylmethanesulfonylmethyl, 3-phenylpyridin-2-ylmethanesulfonylmethyl, 4-phenylpyridin-3-ylmethanesulfonylmethyl, 3-phenylpyridin-4-ylmethanesulfonylmethyl, 2-(6-phenylpyridin-2-yl) ethanesulfonylmethyl, 2-(3-phenylpyridin-2-yl)ethanesulfonylmethyl, 2-(4-phenylpyridin-3-yl)ethanesulfonylmethyl, 2-(3-phenylpyridin-4-yl)ethanesulfonylmethyl, 6-(pyridin-2-yl)pyridin-2-ylmethanesulfonylmethyl, 3-(pyridin-2-yl) pyridin-2-ylmethane-sulfonylmethyl, 4-(pyridin-2-yl)pyridin-3-ylmethanesulfonylmethyl, 3-(pyridin-2-yl)pyridin-4-ylmethanesulfonylmethyl, 2-[6-(pyridin-2-yl)pyridin-2-yl] ethanesulfonylmethyl, 2-[3-(pyridin-2-yl)pyridin-2-yl] ethanesulfonylmethyl, 2-[4-(pyridin-2-yl)pyridin-3-yl] ethanesulfonylmethyl, 2-[3-(pyridin-2-yl)pyridin-4-yl] ethanesulfonylmethyl, 6-(pyridin-3-yl)pyridin-2-ylmethanesulfonylmethyl, 3-(pyridin-3-yl)pyridin-2-ylmethanesulfonylmethyl, 4-(pyridin-3-yl)pyridin-3- ylmethanesulfonylmethyl, 3-(pyridin-3-yl)pyridin-4-ylmethanesulfonylmethyl, 2-[6-(pyridin-3-yl)pyridin-2-yl]ethanesulfonylmethyl, 2-[3-(pyridin-3-yl)pyridin-2-yl]ethanesulfonylmethyl, 2-[4-(pyridin-3-yl)pyridin-3-yl]ethanesulfonylmethyl, 2-[3-(pyridin-3-yl)pyridin-4-yl]ethanesulfonylmethyl, 6-(pyridin-4-yl)pyridin-2-ylmethanesulfonylmethyl, 3-(pyridin-4-yl)pyridin-2-ylmethanesulfonylmethyl, 4-(pyridin-4-yl)pyridin-3-ylmethanesulfonylmethyl, 3-(pyridin-4-yl)pyridin-4-ylmethanesulfonylmethyl, 2-[6-(pyridin-4-yl)pyridin-2-yl]ethanesulfonylmethyl, 2-[3-(pyridin-4-yl)pyridin-2-yl]ethanesulfonylmethyl, 2-[4-(pyridin-4-yl)pyridin-3-yl]ethanesulfonylmethyl, 2-[3-(pyridin-4-yl)pyridin-4-yl]ethanesulfonylmethyl, 2,2-dimethylcyclopropylmethanesulfonylmethyl, biphen-2-ylmethanesulfonylmethyl, 2-thiophen-2-ylphenylmethanesulfonylmethyl, 2-thiazol-2-ylphenylmethanesulfonylmethyl, 2-thiazol-5-ylphenylmethanesulfonylmethyl, 2-[1.2.3]thiadiazol-5-ylphenylmethane-sulfonylmethyl, 2-isoxazol-5-ylphenylmethanesulfonylmethyl, 2-(1-methylpyrazol-5-yl)phenyl-methanesulfonylmethyl, 2-[1.2.3]triazol-5-ylphenylmethanesulfonylmethyl, 2-[1.2.3]oxadiazol-5-ylphenylmethanesulfonylmethyl, 2-[(1.2.3)triazol-5-yl]phenylmethanesulfonylmethyl, 2-[(1.2.3)triazol-1-yl]phenylmethanesulfonylmethyl, oxazolo[5,4-b]pyridin-2-ylmethane-sulfonylmethyl, oxazolo[4,5-c]pyridin-2-ylmethanesulfonylmethyl, oxazolo[4,5-b]pyridin-2-ylmethanesulfonylmethyl, benzimidazol-5-ylmethanesulfonylmethyl, benzimidazol-4-ylmethanesulfonylmethyl, 3H-imidazo[4,5-b]pyridin-2-ylmethanesulfonylmethyl, 3H-imidazo[4,5-c]pyridin-2-ylmethanesulfonylmethyl, 3-$CF_3$-3H-imidazo[4,5-b]pyridin-2-ylmethanesulfonylmethyl, 3-$CF_3$-3H-imidazo[4,5-c]pyridin-2-ylmethanesulfonylmethyl, 1-$CF_3$-1H-imidazo[4,5-c]pyridin-2-ylmethanesulfonylmethyl, 1-$CF_3$-1H-imidazo[4,5-b]pyridin-2-ylmethanesulfonylmethyl, thiazolo[5,4-b]pyridin-2-ylmethanesulfonylmethyl, thiazolo[4,5-c]pyridin-2-ylmethanesulfonylmethyl, thiazolo[4,5-b]pyridin-2-ylmethanesulfonylmethyl, 5-$CF_3$thiazolo[5,4-b]pyridin-2-ylmethanesulfonylmethyl, 4-$CF_3$-thiazolo[4,5-c]pyridin-2-ylmethanesulfonylmethyl, 7-$CF_3$-thiazolo[4,5-b]pyridin-2-ylmethanesulfonylmethyl, 3-$CF_3$-1H-pyrrolo[2,3-b]pyridin-2-ylmethanesulfonylmethyl, 3-$CF_3$-1H-pyrrolo[3,2-c]pyridin-2-ylmethanesulfonylmethyl, 3-$CF_3$-1H-pyrrolo[3,2-b]pyridin-2-ylmethanesulfonylmethyl, imidazo[1,2-c]pyrimidin-2-methanesulfonylmethyl, 8-$CF_3$-imidazo[1,2-c]pyrimidin-2-methanesulfonylmethyl, imidazo[1,2-a]pyrimidin-2-methanesulfonylmethyl, 8-$CF_3$-imidazo[1,2-b]pyridazin-2-ylmethanesulfonylmethyl, imidazo[1,2-a]pyrazin-2-methanesulfonylmethyl, 8-$CF_3$-imidazo[1,2-a]pyrazin-2-methanesulfonylmethyl, pyrazolo[1,5-c]pyrimidin-2-ylmethanesulfonylmethyl, 3-$CF_3$-pyrazolo[1,5-c]pyrimidin-2-ylmethanesulfonylmethyl, 4-$CF_3$-pyrazolo[1,5-c]pyrimidin-2-ylmethanesulfonylmethyl, imidazo[1,2-d][1,2,4]triazin-2-methanesulfonylmethyl, 3-$CF_3$-imidazo[1,2-d][1,2,4]triazin-2-methanesulfonylmethyl, [1,3]benzoxazol-2-ylmethanesulfonylmethyl, 5-F-[1,3]benzoxazol-2-ylmethanesulfonylmethyl [1,3]benzoxazol-4-ylmethanesulfonylmethyl, 2-$CF_3$-[1,3]benzoxazol-4-ylmethanesulfonyl-methyl, [1,3]benzoxazol-7-ylmethanesulfonylmethyl, 2-$CF_3$-[1,3]benzoxazol-7-ylmethane-sulfonylmethyl, [1,2]benzoxazol-3-ylmethanesulfonylmethyl, [1,2]benzoxazol-4-ylmethanesulfonylmethyl, 5-$CF_3$-[1,2]benzoxazol-4-ylmethanesulfonylmethyl, 3-$CF_3$-[1,2]benzoxazol-4-ylmethanesulfonylmethyl, 6-$CF_3$-[1,2]benzoxazol-7-ylmethane-sulfonylmethyl, 6-CN-[1,2]benzoxazol-7-ylmethanesulfonylmethyl, 3-$CF_3$-[1,2]benzoxazol-7-ylmethanesulfonylmethyl, 5-F-[1,2]benzoxazol-3-ylmethanesulfonylmethyl, [2,3]benzoxazol-7-ylmethanesulfonylmethyl, 6-$CF_3$-[2,3]benzoxazol-7-ylmethanesulfonylmethyl, 1-$CF_3$-[2,3]benzoxazol-7-ylmethanesulfonylmethyl, 5-$CF_3$-[2,3]benzoxazol-4-ylmethane-sulfonylmethyl, 5-CN-[2,3]benzoxazol-4-ylmethanesulfonylmethyl, 1-$CF_3$-[2,3]benzoxazol-4-ylmethanesulfonylmethyl, benzothiazol-2-ylmethanesulfonylmethyl, 5-F-benzothiazol-2-ylmethanesulfonylmethyl, benzothiazol-4-ylmethanesulfonylmethyl, 2-$CF_3$-benzothiazol-4-ylmethanesulfonylmethyl, benzothiazol-7-ylmethanesulfonylmethyl, 2-$CF_3$-benzothiazol-7-ylmethanesulfonylmethyl, [1,2]benzothiazol-3-ylmethanesulfonylmethyl, [1,2]benzothiazol-4-ylmethanesulfonylmethyl, 5-$CF_3$-[1,2]benzothiazol-4-ylmethanesulfonylmethyl, 3-$CF_3$-[1,2]benzothiazol-4-ylmethanesulfonylmethyl, 6-$CF_3$-[1,2]benzothiazol-7-ylmethane-sulfonylmethyl, 6-CN-[1,2]benzothiazol-7-ylmethanesulfonylmethyl, 3-$CF_3$-[1,2]benzothiazol-7-ylmethanesulfonylmethyl, 5-[1,2]benzothiazol-3-ylmethanesulfonylmethyl, [2,3]benzothiazol-7-ylmethanesulfonylmethyl, 6-$CF_3$-[2,3]benzothiazol-7-ylmethane-sulfonylmethyl, 1-$CF_3$-[2,3]benzothiazol-7-ylmethanesulfonylmethyl, 5-$CF_3$-[2,3]benzothiazol-4-ylmethanesulfonylmethyl, 5-CN-[2,3]benzothiazol-4-ylmethanesulfonylmethyl, 1-$CF_3$-[2,3]benzothiazol-4-ylmethanesulfonylmethyl, 4-$CF_3$-2-$CH_3$-thiazol-5-ylmethanesulfonylmethyl, 4-$CF_3$-thiazol-5-ylmethanesulfonylmethyl, 4-$CF_3$-2-phenyl-thiazol-5-ylmethanesulfonylmethyl, 5-$CF_3$-2-$CH_3$-thiazol-4-ylmethanesulfonylmethyl, 5-$CF_3$-thiazol-4-ylmethanesulfonylmethyl, 5-$CF_3$-2-phenyl-thiazol-4-ylmethanesulfonylmethyl, 5-$CH_3$-thiazol-2-ylmethanesulfonylmethyl, 5-$CF_3$-thiazol-2-ylmethanesulfonylmethyl, 5-phenyl-thiazol-2-ylmethanesulfonylmethyl, 4-$CH_3$-thiazol-2-ylmethanesulfonylmethyl, 4-$CF_3$-thiazol-2-ylmethanesulfonylmethyl, 4-phenyl-thiazol-2-ylmethanesulfonylmethyl, 5-$CH_3$-2-(pyridin-2-yl)-[1,2,3]triazol-4-ylmethanesulfonylmethyl, 5-$CF_3$-2-(pyridin-2-yl)-[1,2,3]triazol-4-ylmethanesulfonylmethyl, 5-$CF_3$-2-(4-methylsulfonylphenyl)-[1,2,3]triazol-4-ylmethane-sulfonylmethyl, 4,5-dimethyl-[1,2,4]triazol-3-ylmethanesulfonylmethyl, 5-$CF_3$-4-$CH_3$-[1,2,4]triazol-3-ylmethanesulfonylmethyl, 4-$CH_3$-5-phenyl-[1,2,4]triazol-3-ylmethane-sulfonylmethyl, 5-$CF_3$-4-cyclopropyl-[1,2,4]triazol-3-ylmethanesulfonylmethyl, 2,5-dimethyl-[1,2,4]triazol-3-ylmethanesulfonylmethyl, 5-$CF_3$-2-$CH_3$-[1,2,4]triazol-3-ylmethane-sulfonylmethyl, 2-$CH_3$-5-phenyl-[1,2,4]triazol-3-ylmethanesulfonylmethyl, 2-cyclopropyl-5-phenyl-[1,2,4]triazol-3-ylmethanesulfonylmethyl, 5-$CF_3$-1-$CH_3$-[1,2,4]triazol-3-ylmethane-sulfonylmethyl, 1-$CH_3$-5-phenyl-[1,2,4]triazol-3-ylmethanesulfonylmethyl, 5-$CH_3$-1-phenyl-[1,2,4]triazol-3-ylmethanesulfonylmethyl, 3-$CH_3$-[1,2,4]oxadiazol-5-ylmethanesulfonylmethyl 3-$CF_3$-[1,2,4]oxadiazol-5-ylmethanesulfonylmethyl, 3-phenyl-[1,2,4]oxadiazol-5-ylmethane-sulfonylmethyl, 5-$CH_3$-[1,2,4]oxadiazol-3-ylmethanesulfonylmethyl, 5-$CF_3$-[1,2,4]oxadiazol-3-ylmethanesulfonylmethyl, 5-phenyl-[1,2,4]oxadiazol-3-ylmethanesulfonylmethyl, 2-$CH_3$-[1,3,4]oxadiazol-5-ylmethanesulfonylmethyl, 2-$CF_3$-[1,3,4]oxadiazol-5-ylmethane-sulfonylmethyl, 2-phenyl-[1,3,4]oxadiazol-5-ylmethanesulfonylmethyl, 3-$CH_3$-[1,2,4]thiadiazol-5-ylmethanesulfonylmethyl, 3-$CF_3$-[1,2,4]

thiadiazol-5-ylmethanesulfonylmethyl, 3-phenyl-[1,2,4]thiadiazol-5-ylmethanesulfonylmethyl, 5-CH$_3$-[1,2,4]thiadiazol-3-ylmethane-sulfonylmethyl, 5-CF$_3$-[1,2,4]thiadiazol-3-ylmethanesulfonylmethyl, 5-phenyl-[1,2,4]thiadiazol-3-ylmethanesulfonylmethyl, 2-CH$_3$-[1,3,4]thiadiazol-5-ylmethanesulfonylmethyl, 2-CF$_3$-[1,3,4]thiadiazol-5-ylmethanesulfonylmethyl, 2-phenyl-[1,3,4]thiadiazol-5-ylmethane-sulfonylmethyl, 2,2-difluoropyrrolidinylmethanesulfonylmethyl, 3,3-difluoropyrrolidinyl-methanesulfonylmethyl, 3-CF$_3$—N—CH$_3$-pyrrol-2-ylmethanesulfonylmethyl, 3-CN—N—CH$_3$-pyrrol-2-ylmethanesulfonylmethyl, 4-CF$_3$—N—CH$_3$-pyrrol-2-ylmethanesulfonylmethyl, 4-(1-CH$_3$-1-hydroxyethyl)-N—CH$_3$-pyrrol-2-ylmethanesulfonylmethyl, 1,3-dimethylpyrrol-2-ylmethane-sulfonylmethyl, 4-CF$_3$—N—CH$_3$-pyrrol-3-ylmethanesulfonylmethyl, 4-CN—N—CH$_3$-pyrrol-3-ylmethanesulfonylmethyl, 4-CN-N-(3,3,3-trifluoropropyl)-pyrrol-3-ylmethanesulfonylmethyl, 2-CF$_3$—N—CH$_3$-pyrrol-3-ylmethanesulfonylmethyl, 2-CF$_3$-N-phenyl-pyrrol-3-ylmethane-sulfonylmethyl, 4-CF$_3$-pyrrol-2-ylmethanesulfonylmethyl, 4-(1-CH$_3$-1-hydroxyethyl)-pyrrol-2-ylmethanesulfonylmethyl, 3-CH$_3$-pyrrol-2-ylmethanesulfonylmethyl, 4-CF$_3$-pyrrol-3-ylmethane-sulfonylmethyl, 2-CF$_3$-pyrrol-3-ylmethanesulfonylmethyl, 3-CF$_3$-pyrrol-2-ylmethane-sulfonylmethyl, 2-CF$_3$-pyrrol-4-ylmethanesulfonylmethyl, 2-CF$_3$—N—CH$_3$-pyrrol-4-yl-methane-sulfonylmethyl, 3-CF$_3$-fur-2-ylmethanesulfonylmethyl, 3-CN-fur-2-ylmethanesulfonylmethyl, 3-CF$_3$-fur-4-ylmethanesulfonylmethyl, 3-CN-fur-4-ylmethanesulfonylmethyl, 2-CF$_3$-fur-3-ylmethanesulfonylmethyl, 3-CF$_3$-thiazol-2-ylmethanesulfonylmethyl, 3-CN-thiazol-2-ylmethanesulfonylmethyl, 3-CF$_3$-thiazol-4-ylmethanesulfonylmethyl, 3-CN-thiazol-4-ylmethanesulfonylmethyl, 2-CF$_3$-thiazol-3-ylmethanesulfonylmethyl, N—CH$_3$-3-CF$_3$-1H-pyrazol-5-ylmethanesulfonylmethyl, N—CH$_3$-3-(1-CH$_3$-1-hydroxyethyl)-1H-pyrazol-5-ylmethane-sulfonylmethyl, N—CH$_3$-3-phenyl-1H-pyrazol-5-ylmethanesulfonylmethyl, N—CH$_3$-3-CF$_3$-1H-pyrazol-4-ylmethanesulfonylmethyl, N—CH$_3$-4-CN-1H-pyrazol-3-ylmethanesulfonylmethyl, N-phenyl-4-CN-1H-pyrazol-3-ylmethanesulfonylmethyl, N-phenyl-3-CF$_3$-1H-pyrazol-4-ylmethanesulfonylmethyl, N-phenyl-5-CF$_3$-1H-pyrazol-4-ylmethanesulfonylmethyl, (N—CH$_3$-4-CF$_3$-1H-imidazol-2-ylmethane)-sulfonylmethyl, [N—CH$_3$-4-(1-CH$_3$-1-hydroxyethyl)-1H-imidazol-2-ylmethane]-sulfonylmethyl, (N—CH$_3$-4-phenyl-1H-imidazol-2-ylmethane)-sulfonylmethyl, N—CH$_3$-3-CF$_3$-1H-pyrazol-4-ylmethanesulfonylmethyl, (N—CH$_3$-2-CF$_3$-1H-imidazol-5-ylmethane)-sulfonylmethyl, (N—CH$_3$-2-phenyl-1H-imidazol-5-ylmethane)-sulfonylmethyl, (N—CH$_3$-5-CF$_3$-1H-imidazol-4-ylmethane)-sulfonylmethyl, (N-phenyl-5-CF$_3$-1H-imidazol-4-ylmethane)-sulfonylmethyl, 4-CN-[1,2]oxazol-5-ylmethanesulfonylmethyl, 4-CN-3-phenyl-[1,2]oxazol-5-ylmethanesulfonylmethyl, 4-CN-[1,2]oxazol-3-ylmethanesulfonylmethyl, 4-CN-5-phenyl-[1,2]oxazol-3-ylmethanesulfonylmethyl, 4-CN-isothiazol-5-ylmethanesulfonylmethyl, 4-CN-3-phenyl-isothiazol-5-ylmethanesulfonylmethyl, 4-CN-isothiazol-3-ylmethanesulfonylmethyl, 4-CN-5-phenyl-isothiazol-3-ylmethane-sulfonylmethyl, 4-CF$_3$-[1,2]oxazol-5-ylmethanesulfonylmethyl, 4-CF$_3$-3-CH$_3$-[1,2]oxazol-5-ylmethanesulfonylmethyl, 4-CF$_3$-3-phenyl-[1,2]oxazol-5-ylmethanesulfonylmethyl, 4-CF$_3$-[1,2]oxazol-3-ylmethanesulfonylmethyl, 4-CF$_3$-5-CH$_3$-[1,2]oxazol-3-ylmethanesulfonylmethyl, 4-CF$_3$-5-phenyl-[1,2]oxazol-3-ylmethanesulfonylmethyl, 3-CF$_3$-[1,2]oxazol-4-ylmethanesulfonylmethyl, 5-CF$_3$-[1,2]oxazol-4-ylmethanesulfonylmethyl, 4-CF$_3$-[1,2]oxazol-5-ylmethanesulfonylmethyl, 4-CF$_3$-3-CH$_3$-[1,2]oxazol-5-ylmethanesulfonylmethyl, 4-CF$_3$-3-phenyl-[1,2]oxazol-5-ylmethanesulfonylmethyl, 4-CF$_3$-[1,2]oxazol-3-ylmethanesulfonylmethyl, 4-CF$_3$-5-CH$_3$-[1,2]oxazol-3-ylmethanesulfonylmethyl, 4-CF$_3$-5-phenyl-[1,2]oxazol-3-ylmethanesulfonylmethyl, 3-CF$_3$-[1,2]oxazol-4-ylmethanesulfonylmethyl, 5-CF$_3$-[1,2]oxazol-4-ylmethanesulfonylmethyl, 4-CH$_3$-[1,2]oxazol-5-ylmethanesulfonylmethyl, 4-CH$_3$-3-phenyl-[1,2]oxazol-5-ylmethanesulfonylmethyl, 4-CH$_3$-[1,2]oxazol-3-ylmethanesulfonylmethyl, 4-CH$_3$-5-phenyl-[1,2]oxazol-3-ylmethanesulfonylmethyl, 3-CH$_3$-[1,2]oxazol-4-ylmethane-sulfonylmethyl, 5-CH$_3$-[1,2]oxazol-4-ylmethanesulfonylmethyl, 4-CH$_3$-isothiazol-5-ylmethane-sulfonylmethyl, 4-CH$_3$-3-phenyl-isothiazol-5-ylmethanesulfonylmethyl, 4-CH$_3$-isothiazol-3-ylmethanesulfonylmethyl, 4-CH$_3$-5-phenyl-isothiazol-3-ylmethanesulfonylmethyl, 3-CH$_3$-isothiazol-4-ylmethanesulfonylmethyl, 5-CH$_3$-isothiazol-4-ylmethanesulfonylmethyl, 4-CF$_3$-2-CH$_3$-[1,3]oxazol-5-ylmethanesulfonylmethyl, 4-CF$_3$-[1,3]oxazol-5-ylmethanesulfonylmethyl, 4-CF$_3$-2-phenyl-[1,3]oxazol-5-ylmethanesulfonylmethyl, 5-CF$_3$-2-CH$_3$-[1,3]oxazol-4-ylmethanesulfonylmethyl, 5-CF$_3$-[1,3]oxazol-4-ylmethanesulfonylmethyl, 5-CF$_3$-2-phenyl-[1,3]oxazol-4-ylmethanesulfonylmethyl, 5-CH$_3$-[1,3]oxazol-2-ylmethanesulfonylmethyl, 5-CF$_3$-[1,3]oxazol-2-ylmethanesulfonylmethyl, 5-phenyl-[1,3]oxazol-2-ylmethane-sulfonylmethyl, 4-CH$_3$-[1,3]oxazol-2-ylmethanesulfonylmethyl, 4-CF$_3$-[1,3]oxazol-2-ylmethanesulfonylmethyl, 4-phenyl-[1,3]oxazol-2-ylmethanesulfonylmethyl, N-methyl-indol-2-ylmethanesulfonylmethyl, 3-CF$_3$-indol-2-ylmethanesulfonylmethyl, 3-CF$_3$-N-methyl-indol-2-ylmethanesulfonylmethyl, 5-fluoro-N-methyl-indol-2-ylmethanesulfonylmethyl, N-methyl-indol-3-ylmethanesulfonylmethyl, 2-CF$_3$-indol-3-ylmethanesulfonylmethyl, 2-CF$_3$-N-methyl-indol-3-ylmethanesulfonylmethyl, 5-fluoro-N-methyl-indol-3-ylmethanesulfonylmethyl, 5-CF$_3$-N-methyl-indol-4-ylmethanesulfonylmethyl, 5-CN-N-methyl-indol-4-ylmethane-sulfonylmethyl, 2-CF$_3$-N-methyl-indol-4-ylmethanesulfonylmethyl, 3-CF$_3$-N-methyl-indol-4-ylmethanesulfonylmethyl, 6-CF$_3$-N-methyl-indol-7-ylmethanesulfonylmethyl, 6-CN-N-methyl-indol-7-ylmethanesulfonylmethyl, 2-CF$_3$-N-methyl-indol-7-ylmethanesulfonylmethyl, 3-CF$_3$-N-methyl-indol-7-ylmethanesulfonylmethyl, benzofuran-2-ylmethanesulfonylmethyl, 3-CF$_3$-benzofuran-2-ylmethanesulfonylmethyl, 3-CN-benzofuran-2-ylmethanesulfonylmethyl, 5-F-benzofuran-2-ylmethanesulfonylmethyl, benzofuran-3-ylmethanesulfonylmethyl, 2-CF$_3$-benzofuran-3-ylmethanesulfonylmethyl, 2-CH$_3$-benzofuran-3-ylmethanesulfonylmethyl, 5-F-benzofuran-3-ylmethanesulfonylmethyl, 5-CF$_3$-benzofuran-4-ylmethanesulfonylmethyl, 5-CN-benzofuran-4-ylmethanesulfonylmethyl, 2-CF$_3$-benzofuran-4-ylmethanesulfonylmethyl, 3-CF$_3$-benzofuran-4-ylmethanesulfonylmethyl, 6-CF$_3$-benzofuran-7-ylmethanesulfonylmethyl, 6-CN-benzofuran-7-ylmethanesulfonylmethyl, 2-CF$_3$-benzofuran-7-ylmethanesulfonylmethyl, 3-CF$_3$-benzofuran-7-ylmethanesulfonylmethyl, benzothien-2-ylmethanesulfonylmethyl, (3-CF$_3$-benzothien-2- ylmethane)-sulfonylmethyl, (3-CN-benzothien-2-yl-methane)-sulfonylmethyl, (5-F-benzothien-2-ylmethane)-sulfonylmethyl, benzothien-3-ylmethanesulfonylmethyl, (2-CF$_3$-benzothien-3-ylmethane)-sulfonylmethyl, (2-CH$_3$-benzothien-3-ylmethane)-sulfonylmethyl, (5-fluoro-benzothien-3-ylmethane)-sulfonylmethyl, (5-CF$_3$-benzothien-4-ylmethane)-sulfonylmethyl, (5-CN-benzothien-4-ylmethane)-sulfonylmethyl, (2-CF$_3$-benzothien-4-ylmethane)-sulfonylmethyl, (3-CF$_3$-benzothien-4-ylmethane)-sulfonylmethyl, (6-CF$_3$-benzothien-7-ylmethane)-sulfonylmethyl, (6-CN-benzothien-7-ylmethane)-sulfonylmethyl, (2-CF$_3$-benzothien-7-ylmethane)-sulfonylmethyl, (3-CF$_3$-benzothien-7-ylmethane)-sulfonylmethyl, N-methyl-benzimidazol-2-ylmethanesulfonylmethyl, (5-fluoro-N-methyl-benzimidazol-2-ylmethane)-sulfonylmethyl, (N-methyl-indazol-3-ylmethane)-sulfonylmethyl, (5-fluoro-N-methyl-indazol-3-ylmethane)-sulfonylmethyl, (2-CF$_3$-N-methyl-benzimidazol-4-ylmethane)-sulfonylmethyl, (2-CF$_3$-N-methyl-benzimidazol-7-ylmethane)-sulfonylmethyl, (N-methyl-indazol-4-ylmethane)-sulfonylmethyl, (5-CF$_3$-N-methyl-indazol-4-ylmethane)-sulfonylmethyl, (3-CF$_3$-N-methyl-indazol-4-ylmethane)-sulfonylmethyl, (6-CF$_3$-N-methyl-indazol-7-ylmethane)-sulfonylmethyl, (6-CN-N-methyl-indazol-7-ylmethane)-sulfonylmethyl, or (3-CF$_3$-N-methyl-indazol-7-ylmethane)-sulfonylmethyl.

8. The compound of claim 7 wherein R$^1$ and R$^2$ together with the carbon atom to which they are attached form cycloalkylene.

9. The compound of claim 7 wherein R$^1$ and R$^2$ together with the carbon atom to which they are attached form piperidin-4-yl substituted at the nitrogen with ethyl, trifluoroethyl or cyclopropyl.

10. The compound of claim 7 wherein R$^1$ and R$^2$ together with the carbon atom to which they are attached form tetrahydropyran-4-yl, tetrahydrothiopyran-4-yl, or 1,1-dioxo-hexahydrothiopyran-4-yl.

11. A compound selected from the group consisting of:

N-(1-cyanocyclopropyl)-3-(4-trifluoromethylpyridin-3-ylmethanesulfonyl)-2(R)-(2,2,2-trifluoro-1(S)-4-fluorophenylethylamino)-propionamide;

N-(1-cyanocyclopropyl)-3-pyridin-3-ylmethanesulfonyl-2(R)-(2,2,2-trifluoro-1(S)-4-fluorophenylethylamino) propionamide;

N-(1-cyanocyclopropyl)-3-pyridan-3-ylmethanesulfonyl-2(R)-(2,2,2-trifluoro-1(S)-4-fluorophenylethylamino) propionamide;

N-(1-cyanocyclopropyl)-3-(2-trifluoromethylfuran-5-ylmethanesulfonyl)-2(R)-(2,2,2-trifluoro-1(S)-4-fluorophenylethylamino)-propionamide;

N-(1-cyanocyclopropyl)-3-pyrimidin-5-ylmethanesulfonyl-2(R)-(2,2,2-trifluoro-1(S)-4-fluorophenylethylamino)propionamide;

N-(1-cyanocyclopropyl)-3-(2-methylthiazol-4-ylmethanesulfonyl)-2(R)-(2,2,2-trifluoro-1(S)-4-fluorophenylethylamino)propionamide;

N-(1-cyanocyclopropyl)-3-pyridin-4-ylmethanesulfonyl-2(R)-(2,2,2-trifluoro-1(S)-4-fluorophenylethylamino) propionamide;

N-(1-cyanocyclopropyl)-3-pyrimidin-4-ylmethanesulfonyl-2(R)-(2,2,2-trifluoro-1(S)-4-fluorophenylethylamino)propionamide;

N-(1-cyanocyclopropyl)-3-[2-(1-oxopyrrol-1-yl)ethanesulfonyl]-2(R)-(2,2,2-trifluoro-1(S)-4-fluorophenylethylamino)propionamide;

N-(1-cyanocyclopropyl)-3-pyridin-3-ylmethanesulfonyl-2(R)-(2,2,2-trifluoro-1(R)-4-fluorophenylethylamino) propionamide;

N-(1-cyanocyclopropyl)-3-cyclopropylmethanesulfonyl-2(R)-(2,2,2-trifluoro-1(S)-3-fluorophenylethylamino) propionamide;

N-(1-cyanocyclopropyl)-3-(3,3,3-trifluoropropane-1-sulfonyl)-2(R)-(2,2,2-trifluoro-1(S)-4-fluorophenylethylamino)propionamide;

N-(1-cyanocyclopropyl)-3-(2-trifluoromethylpyridin-5-ylmethanesulfonyl)-2(R)-(2,2,2-trifluoro-1(S)-4-fluorophenylethylamino)-propionamide;

N-(1-cyanocyclopropyl)-3-(4-[1.2.4]-triazol-1-ylphenylmethanesulfonyl)-2(R)-(2,2,2-trifluoro-1(S)-4-fluorophenylethylamino)-propionamide;

N-(1-cyanocyclopropyl)-3-[2-(2-oxo-2,3-dihydrobenzimidazol-1-yl)ethanesulfonyl]-2(R)-(2,2,2-trifluoro-1(S)-4-fluorophenyl-ethylamino)propionamide;

N-(1-cyanocyclopropyl)-3-(5-oxo-pyrrolidin-2-ylmethanesulfonyl)-2(R)-(2,2,2-trifluoro-1(S)-4-fluorophenyl-ethylaminopropionamide;

N-(1-cyanocyclopropyl)-3-(2-fluoropyridin-3-ylmethanesulfonyl)-2(R)-(2,2,2-trifluoro-1(S)-4-fluorophenylethylaminopropionamide;

N-(1-cyanocyclopropyl)-3-(3-methyloxetan-3-ylmethanesulfonyl)-2(R)-(2,2,2-trifluoro-1(S)-4-fluorophenylethylamino)propionamide;

N-(1-cyanocyclopropyl)-3-(2-phenylethanesulfonyl)-2 (R)-(2,2,2-trifluoro-1(S)-4-fluorophenylethylamino) propionamide;

N-(1-cyanocyclopropyl)-3-(3,3,3-trifluoropropane-1-sulfonyl)-2(R)-(2,2,2-trifluoro-1(R)-4-fluorophenylethylamino)propionamide;

N-(1-cyanocyclopropyl)-3-(fluoropyridin-2-ylmethanesulfonyl)-2(R)-(2,2,2-trifluoro-1(S)-4-fluorophenylethylamino)propionamide;

N-(1-cyanocyclopropyl)-3-(fluoropyrazin-2-ylmethanesulfonyl)-2(R)-(2,2,2-trifluoro-1(S)-4-fluorophenylethylamino)propionamide;

N-(1-cyanocyclopropyl)-3-(difluoropyridin-2-ylmethanesulfonyl)-2(R)-(2,2,2-trifluoro-1(S)-4-fluorophenylethylamino)propionamide;

N-(1-cyanocyclopropyl)-3-(difluoropyridin-3-ylmethanesulfonyl)-2(R)-(2,2,2-trifluoro-1(S)-4-fluorophenylethylamino)propionamide;

N-(1-cyanocyclopropyl)-3-(quinolin-2-ylmethanesulfonyl)-2(R)-(2,2,2-trifluoro-1(S)-4-fluorophenylethylamino)propionamide;

N-(1-cyanocyclopropyl)-3-(benzo[1.2.5]thiadiazol-4-ylmethanesulfonyl)-2(R)-(2,2,2-trifluoro-1(S)-4-fluorophenyl-ethylamino)propionamide;

N-(1-cyanocyclopropyl)-3-(benzothiazol-2-ylmethanesulfonyl)-2(R)-(2,2,2-trifluoro-1(S)-4-fluorophenylethylamino)propionamide;

N-(1-cyanocyclopropyl)-3-(5-methylisoxazol-3-ylmethanesulfonyl)-2(R)-(2,2,2-trifluoro-1(S)-4-fluorophenyl-ethylamino)propionamide;

N-(1-cyanocyclopropyl)-3-(2-methylpropylsulfonyl)-2 (R)-(2,2,2-trifluoro-1(S)-4-fluorophenylethylamino) propionamide;

N-(1-cyanocyclopropyl)-3-(cyclobutylmethanesulfonyl)-2(R)-(2,2,2-trifluoro-1(S)-4-fluorophenylethylamino) propionamide;

N-(1-cyanocyclopropyl)-3-(2,6-difluorophenylmethanesulfonyl)-2(R)-(2,2,2-trifluoro-1(S)-4-fluorophenyl-ethylamino)propionamide;

N-(1-cyanocyclopropyl)-3-(2,4-difluorophenylmethane-sulfonyl)-2(R)-(2,2,2-trifluoro-1(S)-4-fluorophenyl-ethylamino)propionamide;

N-(1-cyanocyclopropyl)-3-(quinolin-3-ylmethanesulfo-nyl)-2(R)-(2,2,2-trifluoro-1(S)-4-fluorophenylethyl-amino)propionamide;

N-(1-cyanocyclopropyl)-3-(4,4,4-trifluorobutyl-1-sulfo-nyl)-2(R)-(2,2,2-trifluoro-1(S)-4-fluorophenylethyl-amino)propionamide;

N-(1-cyanocyclopropyl)-3-(2-trifluoromethylphenyl methanesulfonyl)-2(R)-(2,2,2-trifluoro-1(S)-4-fluo-rophenylethylamino)-propionamide;

N-(1-cyanocyclopropyl)-3-(2-trifluoromethoxyphenyl-methanesulfonyl)-2(R)-(2,2,2-trifluoro-1(S)-4-fluo-rophenylethylamino)-propionamide;

N-(1-cyanocyclopropyl)-3-(cyclopropylmethanesulfo-nyl)-2(R)-(2,2,2-trifluoro-1(S)-3,5-difluorophenyl-ethylamino)propionamide;

N-(1-cyanocyclopropyl)-3-(cyclopropylmethanesulfo-nyl)-2(R)-(2,2,2-trifluoro-1(S)-2, 5-difluorophenyl-ethylamino)propionamide;

N-(1-cyanocyclopropyl)-3-(2-pyridin-2-ylethanesulfo-nyl)-2(R)-(2,2,2-trifluoro-1(S)-4-fluorophenyl-ethy-lamino)propionamide;

N-(1-cyanocyclopropyl)-3-(2-pyridin-3-ylethanesulfo-nyl)-2(R)-(2,2,2-trifluoro-1(S)-4-fluorophenyl-ethy-lamino)propionamide;

N-(1-cyanocyclopropyl)-3-(quinolin-8-ylmethanesulfo-nyl)-2(R)-(2,2,2-trifluoro-1(S)-4-fluorophenyl-ethy-lamino)propionamide;

N-(1-cyanocyclopropyl)-3-(cyclopropylmethanesulfo-nyl)-2(R)-(2,2,2-trifluoro-1(S)-2,3-difluorophenyl-ethylamino)propionamide;

N-(1-cyanocyclopropyl)-3-(cyclopropylmethanesulfo-nyl)-2(R)-(2,2,2-trifluoro-1(S)-2,4-difluorophenyl-ethylamino)propionamide;

N-(1-cyanocyclopropyl)-3-(5-methyl-3-phenylisoxazol-4-ylmethanesulfonyl)-2(R)-(2,2,2-trifluoro-1(S)-4-fluorophenyl ethylamino)-propionamide;

N-(1-cyanocyclopropyl)-3-(4-methyl-2-phenyl-[1.2.3] triazol-5-ylmethanesulfonyl)-2(R)-(2,2,2-trifluoro-1 (S)-4-fluorophenyl-ethylamino)-propionamide;

N-(1-cyanocyclopropyl)-3-(2-cyanophenylmethanesulfo-nyl)-2(R)-(2,2,2-trifluoro-1(S)-4-fluorophenyl-ethy-lamino)propionamide;

N-(1-cyanocyclopropyl)-3-(3-methoxycarbonylphenyl-methanesulfonyl)-2(R)-(2,2,2-trifluoro-1(S)-4-fluo-rophenylethylamino)-propionamide;

N-(1-cyanocyclopropyl)-3-(cyclopropylmethanesulfo-nyl)-2(R)-(2,2-difluoro-1(S)-4-fluorophenyl-ethy-lamino)propionamide;

N-(1-cyanocyclopropyl)-3-(cyclopropylmethanesulfo-nyl)-2(R)-(2,2,2-trifluoro-1(RS)-2-chloropyridin-5-yl-ethylamino)propionamide;

N-(1-cyanocyclopropyl)-3-(pyridin-2-ylmethanesulfo-nyl)-2(R)-(2,2,3,3,3-pentafluoro-1(S)-4-fluorophenyl-propylamino)propionamide;

N-(1-cyanocyclopropyl)-3-(1-oxopyridin-2-ylmethane-sulfonyl)-2(R)-(2,2,3,3,3-pentafluoro-1(S)-4-fluo-rophenylpropylamino)-propionamide;

N-(1-cyanocyclopropyl)-3-(pyridin-3-ylmethanesulfo-nyl)-2(R)-(2,2,3,3,3-pentafluoro-1(S)-4-fluorophenyl-propylamino)propionamide;

N-(1-cyanocyclopropyl)-3-(1-oxopyridin-3-ylmethane-sulfonyl)-2(R)-(2,2,3,3,3-pentafluoro-1(S)-4-fluo-rophenylpropylamino)-propionamide;

N-(1-cyanocyclopropyl)-3-(cyclopropylmethanesulfo-nyl)-2(R)-(2,2,3,3,3-pentafluoro-1(S)-4-fluorophenyl-propylamino)propionamide;

N-(1-cyanocyclopropyl)-3-(quinoxalin-2-ylmethane-sulfonyl)-2(R)-(2,2,2-trifluoro-1(S)-4-fluorophenyl-ethylamino)propionamide;

N-(1-cyanocyclopropyl)-3-(tetrahydropyran-2RS-yl-methanesulfonyl)-2(R)-(2,2,2-trifluoro-1(S)-4-fluo-rophenylethylamino)-propionamide;

N-(1-cyanocyclopropyl)-3-(2,6-dichlorophenylmethane-sulfonyl)-2(R)-(2,2,2-trifluoro-1(S)-4-fluorophenyl-ethylamino)propionamide;

N-(1-cyanocyclopropyl)-3-(3-methoxycarbonylfuran-2RS-ylmethanesulfonyl)-2(R)-(2,2,2-trifluoro-1(S)-4-fluorophenylethylamino)-propionamide;

N-(1-cyanocyclopropyl)-3-(5-methylisoxazol-3-yl-methanesulfonyl)-2(R)-(2,2,3,3,3-pentafluoro-1(S)-4-fluorophenylpropylamino)-propionamide;

N-(1-cyanocyclopropyl)-3-(2,2-dimethylpropylsulfonyl)-2(R)-(2,2,2-trifluoro-1(S)-4-fluorophenylethylamino) propionamide;

N-(1-cyanocyclopropyl)-3-(pyridin-3-ylmethanesulfo-nyl)-2(R)-(2,2,3,3,3-pentafluoro-1(R)-4-fluorophenyl-propylamino)propionamide;

N-(1-cyanocyclopropyl)-3-(ethanesulfonyl)-2(R)-(2,2,2-trifluoro-1(S)-4-fluorophenylethylamino)propiona-mide;

N-(1-cyanocyclopropyl)-3-(cyclopropylmethanesulfo-nyl)-2(R)-(2,2,2-trifluoro-1(R)-2,5-difluorophenyl-ethylamino)propionamide;

N-(1-cyanocyclopropyl)-3-(cyclopropylmethanesulfo-nyl)-2(R)-(2,2,2-trifluoro-1(S)-2,6-difluorophenyl-ethylamino)propionamide;

N-(1-cyanocyclopropyl)-3-(cyclopropylmethanesulfo-nyl)-2(R)-(2,2,2-trifluoro-1(R)-2,6-difluorophenyl ethylamino)propionamide;

N-(1-cyanocyclopropyl)-3-(cyclopropylmethanesulfo-nyl)-2(R)-(2,2,2-trifluoro-1(R)-2,3-difluorophenyl-ethylamino)propionamide;

N-(1-cyanocyclopropyl)-3-(cyclopropylmethanesulfo-nyl)-2(R)-(2,2,2-trifluoro-1(R)-2,4-difluorophenyl-ethylamino)propionamide;

N-(1-cyanocyclopropyl)-3-(methanesulfonyl)-2(R)-(2,2, 2-trifluoro-1(S)-4-fluorophenylethylamino)propiona-mide;

N-(1-cyanocyclopropyl)-3-(propane-1-sulfonyl)-2(R)-(2, 2,2-trifluoro-1(S)-4-fluorophenylethylamino)propiona-mide;

N-(1-cyanocyclopropyl)-3-(1H-indol-2-ylmethanesulfo-nyl)-2(R)-(2,2,2-trifluoro-1(S)-4-fluorophenylethy-lamino)propionamide;

N-(1-cyanocyclopropyl)-3-(cyclopropylmethanesulfo-nyl)-2(R)-(2,2,2-trifluoro-1(S)-2-fluorophenylethy-lamino)propionamide;

N-(1-cyanocyclopropyl)-3-(cyclopropylmethanesulfo-nyl)-2(R)-(2,2,2-trifluoro-1(R)-2-fluorophenylethy-lamino)propionamide;

N-(1-cyanocyclopropyl)-3-(pyridin-2-ylmethanesulfo-nyl)-2(R)-(2,2,2-trifluoro-1(S)-3,4-difluorophenyl-ethylamino)propionamide;

N-(1-cyanocyclopropyl)-3-(pyridin-3-ylmethanesulfo-nyl)-2(R)-(2,2,2-trifluoro-1(S)-3,4-difluorophenyl-ethylamino)propionamide;

N-(1-cyanocyclopropyl)-3-[2-(1H-indol-3-yl)ethane-sulfonyl]-2(R)-(2,2,2-trifluoro-1(S)-4-fluorophenyl-ethylamino)propionamide;

N-(1-cyanocyclopropyl)-3-(tetrahydropyran-4-yl-methanesulfonyl)-2(R)-(2,2,2-trifluoro-1(S)-4-fluorophenylethylamino)propionamide;

N-(1-cyanocyclopropyl)-3-(1-oxopyridin-2-ylmethanesulfonyl)-2(R)-(2,2,2-trifluoro-1(S)-2-fluorophenylethylamino)propionamide;

N-(1-cyanocyclopropyl)-3-(1-oxopyridin-2-ylmethanesulfonyl)-2(R)-(2,2,2-trifluoro-1(R)-2-fluorophenylethylamino)propionamide;

N-(1-cyanocyclopropyl)-3-(pyridin-2-ylmethanesulfonyl)-2(R)-(2,2,2-trifluoro-1(S)-2-fluorophenylethylamino)propionamide;

N-(1-cyanocyclopropyl)-3-(pyridin-2-ylmethanesulfonyl)-2(R)-(2,2,2-trifluoro-1(R)-2-fluorophenylethylamino)propionamide;

N-(1-cyanocyclopropyl)-3-(cyclopropylmethanesulfonyl)-2(R)-(2,2,2-trifluoro-1(S)-2,3,4-trifluorophenylethylamino)propionamide;

N-(1-cyanocyclopropyl)-3-(cyclopropylmethanesulfonyl)-2(R)-(2,2,2-trifluoro-1(R)-2,3,4-trifluorophenylethylamino)propionamide;

N-(1-cyanocyclopropyl)-3-(2,2,2-trifluoroethanesulfonyl)-2(R)-(2,2,2-trifluoro-1(S)-2-fluorophenylethylamino)propionamide;

N-(1-cyanocyclopropyl)-3-(benzisoxazol-3-ylmethanesulfonyl)-2(R)-(2,2,2-trifluoro-1(S)-2-fluorophenylethylamino)propionamide;

N-(1-cyano-cyclopropyl)-3-cyclopropylmethanesulfonyl-2(R)-[2,2,2-trifluoro-1 (RS)-(3-hydroxy-6-methyl-pyridin-2-yl)-ethylamino]-propionamide;

N-(1-cyanocyclopropyl)-3-(2-tert-butyl-[1.3.4]-thiadiazol-5-ylmethanesulfonyl)-2(R)-(2,2,2-trifluoro-1(S)-4-fluorophenylethylamino)propionamide;

N-(1-cyanocyclopropyl)-3-(2,4,6-trifluorophenyl-methanesulfonyl)-2(R)-(2,2,2-trifluoro-1(S)-4-fluorophenylethylamino)propionamide;

N-(1-cyanocyclopropyl)-3-(2-pyridin-2-ylethanesulfonyl)-2(R)-(2,2,3,3,3-pentafluoro-1(S)-4-fluorophenyl-propylamino)propionamide;

N-(1-cyanocyclopropyl)-3-(1-ethyl-2,5-dioxopyrrolidin-3-ylmethanesulfonyl)-2(R)-(2,2,2-trifluoro-1(S)-4-fluorophenyl-ethylamino)propionamide; and N-(1-cyanocyclopropyl)-3-(benzisoxazol-3-ylmethanesulfonyl)-2(R)-(2,2,2-trifluoro-1(S)-4-fluorophenyl-ethylamino)propionamide or a pharmaceutically acceptable salt thereof.

12. A pharmaceutical composition comprising a compound of claim 1 in admixture with one or more suitable excipients.

13. A method for treating a disease in an animal mediated by Cathepsin S which method comprises administering to the animal a pharmaceutical composition comprising a compound of claim 1 in admixture with one or more suitable excipients wherein the disease is rheumatoid arthritis, multiple sclerosis, myasthenia gravis, psoriasis, pemphigus vulgaris, Graves' disease, systemic lupus erythemotasus, asthma, pain, and atherosclerosis.

* * * * *